US012804352B2

(12) United States Patent
Williams et al.

(10) Patent No.: US 12,804,352 B2
(45) Date of Patent: Nov. 17, 2026

(54) SYSTEMS AND METHODS FOR THE MANAGEMENT, MONITORING, IMPROVEMENT, AND RESEARCH OF MEDICINE AND HEALTH IN OFF-EARTH, NON-EARTH, AND SPECIALTY ENVIRONMENTS

(71) Applicant: Conquer Your Addiction LLC, Kirkwood, MO (US)

(72) Inventors: David H. Williams, Kirkwood, MO (US); Adam H. Williams, Kirkwood, MO (US)

(73) Assignee: Conquer Your Addiction LLC, Kirkwood, MO (US)

( * ) Notice: Subject to any disclaimer, the term of this patent is extended or adjusted under 35 U.S.C. 154(b) by 767 days.

(21) Appl. No.: 18/211,999

(22) Filed: Jun. 20, 2023

(65) Prior Publication Data

US 2023/0353983 A1 Nov. 2, 2023

Related U.S. Application Data

(63) Continuation-in-part of application No. 18/090,047, filed on Dec. 28, 2022, now Pat. No. 12,739,596, which is a continuation-in-part of application No. 17/903,419, filed on Sep. 6, 2022, now Pat. No. 12,470,894, which is a continuation-in-part of application No. 17/882,061, filed on Aug. 5, 2022, now Pat. No. 12,289,654, said application No.
(Continued)

(51) Int. Cl.

| | |
|---|---|
| ***H04W 4/029*** | (2018.01) |
| ***A61B 5/16*** | (2006.01) |
| ***G06Q 50/26*** | (2012.01) |
| ***H04W 4/021*** | (2018.01) |

(52) U.S. Cl.
CPC ............ *H04W 4/029* (2018.02); *A61B 5/165* (2013.01); *G06Q 50/265* (2013.01); *H04W 4/021* (2013.01)

(58) Field of Classification Search
CPC .... H04W 4/021; H04W 4/029; G06Q 50/265; A61B 5/165
See application file for complete search history.

(56) References Cited

U.S. PATENT DOCUMENTS

| | | |
|---|---|---|
| 5,601,598 A | 2/1997 | Fisher |
| 5,722,418 A | 3/1998 | Bro |

(Continued)

FOREIGN PATENT DOCUMENTS

| | | |
|---|---|---|
| JP | 5867847 B2 | 2/2016 |
| JP | 5877528 B2 | 3/2016 |

(Continued)

OTHER PUBLICATIONS

Campbell, Discovering addiction: The science and politics of substance abuse research, 2007, Abstract, 2 pages.

(Continued)

*Primary Examiner* — Dai Phuong
(74) *Attorney, Agent, or Firm* — Harness, Dickey & Pierce, P.L.C.; Anthony G. Fussner

(57) ABSTRACT

Exemplary embodiments are disclosed of systems, methods, and technologies for the management, monitoring, improvement, and research of medicine and health in off-Earth, non-Earth, and specialty environments.

31 Claims, 43 Drawing Sheets

Related U.S. Application Data

18/090,047 is a continuation-in-part of application No. 17/882,061, filed on Aug. 5, 2022, now Pat. No. 12,289,654, and a continuation-in-part of application No. 17/861,559, filed on Jul. 11, 2022, now Pat. No. 12,342,240, said application No. 17/903,419 is a continuation-in-part of application No. 17/861,559, filed on Jul. 11, 2022, now Pat. No. 12,342,240, said application No. 18/090,047 is a continuation-in-part of application No. 17/541,707, filed on Dec. 3, 2021, now Pat. No. 12,096,308, said application No. 17/903,419 is a continuation-in-part of application No. 17/541,707, filed on Dec. 3, 2021, now Pat. No. 12,096,308, said application No. 18/090,047 is a continuation-in-part of application No. 17/192,381, filed on Mar. 4, 2021, now Pat. No. 11,636,941, said application No. 17/541,707 is a continuation-in-part of application No. 17/192,381, filed on Mar. 4, 2021, now Pat. No. 11,636,941, said application No. 17/903,419 is a continuation-in-part of application No. 17/192,381, filed on Mar. 4, 2021, now Pat. No. 11,636,941, which is a continuation-in-part of application No. 17/104,136, filed on Nov. 25, 2020, now Pat. No. 11,412,353, said application No. 17/882,061 is a continuation of application No. 17/104,136, filed on Nov. 25, 2020, now Pat. No. 11,412,353, said application No. 17/541,707 is a continuation-in-part of application No. 17/104,136, filed on Nov. 25, 2020, now Pat. No. 11,412,353, and a continuation-in-part of application No. 16/700,601, filed on Dec. 2, 2019, now Pat. No. 11,388,546, said application No. 17/861,559 is a continuation-in-part of application No. 16/700,601, filed on Dec. 2, 2019, now Pat. No. 11,388,546, said application No. 17/104,136 is a continuation-in-part of application No. 16/654,708, filed on Oct. 16, 2019, now Pat. No. 10,853,897, which is a continuation-in-part of application No. 16/516,822, filed on Jul. 19, 2019, now Pat. No. 10,497,242, and a continuation-in-part of application No. 15/840,762, filed on Dec. 13, 2017, now Pat. No. 10,477,342, said application No. 16/700,601 is a continuation of application No. 15/840,775, filed on Dec. 13, 2017, now Pat. No. 10,555,112, said application No. 16/516,822 is a continuation-in-part of application No. 15/840,762, filed on Dec. 13, 2017, now Pat. No. 10,477,342.

(60) Provisional application No. 63/460,523, filed on Apr. 19, 2023, provisional application No. 63/441,569, filed on Jan. 27, 2023, provisional application No. 63/344,976, filed on May 23, 2022, provisional application No. 63/316,277, filed on Mar. 3, 2022, provisional application No. 63/294,815, filed on Dec. 29, 2021, provisional application No. 63/275,300, filed on Nov. 3, 2021, provisional application No. 63/120,834, filed on Dec. 3, 2020, provisional application No. 63/011,949, filed on Apr. 17, 2020, provisional application No. 62/986,382, filed on Mar. 6, 2020, provisional application No. 62/746,330, filed on Oct. 16, 2018, provisional application No. 62/701,252, filed on Jul. 20, 2018, provisional application No. 62/480,206, filed on Mar. 31, 2017, provisional application No. 62/435,042, filed on Dec. 15, 2016.

(56) References Cited

U.S. PATENT DOCUMENTS

| | | | | |
|---|---|---|---|---|
| 5,980,447 | A | 11/1999 | Trudeau | |
| 6,039,688 | A | 3/2000 | Douglas et al. | |
| 6,425,764 | B1 | 7/2002 | Lamson | |
| 6,437,696 | B1 | 8/2002 | Lemelson et al. | |
| 6,639,516 | B1 | 10/2003 | Copley | |
| 7,219,368 | B2 | 5/2007 | Juels et al. | |
| 7,343,365 | B2 | 3/2008 | Farnham et al. | |
| 7,633,076 | B2 | 12/2009 | Huppi et al. | |
| 7,908,645 | B2 | 3/2011 | Varghese et al. | |
| 8,301,767 | B1 | 10/2012 | Davis et al. | |
| 8,798,593 | B2 | 8/2014 | Haney | |
| 8,862,393 | B2 | 10/2014 | Zhou et al. | |
| 9,017,078 | B2 | 4/2015 | Gross | |
| 9,104,788 | B2 | 8/2015 | Friedman et al. | |
| 9,288,196 | B2 | 3/2016 | Shuster | |
| 9,341,050 | B2 | 5/2016 | Al-Buraik | |
| 9,917,824 | B2 | 3/2018 | Britt | |
| 10,114,351 | B2 | 10/2018 | Fadell et al. | |
| 10,218,844 | B1 | 2/2019 | Edwards et al. | |
| 10,395,221 | B1 | 8/2019 | Price et al. | |
| 10,477,342 | B2 | 11/2019 | Williams | |
| 10,497,242 | B2 | 12/2019 | Williams | |
| 10,555,112 | B2 | 2/2020 | Williams | |
| 10,853,897 | B2 | 12/2020 | Williams | |
| 10,861,307 | B2 | 12/2020 | Williams | |
| 11,412,353 | B2 | 8/2022 | Williams et al. | |
| 11,599,953 | B1 | 3/2023 | McNair | |
| 2003/0199780 | A1* | 10/2003 | Page | A61B 5/0878 600/538 |
| 2005/0068169 | A1 | 3/2005 | Copley et al. | |
| 2006/0004680 | A1 | 1/2006 | Robarts et al. | |
| 2008/0146193 | A1 | 6/2008 | Bentley et al. | |
| 2009/0099985 | A1 | 4/2009 | Tesauro et al. | |
| 2009/0265326 | A1 | 10/2009 | Lehrman et al. | |
| 2010/0076968 | A1 | 3/2010 | Boyns et al. | |
| 2010/0125563 | A1 | 5/2010 | Nair et al. | |
| 2010/0227629 | A1 | 9/2010 | Cook et al. | |
| 2011/0022540 | A1 | 1/2011 | Stern et al. | |
| 2012/0083911 | A1 | 4/2012 | Louboutin et al. | |
| 2012/0135756 | A1 | 5/2012 | Rosso et al. | |
| 2012/0268269 | A1 | 10/2012 | Doyle | |
| 2012/0308970 | A1 | 12/2012 | Gillespie et al. | |
| 2013/0145441 | A1 | 6/2013 | Mujumdar et al. | |
| 2013/0179955 | A1 | 7/2013 | Bekker et al. | |
| 2013/0216989 | A1 | 8/2013 | Cuthbert | |
| 2014/0094192 | A1 | 4/2014 | Annett | |
| 2014/0142729 | A1 | 5/2014 | Lobb et al. | |
| 2014/0192325 | A1 | 7/2014 | Klin et al. | |
| 2014/0248904 | A1 | 9/2014 | Meredith et al. | |
| 2014/0278212 | A1 | 9/2014 | Torgersrud et al. | |
| 2014/0322676 | A1 | 10/2014 | Raman | |
| 2014/0331278 | A1 | 11/2014 | Tkachev | |
| 2014/0347265 | A1 | 11/2014 | Aimone et al. | |
| 2015/0009028 | A1 | 1/2015 | Gehrke et al. | |
| 2015/0065822 | A1 | 3/2015 | Blenkush | |
| 2015/0230086 | A1 | 8/2015 | Bentley et al. | |
| 2015/0366518 | A1* | 12/2015 | Sampson | A61B 5/721 600/509 |
| 2015/0367230 | A1 | 12/2015 | Bradford et al. | |
| 2016/0019382 | A1 | 1/2016 | Chan et al. | |
| 2016/0063532 | A1 | 3/2016 | Loeb et al. | |
| 2016/0066864 | A1 | 3/2016 | Frieder et al. | |
| 2016/0078781 | A1 | 3/2016 | McCartney | |
| 2016/0140353 | A1 | 5/2016 | Biswas et al. | |
| 2016/0140404 | A1 | 5/2016 | Rosen | |
| 2016/0260135 | A1 | 9/2016 | Zomet et al. | |
| 2016/0330601 | A1 | 11/2016 | Srivastava | |
| 2016/0381502 | A1 | 12/2016 | Kern, Jr. et al. | |
| 2017/0020442 | A1 | 1/2017 | Flitsch et al. | |
| 2017/0134832 | A1 | 5/2017 | Briggs et al. | |
| 2017/0276489 | A1 | 9/2017 | Breed | |
| 2017/0365182 | A1 | 12/2017 | Lavi et al. | |
| 2018/0103341 | A1 | 4/2018 | Moiyallah, Jr. et al. | |
| 2018/0140241 | A1 | 5/2018 | Hamalainen et al. | |
| 2018/0165476 | A1 | 6/2018 | Carey et al. | |

(56) References Cited

U.S. PATENT DOCUMENTS

| | | | | |
|---|---|---|---|---|
| 2018/0166176 | A1 | 6/2018 | Flippen et al. | |
| 2018/0173866 | A1 | 6/2018 | Williams | |
| 2018/0176727 | A1 | 6/2018 | Williams | |
| 2018/0240544 | A1 | 8/2018 | Lo et al. | |
| 2019/0101985 | A1 | 4/2019 | Sajda et al. | |
| 2019/0122258 | A1 | 4/2019 | Bramberger et al. | |
| 2019/0340906 | A1 | 11/2019 | Williams | |
| 2020/0051189 | A1 | 2/2020 | Williams | |
| 2020/0084451 | A1 | 3/2020 | Wahadaniah et al. | |
| 2020/0086133 | A1* | 3/2020 | Wang | A61B 5/0006 |
| 2020/0107155 | A1 | 4/2020 | Williams | |
| 2020/0160223 | A1 | 5/2020 | McGavran et al. | |
| 2021/0035675 | A1 | 2/2021 | Shantharam | |
| 2021/0112064 | A1 | 4/2021 | Losseva et al. | |
| 2021/0202067 | A1 | 7/2021 | Williams et al. | |
| 2021/0391089 | A1 | 12/2021 | Eswara et al. | |
| 2022/0086649 | A1 | 3/2022 | Korenwaitz et al. | |
| 2022/0116736 | A1 | 4/2022 | Williams et al. | |
| 2022/0353632 | A1 | 11/2022 | Williams | |
| 2022/0386080 | A1 | 12/2022 | Williams et al. | |
| 2023/0092647 | A1* | 3/2023 | Mundell | A01K 15/02 119/712 |

FOREIGN PATENT DOCUMENTS

| | | | |
|---|---|---|---|
| KR | 100692803 | B1 | 3/2007 |
| KR | 101581772 | B1 | 1/2016 |
| KR | 1020160046690 | A | 4/2016 |
| WO | WO-2015171702 | A1 | 11/2015 |
| WO | WO-2016178617 | A1 | 11/2016 |
| WO | WO-2018112047 | A2 | 6/2018 |
| WO | WO-2018112048 | A1 | 6/2018 |

OTHER PUBLICATIONS

Carise et al., Development a National Addiction Treatment Information System: An Introduction to the Drug Evaluation Network System; Journal of Substance Abuse Treatment; 1999; Abstract; 2 pages.

Cartreine, PhD., et al., A Roadmap to Computer-Based Psychotherapy in the United States, Copyright 2010 President and Fellows of Harvard College; 16 pages.

Conquer Your Alcoholism, conqueryouraddiction.com, accessed Dec. 7, 2017 3 pages.

D. H. Williams, How to Conquer your Alcoholism: A Complete and Useable Program and Reference Guide to Getting & Staying Sober; Jan. 16, 2015; 654 pages; (1 page attached).

Dackis, et al., Neurobiology of addiction: treatment and public policy ramifications; Nature Neuroscience vol. 8, No. 11, Nov. 2005; 1 page.

DiClemente, Ph.D., et al., Readiness and Stages of Change in Addiction Treatment, *The American Journal on Addictions*, Coypright 2004; 13: 103-119.

Fussel, Sidney; The Next Data Mine is Your Bedroom, Nov. 17, 2018, 6 pages.

Gainsbury, A systematic Review of Internet-based therapy for the Treatment of Addictions, Southern Cross University, 2011, vol. 31, No. 3, pp. 490-498.

Gotham, Diffusion of mental health and substance abuse treatments; development, dissimentation, and implementation; 2004; absract; 1 page.

Gravenhorst et al., Mobile Phones as Medical Devices in Mental Disorder Treatment: an Overview; Personal and Ubiquitious Computing, 2015, abstract: 2 pages.

Gustafson, Ph.D., et al., Explicating an Evidence-Based, Theoretically Informed, Mobile Technology-Based System to Improve Outcomes for People in Recovery for Alcohol Dependence; NIH Public access, Author Manuscript, Subst Use Misuse. 2011; 46(1):96-111. doi:10.3109/10826084.2011.521413.

Heron et al., Ecological Momentary Interventions: Incorporating Mobile Technology in to PSychosocial and Health Behavior Treatments; HHS Public Access; Author Manuscript; Published on-line 2009; Br J Health Psychol. Feb. 2010: 15(Pt 1): 22 pages.

International Search Report and Written Opinion for PCT/US2017/066134 filed Dec. 13, 2017 which claims priority to the same parent application as the instant application, dated Mar. 29, 2018, 11 pages.

International Search Report and Written Opinion for PCT/US2017/066136 filed Dec. 13, 2017 which claims priority to the same parent application as the instant application, dated Apr. 9, 2018, 15 pages.

Kaplan et al., Bringing the Laboratory and Clinic to the Community: mobile technologies for health promotion and disease prevention; Annual Review of Psychology; 2013; abstract, 2 pages.

Kelly, Laura; Teen suicide rate suddenly arises with heavy use of smartphones, social media, The Washington Times—Tuesday, Nov. 14, 2017; https://www.washingtontimes.com/news/2017/nov/14/teen-suicides-rise-with-smartphone; 4 pages.

Lee et al., The SAMS: Smartphone addicion mangement System and Verification; Journal of Medical Systems; 2014, abstract; 2 pages.

Luxton et al., mHealth for Mental Health: Integrating Smartphone Technology in Behavioral Healthcare, Professional Psychology: Research and Practice, 2011, vol. 42, No. 6. pp. 505-512.

McClure et al., Utilization of Communication Technology by Patients Enrolled in Substance Abuse Treatment, NIH Public Access, Author Manuscript, Drug Alcohol Depend. Apr. 1, 2013: 129(1-2): 145-150. doi:10.1016/j.drugalcdep.2012.10.003.

McKay et al., Conceptual, methodological, and analytical issues in the study of relapse, Copyright 2005, www.sciencedirect.com, 19 pages.

McLellan, et al., Reconsidering the evaluation of addiction treatment: from retrospective follow-up to concurrent recovery monitoring; Copyright 2005 Society for the Study of Addiction; Addiction, 100, 447-458.

Stacy et al., Implicit Cognition and Addiction: A Tool for Explaining Paradoxical Behavior; HHS Public access, Author Manuscript, Ann. Rev. Clin. Psychol. 2010: 6: 22 pages.

The Conquer Quiz, Test for Alcoholism, conqueryouraddiction.com, accessed Dec. 7, 2017, 2 pages.

Gustafson et al., An E-Health Solution for People with Alcohol Problems; ARCR/Alcohol Research Current review; 2011; 33(4): pp. 327-337.

Lee et al., The SAMS: Smartphone addicion management System and Verification; Journal of Medical Systems; 2014, abstract; 2 pages.

Blockchain—Wikipedia; https://en.wikipediaorg/wiki/Blockchain; Feb. 28, 2020; 19 pages.

Proof-of-Work, Explained; https://cointelegraph.com; 2013-2020; 6 pages.

USPTO Nonfinal Office Action for U.S. Appl. No. 17/192,381 that claims priority to the same parent application as the instant application; dated Aug. 4, 2022, 62 pages.

D. H. Williams, How to Conquer Your Alcoholism—Made Simple! The Practical Way to Get and Stay Sober; paperback—Aug. 3, 2017; 259 pages; 1 page attached.

Ayyar, Ranjani, One Heart on YuppTV, Chennai girl makes it to Forbes list with tool to combat addictions, https://timesofindia.indiatimes/city/chennai/chennai-girl-makes-it-to-forbes-list-with . . . , Nov. 16, 2017, 42 pages.

Davis, Jr. et al.; Chaotic solar cycles modulate the incidence and severity of mental illness; Augusta Mental Health Institute; 2003; two pages.

* cited by examiner

- ASSESS TRIGGER/RELAPSE RISK
- LEARN/MODIFY RISK ALGORITHMS

DETERMINE/ PREDICT TRIGGER RELAPSE RISK

- REPRESENTS MAJOR STEP, PROCESS, OR OPERATION

A

B

| ADDICT #243 TRIGGERS | RISK PRIORITY/ SEVERITY (H/M/L, 1-10) (10 HIGHEST) | LOCATION/CONTEXT ELEMENTS/SENSORS MONITORED/ANALYZED | RISK FORMULA; RISK ACTION CLASSIFICATION |
|---|---|---|---|
| BOREDOM | RP = HIGH (RP SCORE=9) | A.ADDICT STAYS IN ONE PLACE MORE THAN X HOURS (EXCEPT SLEEP HOURS) = A=X-2; ZERO LOWEST VALUE)<br>B.LOW BLOOD PRESSURE (BELOW 100/70 (YES/NO = 1/0)<br>C.BOREDOM BUTTON PUSHED = 10) | RISK = RP/5*(A +(B*2)+C)<br>RISK CLASS: >=6 THEN TRIGGER BASED; <6 THEN RESOURCE-BASED |
| DEPRESSION | MED (5-) | A.SENSOR 1 VALUE<br>B.SENSOR 2 VALUE<br>C.DEPRESSION BUTTON PUSHED =10 | RISK = A +(B*2)+C/RP<br>RISK CLASS: TRIGGER-BASED (DEFAULT) |
| INSOMNIA | LOW (3) | A.UNUSUAL NIGHT-TIME MOVEMENT<br>B.HIGH RESTLESS SLEEP SCORES(E.G. VIA SLEEP NUMBER BED) | RISK = A +(B*3) – RP<br>RISK CLASS: ACTION CATEGORY BASED |
| YELLING/ CONFLICT | MED (6) | A. LOUD NOISES DETECTED<br>B. DISTRESS DETECTED (ELEVATED BLOOD PRESSURE RAPID RISE IN SKIN TEMPERATURE) | RISK = A +(B*4) + RP<br>RISK CLASS: INTERFACE-BASED |

C

NOTE/LEGEND

INDICATES EMERGENCY-TYPE SITUATION OR PROCESS

MODIFY FREQUENCY AND SCOPE OF MONITORING

D

FIG. 5

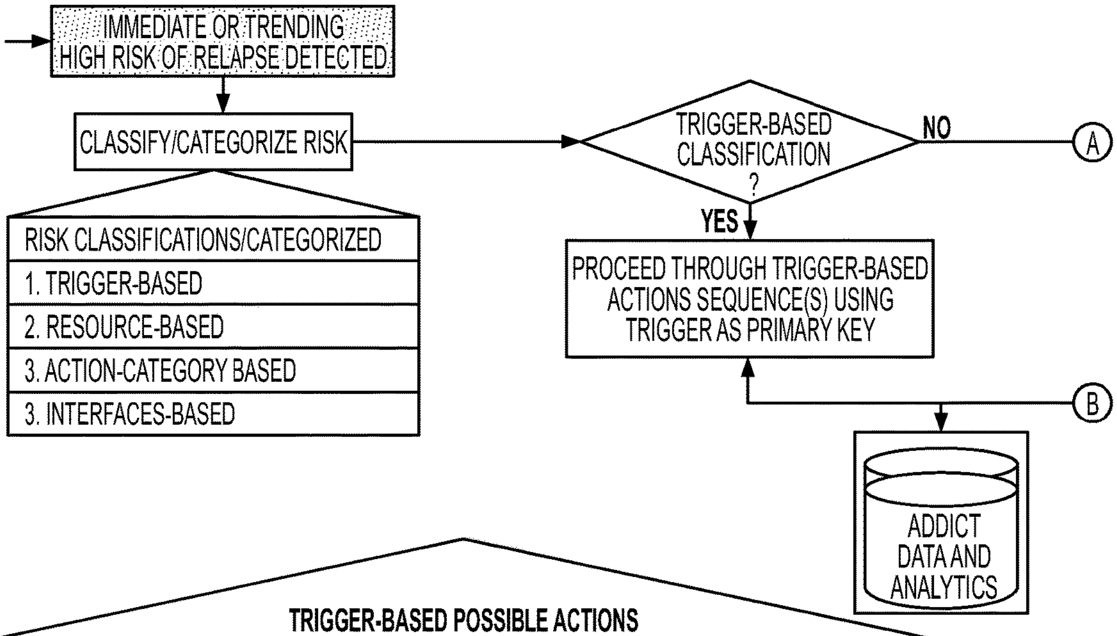

TRIGGER-BASED POSSIBLE ACTIONS

| ADDICT 421 MAJOR TRIGGERS | POSSIBLE ACTIONS (PREFERRED SEQUENCE & WHETHER WAITING OR CUMULATIVE) | SUPPORT NETWORK CONTACT(S) | PREFERRED INTERFACE(S) | ADDICT RELATED TRIGGERS (AND ACTION REQ'S) |
|---|---|---|---|---|
| BOREDOM | 1.PROMPT HOBBY USAGE LIST DEPENDING ON CONTEXT(LINK TO CONTEXT-BASED SECONDARY ACTIONS)<br>2.PROMPT (AND AUTO-CONNECT VIA NETFLIX) "BINGE" SHOWS BASED ON PREFERENCES. STREAM TO NEAREST DEVICE (W); INVITE FRIENDS TO WATCH (CONTEXT: HOME) | 1.HOBBY X - CONTACT 12;<br>2.HOBBY Y – CONTACT 4<br>3. BINGING – GROUP C | • IN PERSON<br>• LIVE | • LONELINESS (ACTION REQUIRES SUPPORT PERSON ON WEEKENDS) |
| DISORDER | 1.CLEAN!<br>2.MEDITATION<br>3.CALL CLEANING LADY<br>4.CONTACT THERAPIST/DOCTOR | 1. CLEANING LADY X<br>2. DR. D | 1. (PRE-RECORDED) VISUAL REMINDERS, MEDIATION MESSAGES<br>2.AUTOMATIC SCHEDULING | • DEPRESSION<br>• KIDS/ CHILDREN<br>• NOISE (ACTION REQUIRES LOW NOISE ON WEEKENDS) |
| FRUSTRATION | 1.CALL MOM<br>2.INITIATE MOM "MEDITATION MESSAGE" (VIA BEST AVAILABLE "HUMAN" I/F, E.G VOICE SYNTHESIS, VIDEO MESSAGE, HOLOGRAM, ETC.)<br>3.PLAY METALLICA<br>4.EXERCISE (RUN) | 1. MOTHER<br>2. SISTER<br>3. FRIEND A | 1)VIDEO CALL/HOLOGRAM<br>2)RECORDED VIDEO/HOLOGRAM<br>3)90$ VOLUME, BASS LEVELS<br>• FALLBACK: VOICE CALL, SMS/TEXT | • ANGER (ACTION REQUIRES CALM ENVIRONMENTS AT NIGHT)<br>• JOB<br>• POWELESSSNESS |

C

FIG. 7

- IDENTIFY/REFINE POSSIBLE ACTION(S)
- IDENTIFY/REFINE POSSIBLE RESOURCE(S)
- IDENTIFY/REFINE POSSIBLE INTERFACE(S)

RESOURCE-BASED ACTION PARAMETERS, W/ SUPPORTED ACTIONS & INTERFACE REQS (D)

| SUPPORT RESOURCE | LOGISTICAL CONSTRAINTS, PREFERENCES | SUPPORTED ACTION(S) (PREFERRED SEQUENCE) | INTERFACE REQUIREMENTS / PREFERRED INTERFACE (S) |
|---|---|---|---|
| SPONSOR 1 | NO WEEKENDS | 1. LIVE, FACE-TO-FACE VISITS WITHIN 30 MINUTES OF CURRENT LOCATION | • FACE-TO-FACE<br>• HOLOGRAM<br>• PHONE CALL |
| MEDICAL PROFESSIONAL 3 (DR. D) | • AFTER 5PM<br>• TRIGGER(S):ANXIETY, DISORDER ONLY<br>• RELAPSE RISK >=8 | 1. PROTOCOLS A, D | 1. PHONE CALL ONLY |
| MOTHER | NONE | 1. FACE-TO-FACE MEETING<br>2. LIVE VIDEO/CALL<br>2. SEND MOM "MEDITATION MESSAGE" (VIA BEST "HUMAN" I/F, E.G. HOLOGRAM VOICE SYNTHESIS, VIDEO MESSAGE ETC.) | 1. LIVE VISIT<br>2. HOLOGRAM<br>3. SKYPE<br>4. PHONE CALL<br>4. VIDEO-BASED I/F IF LIVE NOT POSSIBLE |
| PROBATION OFFICER | ONLY IF RELAPSE IS EMERGENCY AND MEETS CONDITIONS OF PROBATION | 1. AUTO GENERATE CALL CONNECTING PROBATION OFFICER TO ADDICT CONTROLLER OFFICER<br>2. EVALUATE FURTHER OPTIONS UNDER PROTOCOLS E, F, G | 1. ANY |
| BOWLING @BRUNSWICK LANES (5 LOCATIONS) | MONDAY-SATURDAY 9AM – 11PM, SUNDAY 10AM-6 PM | 1. PROMPT FOR ANY HOBBY USAGE REQUIREMENT IN BAD WEATHER, OR BOREDOM IN GENERAL.<br>2. BRUNSWICK LOCATION B GOOD FOR SPORTS VIEWING-RELATED ACTIONS | 1. IN PERSON<br>2. USE WII VIDEO GAME AS A OPTION IF NO SUPPORT PERSONS AVAILABLE |
| SOCIAL MEDIA C | ALL MEMBERS OF GROUP C HAVE BEEN THROUGH PRIVACY PROTOCOL TRAINING AND VETTING | 1. PROMPT POSTS FROM ADDICT TO GROUP X FOR IDENTIFIED TRIGGER(S)<br>2. GENERATE AUTOMATED POSTS REQUESTING HELP; ROUTE RESPONSES TO ADDICT | POSTS AUTOMATICALLY DELETED AFTER 5 MINUTES |

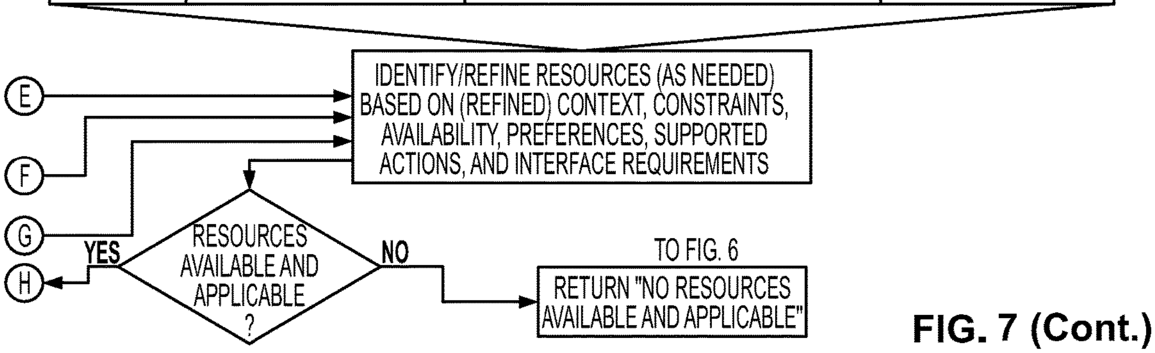

FIG. 7 (Cont.)

POSSIBLE ACTION – ADDICTION COMMUNITY MEETING

MEETING CRITERIA

| PERSON | SEVERITY THRESHOLD | MEETING CONTEXT CONSTRAINTS/LIMITATIONS | LOCATION LIMITATION |
|---|---|---|---|
| ADDICT 1 | HIGH (IMMEDIATE OR TRENDING) | 1.WOMEN-ONLY<br>2.ANXIETY, DEPRESSION-THEMED MEETINGS PREFERRED<br>3.AFTER 5 PM WEEKDAYS<br>4.PARTICULARLY INTERESTED IN ANXIETY-DEPRESSION DUAL TRIGGER MEETINGS | < 5 MILES CURRENT |
| SUPPORT PERSON 5 | MEDIUM OR ABOVE (IMMEDIATE OR TRENDING) | 1.CLOSED MEETINGS<br>2.HATES COFFEE | < 15 MILES CURRENT OR WITHIN 30 MINUTES |
| ADDICT 26 | MEDIUM OR ABOVE (IMMEDIATE ONLY) | 1.ONLY WHEN OUT-OF-TOWN (OUTSIDE OF HOME/WORK GEOFENCE)<br>2.OPEN, CLOSED MEETINGS | <10 MILES WITHIN 2 HOURS |
| ADDICT 62 | ANYTIME | 1. WHEN DRIVING<br>2.WHEN SPOUSE NOT NEARBY | BETWEEN 20 AND 50 MILES FROM HOME |

FLASH MEETING POTENTIAL SITES (COMMUNITY MEETING DB)

| POTENTIAL MEETING SITE | DESCRIPTION | CONSTRAINTS/ LIMITATIONS | COORDINATOR |
|---|---|---|---|
| X1, Y1 | STARBUCKS, CORNER OF LINDBERGH AND WALLEY STREETS | 1.STARBUCKS HOURS (LINK)(<br>2.NO MORE THAN 4 PEOPLE<br>3.COFFEE-DRINKERS PREFERRED | ADDICT 53 (LINK) |
| X3, Y3 | MISSOURI BAPTIST CHURCH (WEBSTER GROVES) | 1.ANYTIME EXCEPT SUNDAY<br>2.PROVIDE KEY CODE TO NEAREST INDIVIDUAL; CYCLE CODE AFTER MEETING (LINK) | MEDICAL PROFESSIONAL 5 (LINK) |
| X7, Y7, Z7 | 123 MAIN STREET, CITY HALL BUILDING, FLOOR 3, ROOM 312 | 1.PUBLIC ACCESS HOURS (LINK)<br>2.SECURITY GUARD NEEDS 30 MINUTE LEAD TIME (LINK) | FACILITY MANAGER'S OFFICE (LINK) |
| VIRTUAL 9 | ANYTIME | 1.NONE | TRIGGERMEETI-NG.COM COORDINATORS |

FIG. 7A

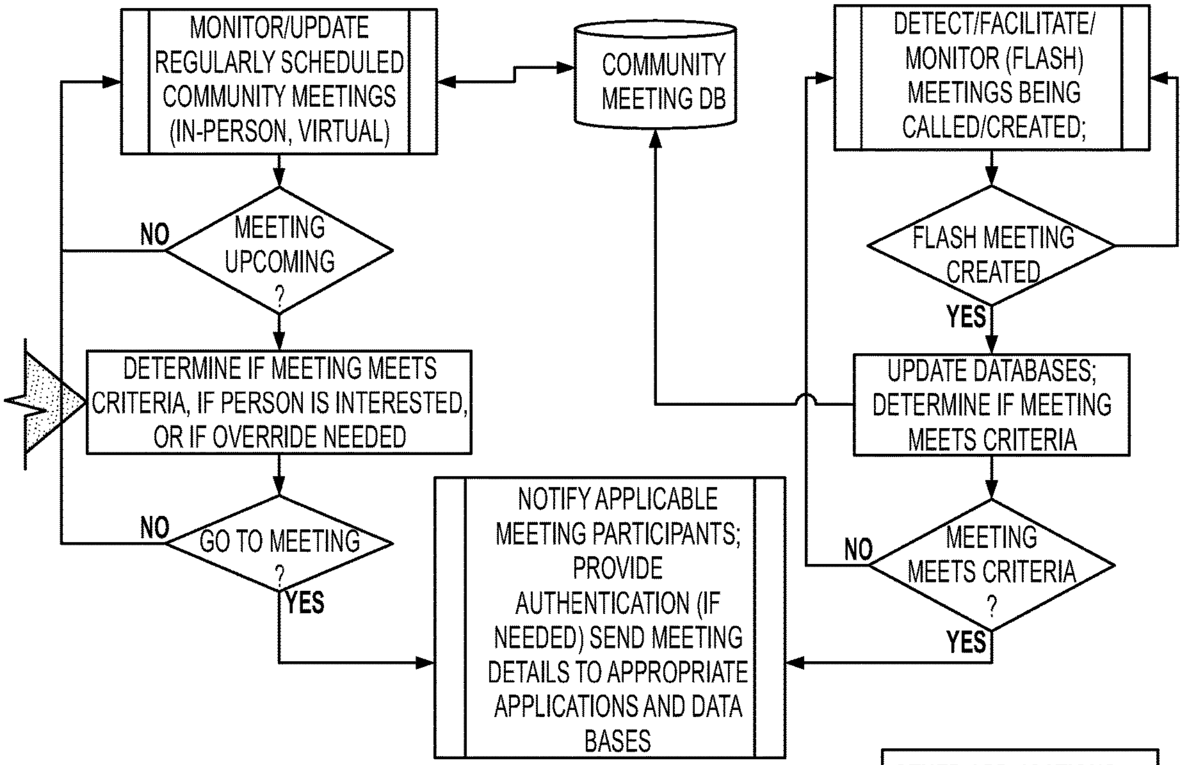

STANDING MEETINGS (COMMUNITY MEETING DB)

| MEETING | LOCATION | DESCRIPTION | CONSTRAINTS /FOCUS |
|---|---|---|---|
| M-W-F 7:30 PM | MISSOURI BAPTIST CHURCH | IN-PERSON; ALCOHOLISM; NEW LIFE GROUP; BIG BOOK | WOMEN ONLY |
| SATURDAY 6PM | MISSOURI BAPTIST CHURCH (WEBSTER GROVES) | 1.IN PERSON; NARCOTICS ADDICTION<br>2.PROVIDE KEY CODE TO NEAREST INDIVIDUAL; CYCLE CODE AFTER MEETING (LINK) | YOUTH |
| TUESDAY THURSDAY EXCEPT NEW YEARS EVE | 123 MAIN STREET, CITY HALL BUILDING, FLOOR 3, ROOM 312 | 1.GENERAL ADDICTION, WITH FOCUS ON MENTAL DISORERS AND DUAL DIAGNSOSIS | ANXIETY/ DEPRESSION FOCUS |
| DAILY 4 PM | VIRTUAL; WWW.GAMBLERS ANON/DAILYMEET-ING | 1.ONLINE GAMBLING ADDICTION; ALL TRIGGER TYPES | NO LIMITATIONS; BIG BOOK FOCUS |

| OTHER APPLICATIONS AND DATABASES |
|---|
| NAVIGATION (DIRECTIONS TO MEETING) |
| FAMILY TRACKING (TO ALERT FAMILY ABOUT DETOUR, WHERE/WHEN ADDICT WILL BE THERE) |
| REWARDS TRACKING |
| LEARNING MODULES (TO TRACK IMPULSE BEHAVIORS, ETC.) |

FIG. 7A (Cont.)

IDENTIFY, IMPLEMENT BEST INTERFACE FOR ACTION

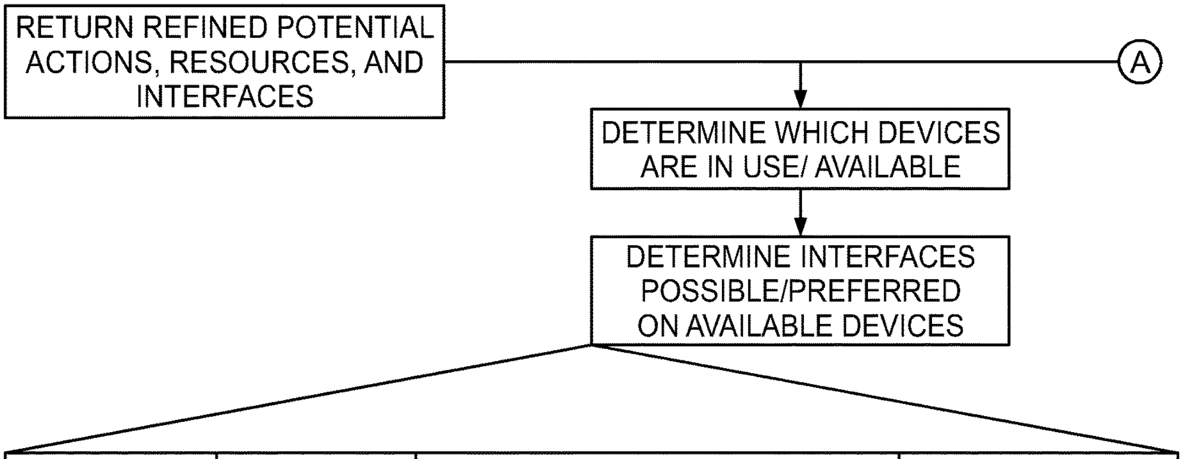

| ADDICT J. SMITH DEVICES | CONTEXTS | INTERFACE OR SUB-INTERFACE PRIORITIES | CONSTRAINTS, ISSUES, SPECIAL CONDITIONS |
|---|---|---|---|
| PHONE 1 | ALL | 1.LIVE HOLOGRAM *IF PHONE I/F WITH HEADS UP DISPLAY/GOOGLE GLASSES ETC., VIDEO<br>2.LIVE VOICE<br>3.RECORDED HOLOGRAM, VIDEO | HOLOGRAM ONLY IF IN PRIVATE SETTING OR HUDS IN USE |
| SNAPCHAT SPECTACLES / GOOGLE GLASSES/ VR/HUDS | ALL | 1.TEXT ONLY | INCOMING: NO PRIVATE VIDEO (E.G. RESTROOMS); |
| CAR 1 SYSTEM | NON-RELAPSE AND/OR RISK < 8 | 1.DETECT IF ADDICT IS IN DRIVER OR NON-PASSENDGER SEATING. IF DRIVER SEE IF IN AUTOMATIC DRIVER MODE | CHILDREN, PET HOLOGRAMS IN PASSENGER SEAT IF POSSIBLE |
| IMPLANT 1 | AVERSION ACTIONS ONLY | 1.HEAT<br>2.STING<br>3.SOUND | • NOT DRIVING<br>• IN PRIVATE<br>• ONE-WAY ONLY |
| HOME SYSTEM | NO 3RD PARTIES PRESENT | 1.PROMPT HOBBY USAGE<br>2.PROMPT (AND AUTO-CONNECT VIA NETFLIX) "BINGE" SHOWS BASED ON PREFERENCES. STREAM TO NEAREST DEVICE | IMPLEMENT "TRACKING" SENSORS TO FOLLOW ADDICT AROUND HOME |

FIG. 8

ADDICT BEHAVIOR REWARDS TRACKING, ANALYTICS, AND ALLOCATION/AWARDS

| ADDICT REWARDS BEHAVIOR TABLE | PTS |
|---|---|
| AVOID LOCATION X FOR Y DAYS | 3 |
| ATTEND AA-TYPE MEETING (IN PERSON) | 1 |
| "ATTEND" AA-TYPE MEETING (VIRTUAL) | 0.5 |
| ALCOHOL DETECTION (E.G. VIA SENSORS, SOCIAL MEDIA, ETC.) | -5 |
| "SAFELY" BUSY AT 7PM EACH NIGHT | 1 |
| SUPPORT NETWORK WEEKLY RATING GREATER/EQUAL TO 4 STARS | 2 |
| EXERCISE, HOBBY, MEDITATION, WALK (EACH 30 MINUTES, 5000 STEPS, ETC.) | 1 |
| NO INTERACTION WITH OTHERS IN A DAY (E.G. FOR LONELINESS DRINKING TRIGGER) | -1 |
| INTERACTION WITH "NEGATIVE" PERSONS (E.G. PEER PRESSURE DRINKING TRIGGER) | -2 |
| ************************************ | *** |
| JULY TO-DATE POINTS EARNED | 12 |
| AMAZON CREDITS (2=$5 OF EBOOKS) | 2 |
| GYM (4= GYM MO. SUBSCRIPTION CREDIT) | 3 |
| FREE PHONE/INTERNET (1 MO. - 10 CREDITS) | 1 |
| STARBUCKS COFFEE CREDTIS (2 PTS = 1 GRANDE | 2 |
| HOBBIES/LESSONS CREDITS (CRAFTSY.COM, UDMY.COM, TAKELESSONS.COM, ETC.) | 2 |
| TO BE ALLOCATED/USED - JULY<br>TO BE ALLOCATED/USED - TOTAL | 2<br>13 |

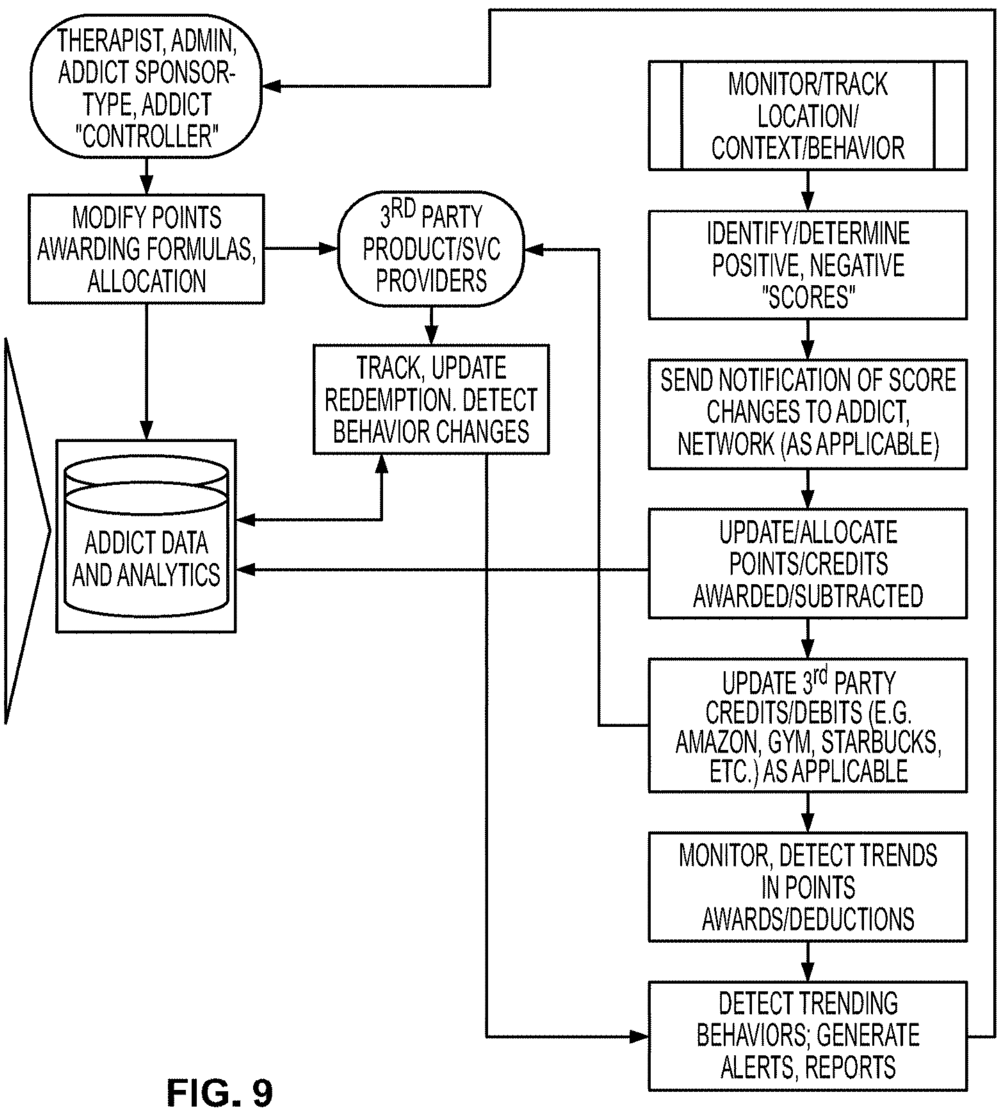

FIG. 9

LOCATION/CONTEXT-BASED PRIVACY AND SECURITY

LOCATION/CONTEXT-BASED VERIFICATION QUESTION EXAMPLES

- WHERE HAVE YOU BEEN IN THE LAST (WEEK, MONTH, YEAR, ETC.)?
- WHERE HAVE YOU BEEN WITH YOUR YOUNGEST DAUGHTER (TIMEFRAME)?
- WHERE HAVE YOU NOT BEEN IN THE LAST MONTH?
- PLEASE SELECT YOUR VACATION-RELATED IMAGES (TIMEFRAME OPTIONAL)?
- PLEASE SELECT IMAGES* THAT ARE FAMILY ACTIVITY-RELATED.
- PLEASE SELECT IMAGES OF LOCATION(S) WHERE YOU CURRENTLY RESIDE.
- PLEASE SELECT IMAGES OF LOCATION(S) WHERE YOU HAVE NEVER BEEN
- PLEASE SELECT VACATION IMAGES BETWEEN X AND Y DATES
- PLEASE SELECT PICTURES OF YOUR FIRST DAUGHTER'S WEDDING LOCALES (CHURCH, RECEPTION, HONEYMOON)

LOCATION/CONTEXT-BASED VERIFICATION ANSWER EXAMPLES

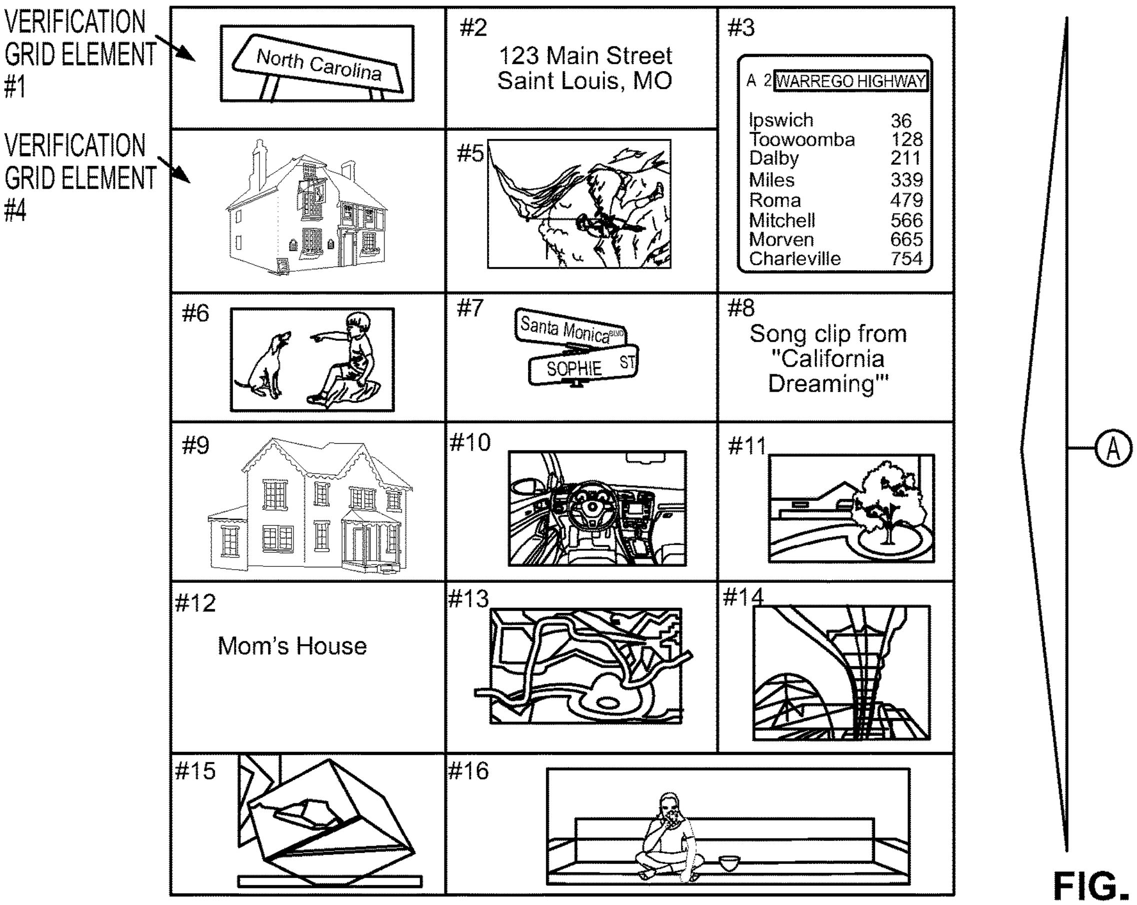

FIG. 11

| LOCATION/CONTEXT-BASED P/S MEMORY PROFILE |
|---|
| PRIORITY 1: HISTORICAL VACATION IMAGES (< 1 YEAR OLD; HAWAII, SKIING PREFERRED) |
| PR #2: ROAD SIGNS (NEAR MOTHER'S HOUSE) (NO TIME LIMIT) |
| PR #3 SONGS WITH LOCATIONS IN THEM (E.G. CALIFORNIA DREAMING, SWEET HOME ALABAMA, ETC.) |
| NO IMAGES FROM NORTH/SOUTH DAKOTA, BROTHER'S WEDDING |

JIGSAW PUZZLE LOCATION/CONTEXT-BASED SECURITY

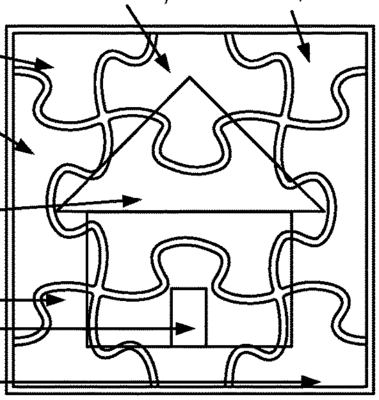

| GRID # | SOURCE (DEVICE, PROCESS, ETC.) |
|---|---|
| #1 | GEOFENCE EXCEPTION DATA FROM CAR 1/DEVICE B |
| #2 | LAT/LONG TO ADDRESS TRANSLATION OF IMAGE #4 |
| #3 | ALGORITHMIC DERIVATION AND GRAPHICAL IMAGE CREATION FROM LAT/LONG CENTERPOINT OF VACATION X (ALL DEVICES) |
| #4 | PICTURE OF MOM'S HOUSE (DEVICE A) |
| #5 | VACATION PHOTO (FROM PERSON C HELMET CAM) |
| #6 | PICTURE OF PET (WHO DIED IN 2002) AT HOME XYZ |
| #7 | GRAPHICAL/AUGMENTED REALITY SIMULATION DERIVED FROM DRIVERLESS CAR C LOCATION OR IMAGE CAPTURE |
| (A) #8 | AUDIO CLIP INDICATING VISIT TO CALIFORNIA IN TIMEFRAME P (MOBILE SOCIAL NETWORKING POST FROM FRIEND E |
| #9 | RANDOM LOCATION SAMPLE OF RETAIL "VISITS", WITH ADDRESS MATCHED WITH STORE NAME AND IMAGE PULLED FROM INTERNET |
| #10 | IMAGE TAKEN FROM CHILD DEVICE B, OR CAR SYSTEM A |
| #11 | SATELLITE IMAGE FROM GOOGLE MAPS OF HOMESTEAD A |
| #12 | COLLOQUIAL NAME OF MOM'S HOUSE (MANUALLY INPUT, TAGGED FROM PICTURE IN #4 OR FROM IMPORTED FROM FAMILYMAP APP (SEE RIGHT) |
| #13 | DELIBERATE DISTORTION/OBSTRUCTION OF CURRENT HOMESTEAD |
| #14 | 3D IMAGE OF SIX-FLAGS ROLLERCOASTER RIDE (3D DEVICE D) |
| #15 | A REVOLVING 3D IMAGE WITH DIFFERENT LOCATIONS (COMPOSITE) |
| #16 | VIDEO OF ME WATCHING TV IN LIVING ROOM (TV DEVICE 1) |

TIMEFRAME EXAMPLES

- SINCE D (DATE AND /OR TIME)
- LAST 24 HOURS
- LAST WEEK/MO/YR
- SINCE MOVE TO MOST RECENT ADDRESS
- BETWEEN X & Y
- NOT SINCE D OR BETWEEN X & Y

3RD PARTY APP IMPORT (AT&T FAMILYMAP EX.)

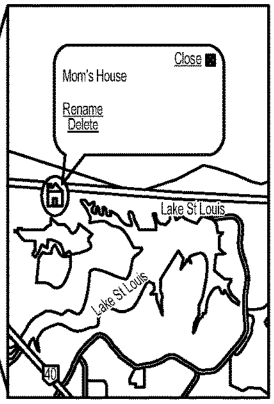

FIG. 11 (Cont.)

ADDICT JANE DOE –
LOCATION/CONTEXT PROTECTION
KEYS FOR JANUARY 6, 20XX

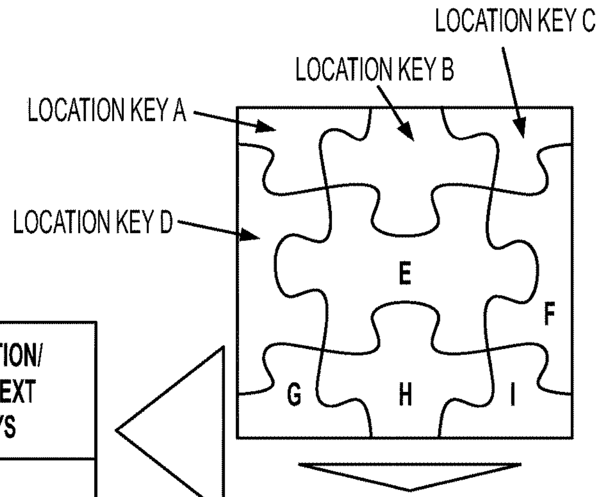

ADDICT JANE DOE -
CONTROLLER/MONITOR/ONC CALL
RESPONSIBILITY FOR JAN 6, 20XX

- Z1: 0:01 - 08:00: CONTROLLER 1
  (TWO 4 HOUR BLOCKS - LOCATION KEYS A & B)
- Z2: 08:01 - 17:00 CONTROLLER 2
  (THREE 3 HOUR DATA BLOCKS, C, D, E)
- Z3: 17:01 - 23:59 CONTROLLER 3
  (FOUR 105 MINUTE BLOCKS F, G, H, AND I)

Ⓐ EXAMPLE CONTROLLER KEYS FOR JANUARY 6TH

| CNTL # | LOCATION/ CONTEXT KEYS | LOCATION/ CONTEXT KEYS | LOCATION/ CONTEXT KEYS | LOCATION/ CONTEXT KEYS |
|---|---|---|---|---|
| 1 | A 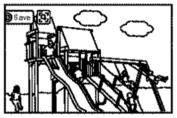 | B   | | |
| 2 | C 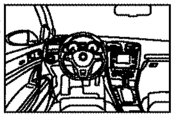 | D 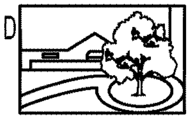 | E MISSOURI BOTANICAL GARDEN | |
| 3 | F GYM | G  | H  | I 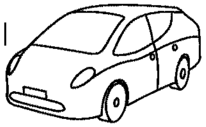 |

FIG. 12 (Cont. )

LOCATION/CONTEXT-BASED PRIVACY AND SECURITY (3D AND/ OR JIGSAW)

EXAMPLE CONTROLLER KEYS FOR JANUARY 6TH

| CONTROLLER | LOCATION / CONTEXT (TIME) ZONE | KEY | DEVICE (SOURCE, ACCESS) | IMAGE TYPE | TIME STAMP | LOCATION/ CONTEXT TAGS |
|---|---|---|---|---|---|---|
| 1 (ADDICT JANE DOE, SUPPORT LIST G, SUPPORT PERSON #4) | A (00:01 TO 04:00 CST) | 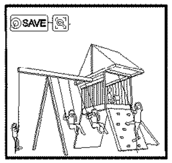  | S: IPHONE 2 A: PHOTOCAPABLE | 2D, VISUAL, PHOTO, COLOR, STRUCTURE, PERSONS | 7/3/20XX (SUMMER 20XX, 4TH OF JULY HOLIDAY) | OUTSIDE, SWINGSET, BACKYARD, PLAY, KIDS, SUMMER, NO RAIN, TREES, GRASS |
| 1 (ADDICT JANE DOE, SUPPORT LIST G, SUPPORT PERSON #4) | B (04:01 TO 08:01 CST) | 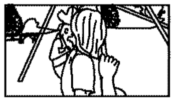 | S: GOOGLE GLASS; A: 3D ONLY | 3D, VISUAL, PHOTO/VIDEO, STRUCTURE, PERSONS | > 2 YEARS ROLLING | OUTSIDE, SWINGSET, PLAY, KIDS, SUMMER, OCEAN, BEACH, VACATION |
| 2 (ADDICT JANE DOE, SUPPORT LIST G, SUPPORT PERSON #6) | C (8:01 TO 11:01 AM CST 1/6); |  | S: IOT DEVICE X A: COMPUTER/LAPTOPS A OR D) | 2D, VISUAL ACCOMPANIED BY VOICE VERIFICATION; PERSON (1) | CURRENT (REALTIME STREAM, LESS THAN 1 HOUR HOLD) | SELFIE, NO BACKGROUND PICTURES, GLASSES; IN OFFICE/AT WORK |

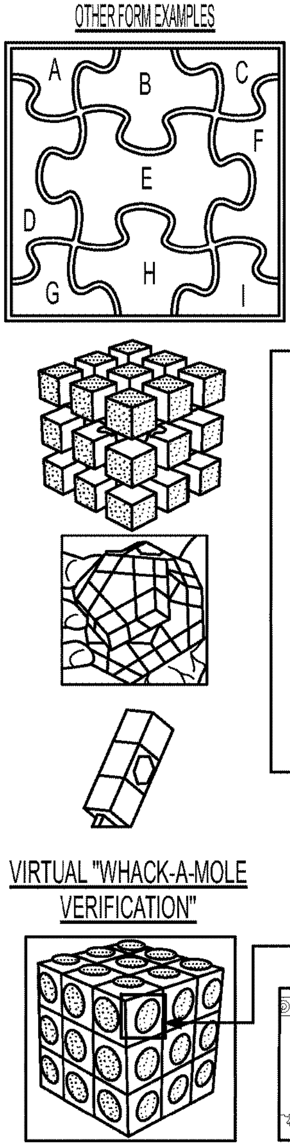

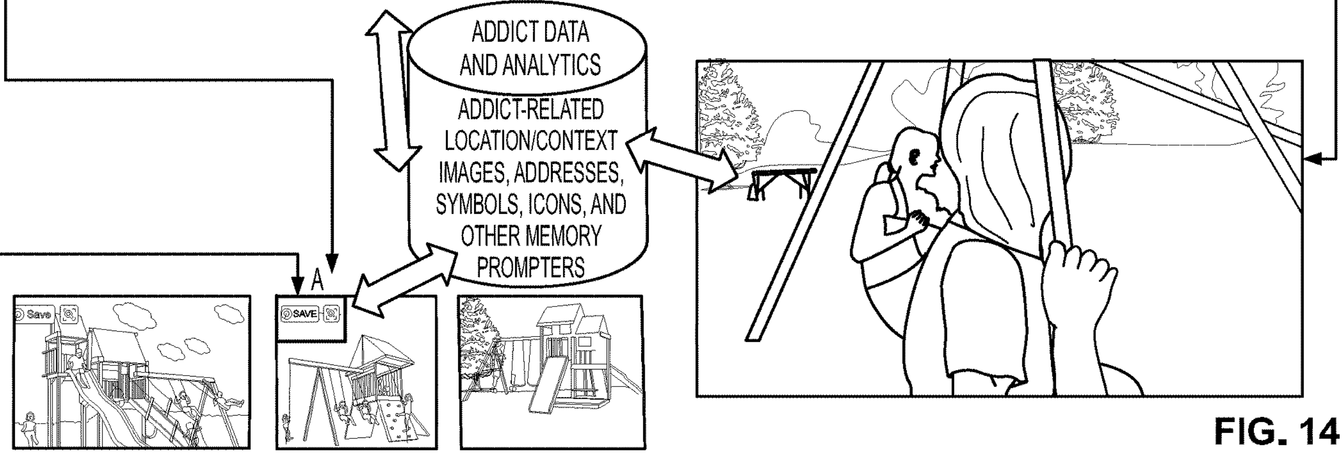

FIG. 14

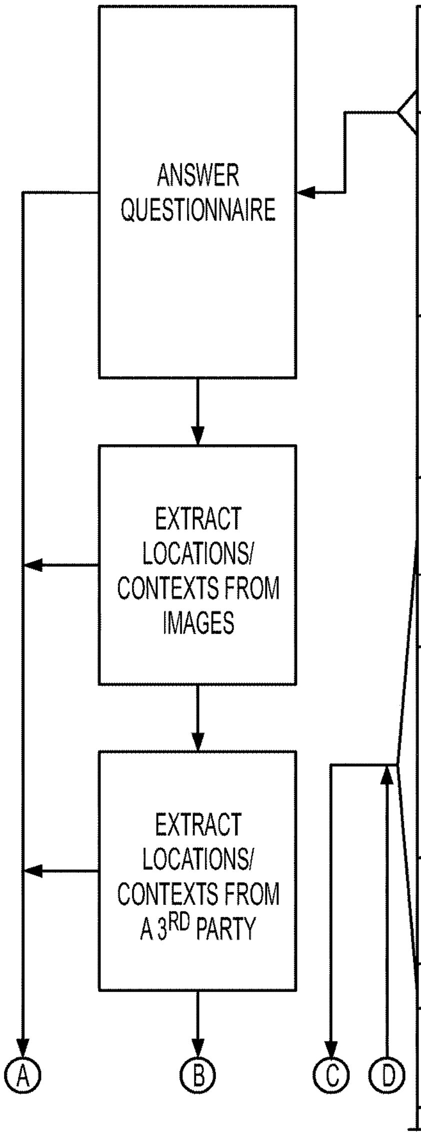

| TRIGGER LIST FOR ADDICT JOHN DOE | KEY SENSOR(S) READINGS, SYSTEMS, PARAMETERS, NEEDED TO MONITOR |
|---|---|
| ANGER | BLOOD PRESSURE, SKIN TEMPERATURE & MOISTURE, BEHAVIORAL SENSORS, VOICE RECOGNITION (E.G., KEYWORDS), NOISE MONITORING (DECIBELS), SOCIAL MEDIA MONITORING, ANGER-INDUCING ENVIRONMENTAL/CONTEXT DETECTION |
| ANXIETY | BREATHING/ HEART RATE SENSORS, SLEEPING SENSORS, BAC SENSORS, SKIN MOISTURE TEMPERATURE SENSORS, PANIC ATTACK DETERMINERS, ANXIETY-INDUCING ENVIRONMENT/CONTEXT DETECTION |
| BOREDOM | LACK OF MOVEMENT, LOW BLOOD PRESSURE DURING DAYTIME HOURS, ACTIVITY MONITORING |
| CHANGE | CHANGE OF ADDRESS, JOB TITLE, LIFE EVENT (DETECTED BY TIES TO OTHER SYSTEMS) |
| DEPRESSION | VOICE AND CORRESPONDENCE MONITORING (KEYWORDS, E.G., DEPRESSED); TEXT MONITORING (KEYWORDS), PHYSIOLOGICAL SENSORS, SOCIAL MEDIA MONITORING, (DEPRESSING) ENVIRONMENT/CONTEXT DETECTION |
| ESCAPE | KEYWORD RECOGNITION, STRESS-RELATED SENSORS, SOCIAL MEDIA MONITORING, EXERCISE/ACTIVITY TRACKING |
| ENVY | BEHAVIORAL SENSORS |
| EXTREME EMOTIONS | NOISE/VOICE SENSORS, BEHAVIORAL SENSORS, SOCIAL MEDIA MONITORING, SADNESS "DETECTION" |

| TRIGGER LIST FOR ADDICT JOHN DOE | KEY SENSOR(S) READINGS, SYSTEMS, PARAMETERS, NEEDED TO MONITOR |
|---|---|
| MEDIA | NOISE/VOICE SENSORS, ACTIVITY MONITORING (WEB, TV USAGE), SOCIAL MEDIA MONITORING |
| MID-LIFE CRISIS | PURCHASE PATTERNS (E.G., RED CORVETTE), CORRESPONDENCE MONITORING |
| MONEY | FINANCIAL MONITORING, SPENDING AND SHOPPING PATTERNS |
| MUSIC | MUSIC STATIONS MONITORING (E.G., SIRIUS XM, PANDORA); NOISE SENSORS, SPECIALTY SOUND SENSORS |
| NOISE | NOISE/DECIBEL-MEASURING SENSORS, SPECIALTY NOISE DETECTION (E.G., CHILDREN, DOG BARKING) ENVIRONMENTAL/CONTEXT DETECTION |
| DISORDER | VISUAL/IMAGE ANALYSIS (OF HOME, OFFICE) |
| OVERCONFI DENCE | PROXIMITY-RELATED AND ENVY-RELATED SENSORS, ENVIRONMENTAL/CONTEXT DETECTION |
| PEER PRESSURE | LIFE-FORM (SPECIFIC PEOPLE) MONITORING, INCLUDING SOCIAL MEDIA. CORRESPONDENCE MONITORING |
| POWER LESSNESS | PHYSIOLOGICAL AND BEHAVIORAL MONITORING SENSORS. SADNESS "DETECTION", SOCIAL MEDIA MONITORING |
| PROXIMITY | BREATHALYZER, BAC SENSORS, OLFACTORY SENSORS |
| QUITTING (FEAR OF) | SEPARATE QUESTIONNAIRE. CUSTOM SENSOR/SENSOR ARRAY CREATION |
| RELATIVES | MONITORING LOCATION OF RELATIVES, SOCIAL MEDIA MONITORING, CORRESPONDENCE MONITORING |
| RELATIONSHIPS | LOCATION OF SPECIFIC PERSON(S), SOCIAL MEDIA MONITORING, CORRESPONDENCE MONITORING |

FIG. 15

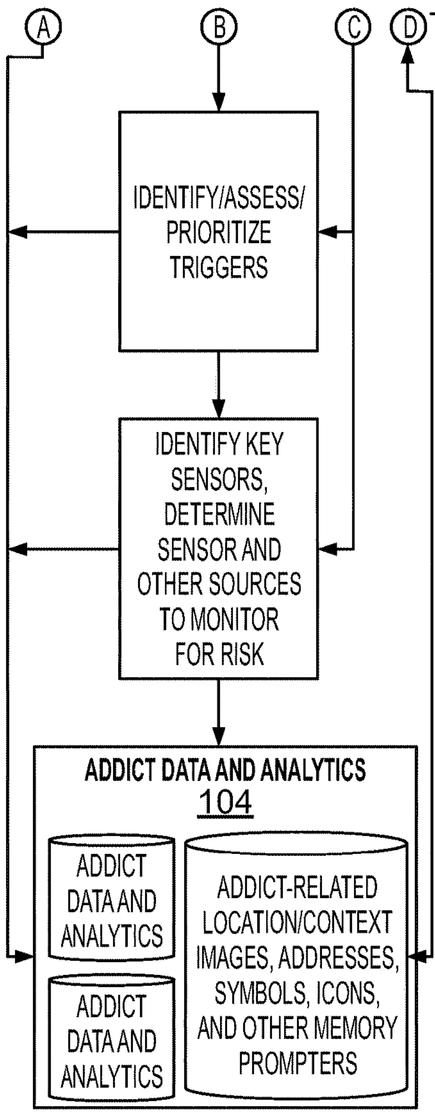

| | |
|---|---|
| FRUSTRATION | BLOOD PRESSURE SENSOR, BEHAVIORAL SENSORS, SOCIAL MEDIA MONITORING, FRUSTRATION ENVIRONMENTAL/CONTEXT DETECTION (E.G., DMV, TRAFFIC JAMS, EX CORRESPONDENCE) |
| FUN | ACTIVITY MONITORING AND SENSORS, BEHAVIORAL SENSORS, SOCIAL MEDIA MONITORING |
| GUILT | KEYWORD MONITORING (AUNT MAY DIED, ETC.), SOCIAL MEDIA MONITORING |
| HEALTH | PHYSIOLOGICAL, EXERCISE SENSORS, MEDICAL BILL MONITORING |
| HOLIDAYS | CALENDAR, STRESS-RELATED SENSORS, TIES TO HOLIDAY PLANS/CALENDAR, SOCIAL MEDIA MONITORING |
| HUNGRY | FOOD, CALORIE MONITORING, BLOOD SUGAR SENSOR |
| INSOMNIA | SLEEP, BED SENSORS, CAFFEINE-INTAKE MONITORING |
| JOB | CORRESPONDENCE MONITORING (E.G., EMAILS ABOUT BOSS), SOCIAL MEDIA MONITORING |
| KIDS | CHILDREN A, B, C LOCATION AND ACTIVITY, STRESS-RELATED SENSORS, NOISE SENSORS (VOLUME AND PITCH) |
| LONELINESS | LIFE-FORM DETECTORS, ACTIVITY MONITORING, SOCIAL MEDIA MONITORING, KEY FRIEND/RELATIONSHIP LOCATION MONITORING |
| REMINDERS | MUSIC STATION MONITORING, KEYWORD MONITORING, ENVIRONMENTAL/CONTEXT DETECTION |
| SEX | KEYWORD MONITORING; PHEROMONE SENSORS, (SEXUAL) ENVIRONMENTAL/CONTEXT DETECTION |
| SMELL | OLFACTORY SENSORS |
| SOCIAL SITUATIONS | NOISE, PROXIMITY MONITORING, LOCATION OF SPECIFIC PEOPLE, OLFACTORY (SMELL) SENSORS, PROXIMITY SENSORS, ENVIRONMENTAL/CONTEXT DETECTION |
| STRESS | ENVIRONMENTAL/CONTEXT DETECTION, ETC. |
| TASTE | OLFACTORY SENSORS, BIOGESTATION SENSORS, BAC SENSORS |
| TIMES OF DAY | CLOCKS, CALENDARS, ENVIRONMENTAL/ CONTEXT DETECTION |
| TIRED | INSOMNIA SENSORS, BLOOD SUGAR, PHYSIOLOGICAL SENSORS, ACTIVITY MONITORING |
| UNFUN/ UNINTERESTING | ACTIVITY MONITORING AND SENSORS, BEHAVIORAL SENSORS, SOCIAL MEDIA MONITORING |
| VICTIM (ABUSE, SELF-ESTEEM) | DEPRESSION, SEX-RELATED SENSORS |
| WEATHER | BAROMETRIC SENSORS; WEATHER SENSORS, MONITOR WEATHER CHANNEL |
| (E)X WIFE/ PARTNER/ETC. | LOCATION MONITORING OF SPECIFIC INDIVIDUALS, SOCIAL MEDIA MONITORING, KEYWORD MONITORING, CHILDREN TRACKING/MONITORING |
| YELLING (CONFRONT ATION) | VOICE RECOGNITION AND NOISE MONITORING (DECIBELS);SPECIALTY SOUND SENSORS, PROXIMITY MONITORING (OF FREQUENT YELLERS) |
| ZEAL (EXCITEMENT) | BREATHING/ HEART RATE SENSORS, MOTION SENSORS, BLOOD PRESSURE, ENVIRONMENTAL/ CONTEXT DETECTION, RESPIRATORY RATE |

FIG. 15 (Cont.)

Drinking Triggers and Their Related Triggers

| LOCATION | CORE BASIS | Date/ Time | Time/Location Coordinate System | X Equivalent | Y Equivalent | Z (altitude) | Oxygen Level (O2) | CO2 Level | Radiation | Light Intensity | Gravity (Surface) | Temp | Humidity |
|---|---|---|---|---|---|---|---|---|---|---|---|---|---|
| 1 | Earth | 05/13/22 14:25:46 | Time A/ Coordinate System A | 38.6270 N | 90.1994 W | 142 Meters | 21.1% | 400 ppm | .01 mrem | 50 lx | 1.00 | 82 F | 47% |
| 2/ M1 | Moon | Adjust 1 | Time A/ 'Coordinate System A (Earth-Moon); B (Moon only); B' Moon-Mars | Adjust 1 | Adjust 1 | Adjust 1 | Adjust 1 | Adjust 1 | Adjust 1 | Adjust 1 | Adjust 1 | Adjust 1 | Adjust 1 |
| 3/ PX 1 | Planet X | Adjust 2 | Time X, Coordinate System X | Adjust 2 | Adjust 2 | Adjust 2 | Adjust 2 | Adjust 2 | Adjust 2 | Adjust 2 | Adjust 2 | Adjust 2 | Adjust 2 |
| 4/ SSA1 | Space Station A | Adjust 3 | Time A, Coordinate System SSA/EA/MA' | Adjust 3 | Adjust 3 | Adjust 3 | Adjust 3 | Adjust 3 | Adjust 3 | Adjust 3 | Adjust 3 | Adjust 3 | Adjust 3 |
| 5/ AB1 | Asteroid B | Adjust 4 | Time AB, Coordinate system F | Adjust 4 | Adjust 4 | Adjust 4 | Adjust 4 | Adjust 4 | Adjust 4 | Adjust 4 | Adjust 4 | Adjust 4 | Adjust 4 |
| 6/ SC1 | Ship C | Adjust 5 | Time A, Coordinate system depending on beginning/ end nodes | Adjust 5 | Adjust 5 | Adjust 5 | Adjust 5 | Adjust 5 | Adjust 5 | Adjust 5 | Adjust 5 | Adjust 5 | Adjust 5 |

FIG. 20

SYSTEMS AND METHODS FOR THE MANAGEMENT, MONITORING, IMPROVEMENT, AND RESEARCH OF MEDICINE AND HEALTH IN OFF-EARTH, NON-EARTH, AND SPECIALTY ENVIRONMENTS

CROSS-REFERENCE TO RELATED APPLICATIONS

The present application claims the benefit and priority of U.S. Provisional Patent Application Ser. No. 63/460,523 filed Apr. 19, 2023.

The present application claims the benefit and priority of U.S. Provisional Patent Application Ser. No. 63/441,569 filed Jan. 27, 2023.

The present application also claims the benefit and priority of U.S. Provisional Patent Application Ser. No. 63/344,976 filed May 23, 2022.

The present application is a continuation-in-part of U.S. patent application Ser. No. 18/090,047 filed Dec. 28, 2022.

U.S. patent application Ser. No. 18/090,047 is a continuation-in-part of U.S. patent application Ser. No. 17/192,381 filed Mar. 4, 2021, which published as US2021/0202067 on Jul. 1, 2021.

U.S. patent application Ser. No. 18/090,047 claims the benefit and priority of (1) U.S. Provisional Patent Application Ser. No. 63/294,815 filed Dec. 29, 2021; (2) U.S. Provisional Patent Application Ser. No. 63/344,976 filed May 23, 2022; and (3) U.S. Provisional Patent Application Ser. No. 63/316,277 filed Mar. 2, 2022.

U.S. patent application Ser. No. 18/090,047 is also a continuation-in-part of (1) U.S. patent application Ser. No. 17/861,559 filed Jul. 11, 2022, which published as US2022/0353632 on Nov. 3, 2022; (2) U.S. patent application Ser. No. 17/882,061 filed Aug. 5, 2022, which published as US2022/0386080 on Dec. 1, 2022; (3) U.S. patent application Ser. No. 17/541,707 filed Dec. 3, 2021, which published as US2022/0116736 on Apr. 14, 2022; and (4) U.S. patent application Ser. No. 17/903,419 filed Sep. 6, 2022.

U.S. patent application Ser. No. 17/192,381 claims the benefit and priority of (1) U.S. Provisional Patent Application No. 62/986,382 filed Mar. 6, 2020; and (2) U.S. Provisional Patent Application No. 63/011,949 filed Apr. 17, 2020. U.S. patent application Ser. No. 17/192,381 is a continuation-in-part of U.S. patent application Ser. No. 17/104,136.

U.S. patent application Ser. No. 17/861,559 is a continuation-in-part of U.S. patent application Ser. No. 16/700,601 filed Dec. 2, 2019, which published as US2020/0107155 on Apr. 2, 2020 and issued as U.S. Pat. No. 11,388,546 on Jul. 12, 2022.

U.S. patent application Ser. No. 17/882,061 is a continuation of U.S. patent application Ser. No. 17/104,136 filed Nov. 25, 2020, which published as US2020/0084451 on Mar. 18, 2021 and issued as U.S. Pat. No. 11,412,353 on Aug. 9, 2022.

U.S. patent application Ser. No. 17/541,707 claims the benefit and priority of U.S. Provisional Patent Application No. 63/120,834 filed Dec. 3, 2020. U.S. patent application Ser. No. 17/541,707 is a continuation-in-part of (1) U.S. patent application Ser. No. 16/700,601; (2) U.S. patent application Ser. No. 17/104,136; and (3) U.S. patent application Ser. No. 17/192,381.

U.S. patent application Ser. No. 17/903,419 claims the benefit and priority of (1) U.S. Provisional Patent Application Ser. No. 63/344,976 filed May 23, 2022; (2) U.S. Provisional Patent Application Ser. No. 63/316,277 filed Mar. 2, 2022; (3) U.S. Provisional Patent Application Ser. No. 63/294,815 filed Dec. 29, 2021; and (4) U.S. Provisional Patent Application Ser. No. 63/275,300 filed Nov. 3, 2021.

U.S. patent application Ser. No. 17/903,419 is also a continuation-in-part of (1) U.S. patent application Ser. No. 17/861,559 filed Jul. 11, 2022, which published as US2022/0353632 on Nov. 3, 2022; (2) U.S. patent application Ser. No. 17/882,061 filed Aug. 5, 2022, which published as US2022/0386080 on Dec. 1, 2022; (3) U.S. patent application Ser. No. 17/192,381 filed Mar. 4, 2021, which published as US2021/0202067 on Jul. 1, 2021; and (4) U.S. patent application Ser. No. 17/541,707 filed Dec. 3, 2021, which published as US2022/0116736 on Apr. 14, 2022.

U.S. patent application Ser. No. 17/104,136 claims the benefit and priority of U.S. Provisional Patent Application No. 63/011,949 filed Apr. 17, 2020. U.S. patent application Ser. No. 17/104,136 is a continuation-in-part of U.S. patent application Ser. No. 16/654,708 filed Oct. 16, 2019, which published as US2020/0051189 on Feb. 13, 2020 and issued as U.S. Pat. No. 10,853,897 on Dec. 1, 2020.

U.S. patent application Ser. No. 16/654,708 claims the benefit and priority of U.S. Provisional Patent Application No. 62/746,330 filed Oct. 16, 2018. U.S. patent application Ser. No. 16/654,708 is a continuation-in-part of U.S. patent application Ser. No. 16/516,822 filed Jul. 19, 2019, which published as US2019/0340906 on Nov. 7, 2019 and issued as U.S. Pat. No. 10,497,242 on Dec. 3, 2019. U.S. patent application Ser. No. 16/654,708 is also a continuation-in-part of U.S. patent application Ser. No. 15/840,762 filed Dec. 13, 2017, which published as US2018/0176727 on Jun. 21, 2018 and issued as U.S. Pat. No. 10,477,342 on Nov. 12, 2019.

U.S. patent application Ser. No. 16/516,822 claims the benefit and priority of U.S. Provisional Patent Application No. 62/701,252 filed Jul. 20, 2018. U.S. patent application Ser. No. 16/516,822 is a continuation-in-part of U.S. patent application Ser. No. 15/840,762.

U.S. patent application Ser. No. 16/700,601 is continuation of U.S. patent application Ser. No. 15/840,775 filed Dec. 13, 2017, which published as US2018/0173866 on Jun. 21, 2018 and issued as U.S. Pat. No. 10,555,112 on Feb. 4, 2020.

U.S. patent application Ser. No. 15/840,775 claims the benefit and priority of (1) U.S. Provisional Patent Application Ser. No. 62/435,042 filed Dec. 15, 2016; and (2) U.S. Provisional Patent Application Ser. No. 62/480,206 filed Mar. 31, 2017.

The entire disclosures of the above patents and patent applications are incorporated herein by reference.

FIELD

The present disclosure relates to systems, methods, and technologies for the management, monitoring, improvement, and research of medicine and health in off-Earth, non-Earth, and specialty environments.

BACKGROUND

This section provides background information related to the present disclosure which is not necessarily prior art.

Telemedicine generally refers to the ability to practice medicine, and/or in some form provide guidance, assistance, and/or information to assist, directly or indirectly, with some sort of medical issue for a person, an associate/loved one, or just provide background/educational information. Telemedicine has been practiced for numerous years now, as communications networks and applications such as ZOOM videotelephony app, have been able to support such information exchange or even allowed one person to access a medical-related database. Telemedicine practice is continuing to grow as various regulatory barriers have started to lessen, technological barriers have continued to ease, and human familiarity with telemedicine and the enabling technologies have grown.

But as recognized herein, traditional telemedicine presumes certain commonalities; in particular that the people involved, as well as machines, processes, and procedures, are trained for, calibrated for, setup up for, or otherwise assumes that they, and the people involved, are on the Earth—with the Earth's gravity, environmental conditions, even the body mass and bone and fluid densities of the patients, etc. Some, even many, of these Earth-related assumptions understandably may not, and probably do not, apply when applying medicine/medical-related practices to practicing medicine off-Earth/in space, in on-Earth "specialized" communities, such as post-disaster living communities, underground/underwater living habitats, or even quarantined or very rural areas, e.g., when at least one part of the medical "equation" (person(s), place(s), things(s), equipment, atmosphere, gravity, radiation levels, even computers/communications equipment/networks) is non-terrestrial and/or unusual, and that "unusualness" may somehow impact or influence key factors and/or assumptions involved in the practice of medicine.

DRAWINGS

The drawings described herein are for illustrative purposes only of selected embodiments and not all possible implementations and are not intended to limit the scope of the present disclosure. For example, drawings may be described herein with reference to an addict but in other exemplary embodiments the systems and devices shown in the drawings may be modified or configured to be usable for the management, monitoring, improvement, and research of medicine and health in off-Earth, non-Earth, and specialty environments as disclosed herein.

FIG. 1 is a diagram of an example system for determining location and context of an addict, a support network, and other information and aspects of an addict's personal and professional life for addiction treatment purposes, including relapse prevention and containment. This diagram includes various example networks and technologies that may be used for collecting and analyzing the addict's location and context. Also shown are example data sources and analytical engines that may be needed to process such data and to identify and implement actions to preempt, prevent, and/or contain any relapse. In other exemplary embodiments, the example system shown in FIG. 1 (and other figures) may be modified or configured to be usable for determining location and context for the management, monitoring, improvement, and research of medicine and health in off-Earth, non-Earth, and specialty environments as disclosed herein.

FIG. 2 describes an example Addict Monitor/Controller (AMC) device that may be used to collect, process, and disseminate context and addiction trigger-related data from and about an addict via various sensors and other data collection mechanisms, and to interface with/to the addict and 3rd party mechanisms. The device may also provide mechanisms to provide feedback to the addict and assist in the implementation of relapse-related preventative and containment actions. In other exemplary embodiments, the AMC device shown in FIG. 2 may be modified or configured to be usable to collect, process, and disseminate context and trigger-related data for the management, monitoring, improvement, and research of medicine and health off-Earth, non-Earth, and specialty environments as disclosed herein.

FIG. 2*a* provides examples of distributed sensor deployment, data collection options, localized sensors, and localized networks that may be used in exemplary embodiments.

FIG. 2*b* provides examples of internet of things (IoT) addict-related sensors, devices, and networks that may be used in exemplary embodiments.

FIG. 3 depicts example steps for monitoring an addict's triggers, and in the course of doing so assessing/predicting the addict's risk of relapse. FIG. 3 also describes identifying possible resources that could help the addict, and the actions that could be taken to prevent, preempt or contain a relapse. FIG. 3 also describes an example process for selecting such resources and actions.

FIG. 4 depicts an example system and example process for determining the location/context of an addict as well as the location/context of support resources using a variety of sensors and other information sources.

FIG. 5 describes an example system and example process for assessing an addict's trigger/relapse risk. FIG. 5 also describes how such algorithms could be made self-learning to better assess an addict's relapse risk.

FIG. 5A depicts an example embodiment of a method for managing damage control and recovering from a relapse situation.

FIG. 5B provides examples of risk, support areas maps, and map mashups.

Figure 7:
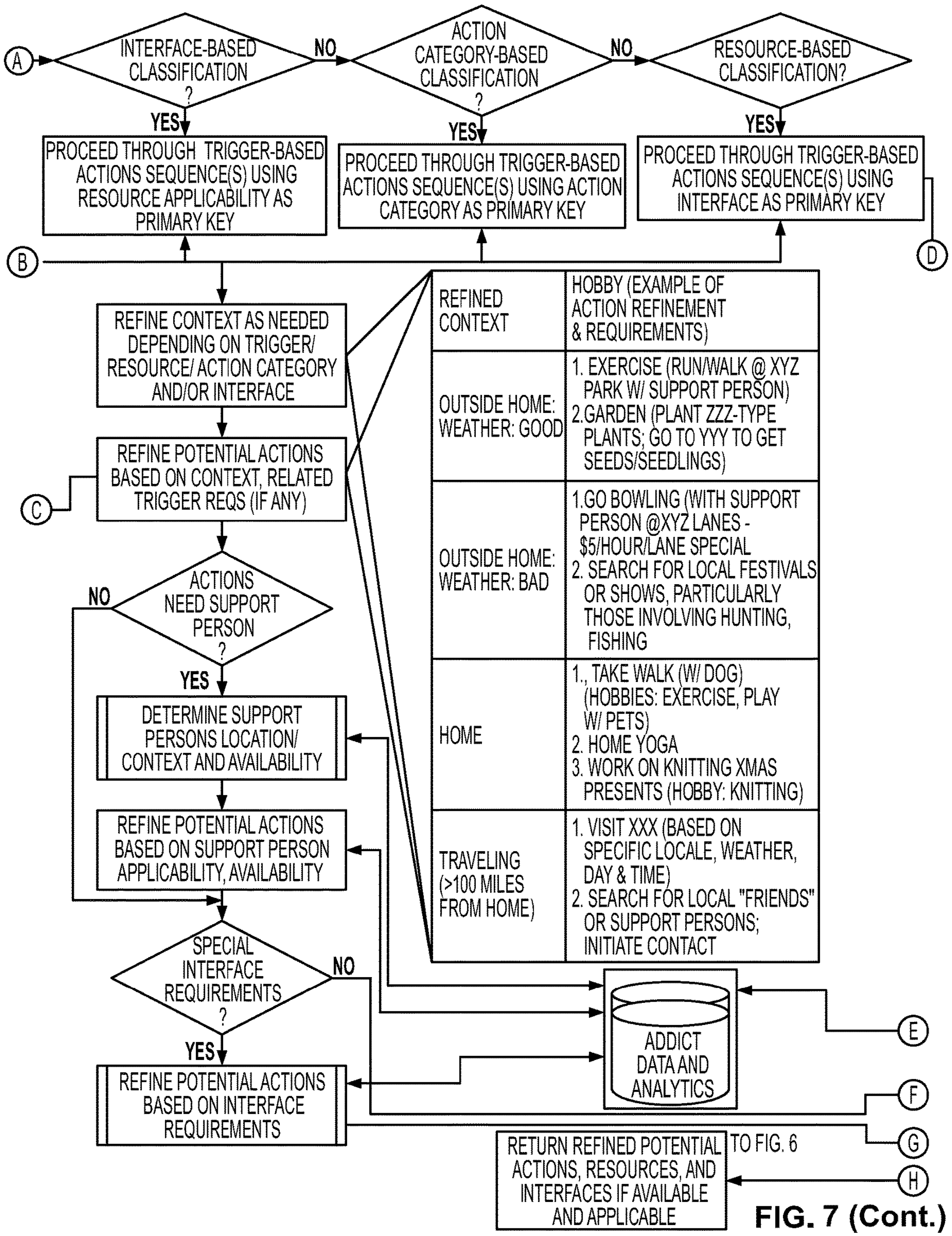

FIG. 7 describes example ways to identify/determine and select the best actions and resources when relapse risk is high.

FIG. 7A describes an example of an action-determining sub process—specifically, ways to utilize regularly scheduled addict community meetings or spontaneous, unscheduled, flash addict community meetings.

Figure 8:
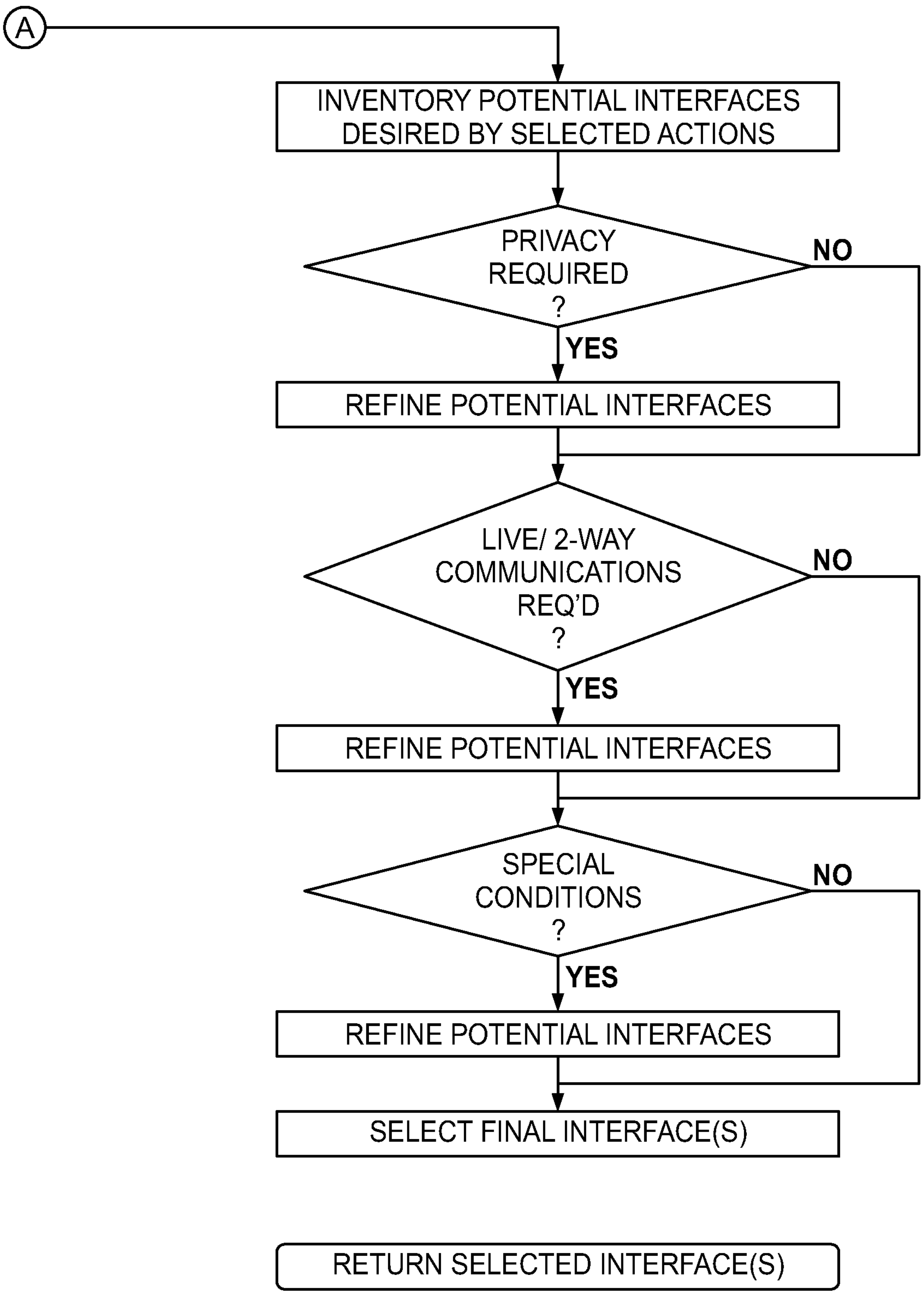

FIG. 8 describes example ways to select the best interface(s) for interacting with an addict, including implementing relapse prevention actions.

FIG. 9 describes an example addict rewards/demerits system based on an addict's behaviors and actions, which may include rewarding (or punishing) an addict based on behavior via tracking and data analytics and various reward mechanisms.

Figure 10:
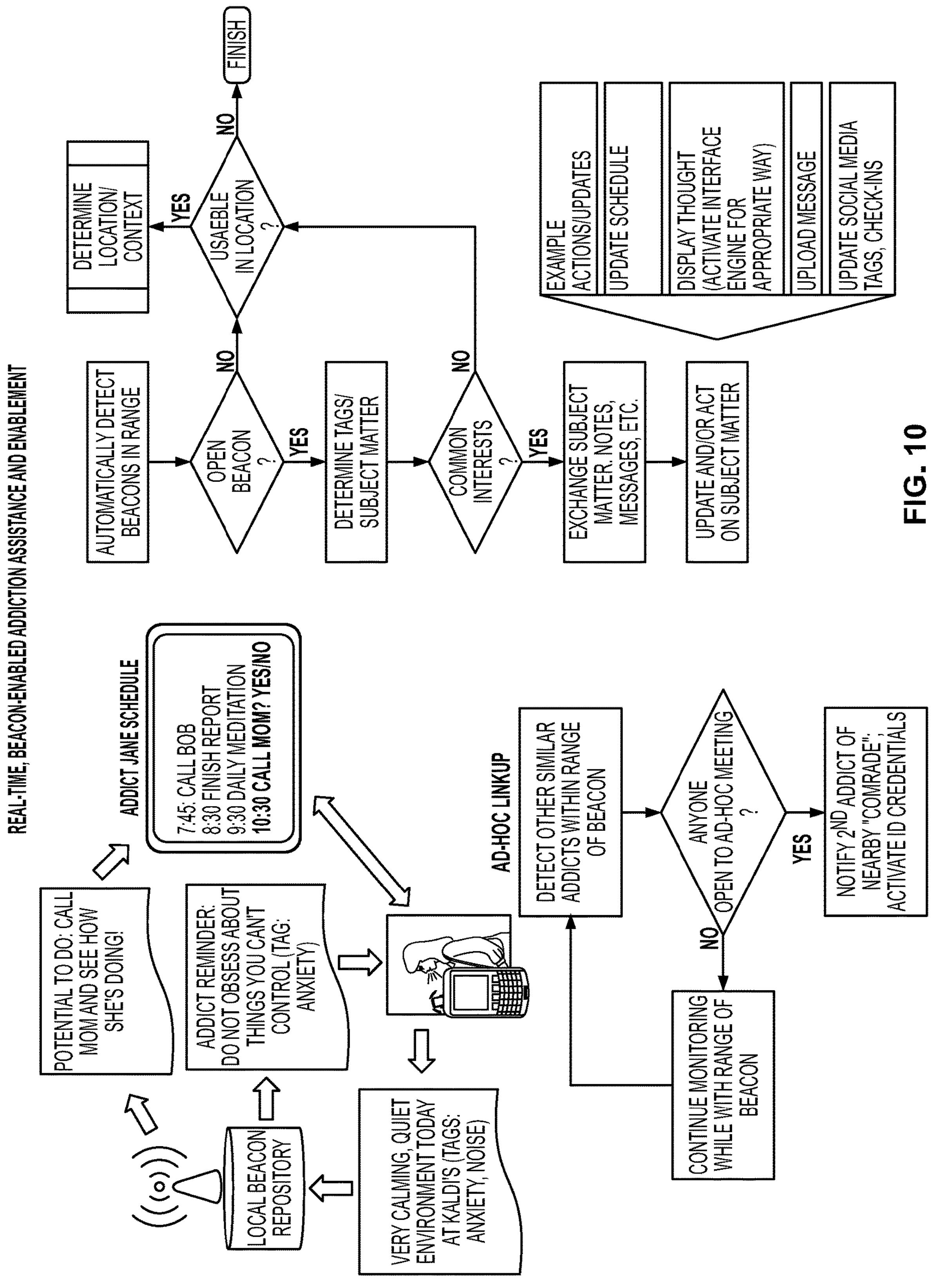
Figure 12:
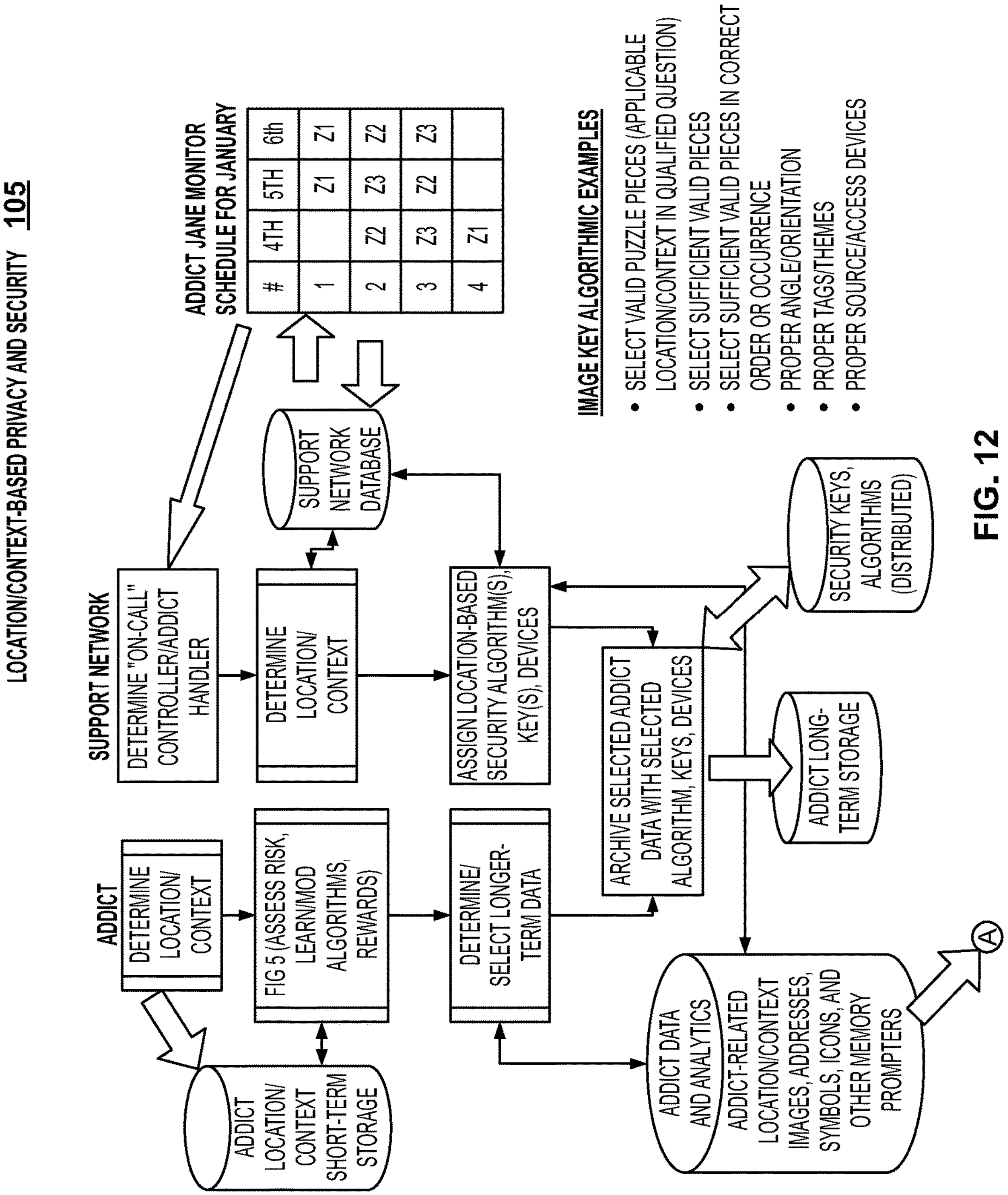
Figure 13:
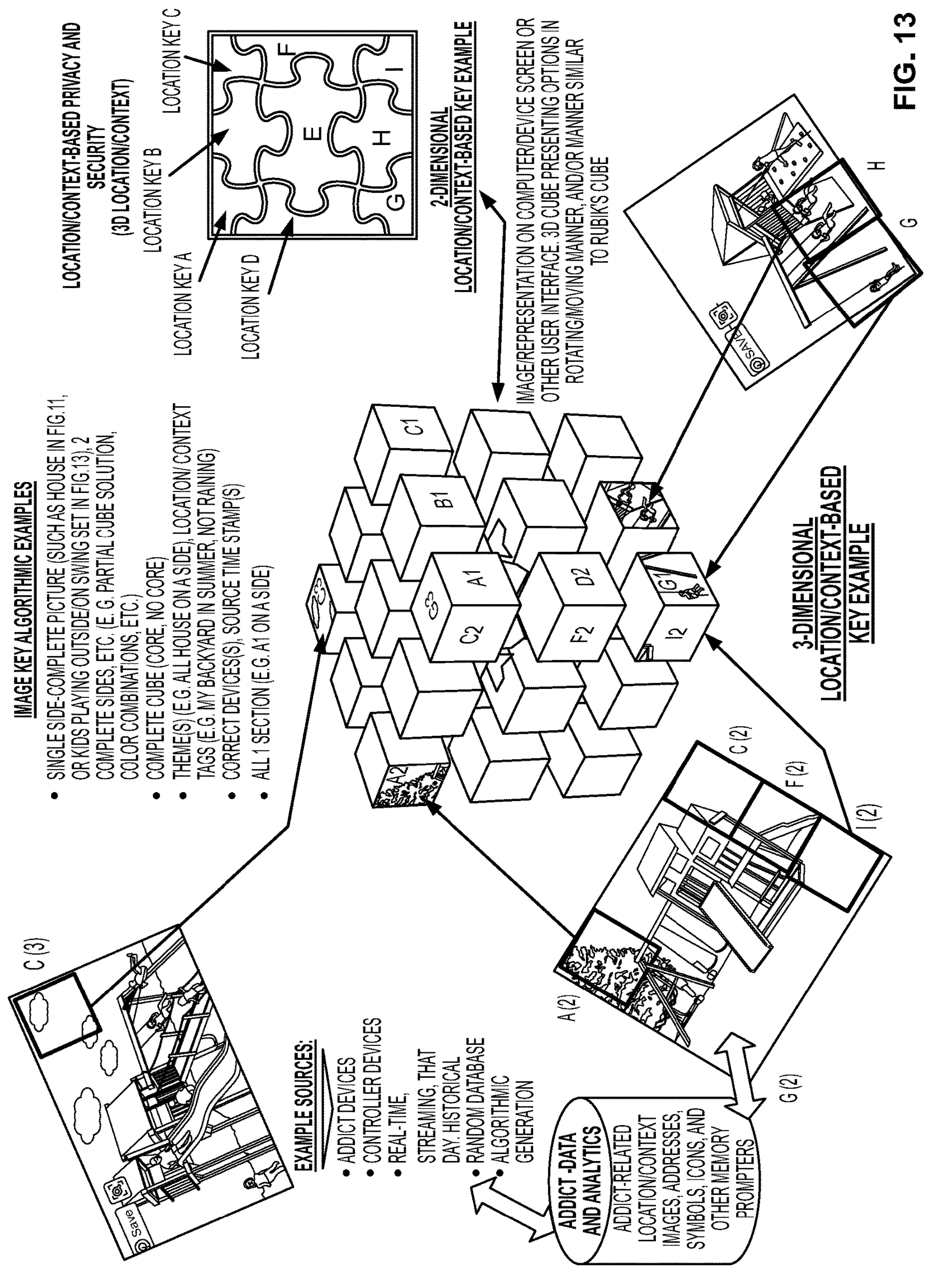

FIG. 10 describes example ways in which addicts can receive and transmit sobriety ideas in public and private places via beacons. FIG. 10 also illustrates example ways in which Real-Time Location System (RTLS) technologies can be used to enable ad hoc, spontaneous, unscheduled, or flash addict meetings between people with similar addiction issues.

FIG. 11 thru 14 describe examples of using location and/or context information to provide privacy and security for data collected in various implementations of the present disclosure.

FIG. 15 depicts an example embodiment of a method for monitoring for a risk of a pre-identified behavior (e.g., pre-identified addict-related undesirable behavior, etc.). FIG. 15 also includes example triggers, priorities, and initial risk assessment/detection sensors.

Figure 16:
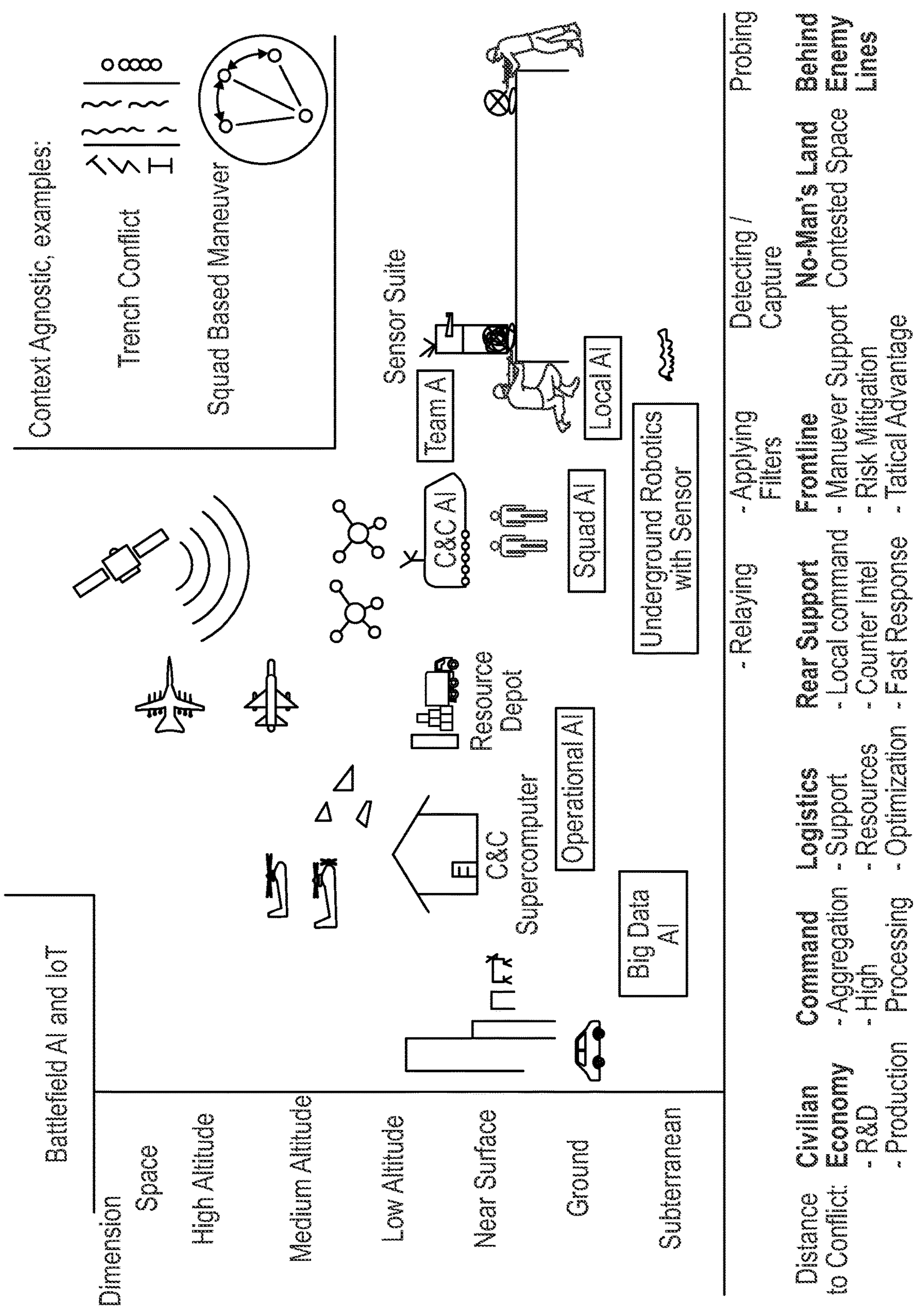

FIG. 16 is a diagram of example conflict battlefield architecture.

Figure 17:
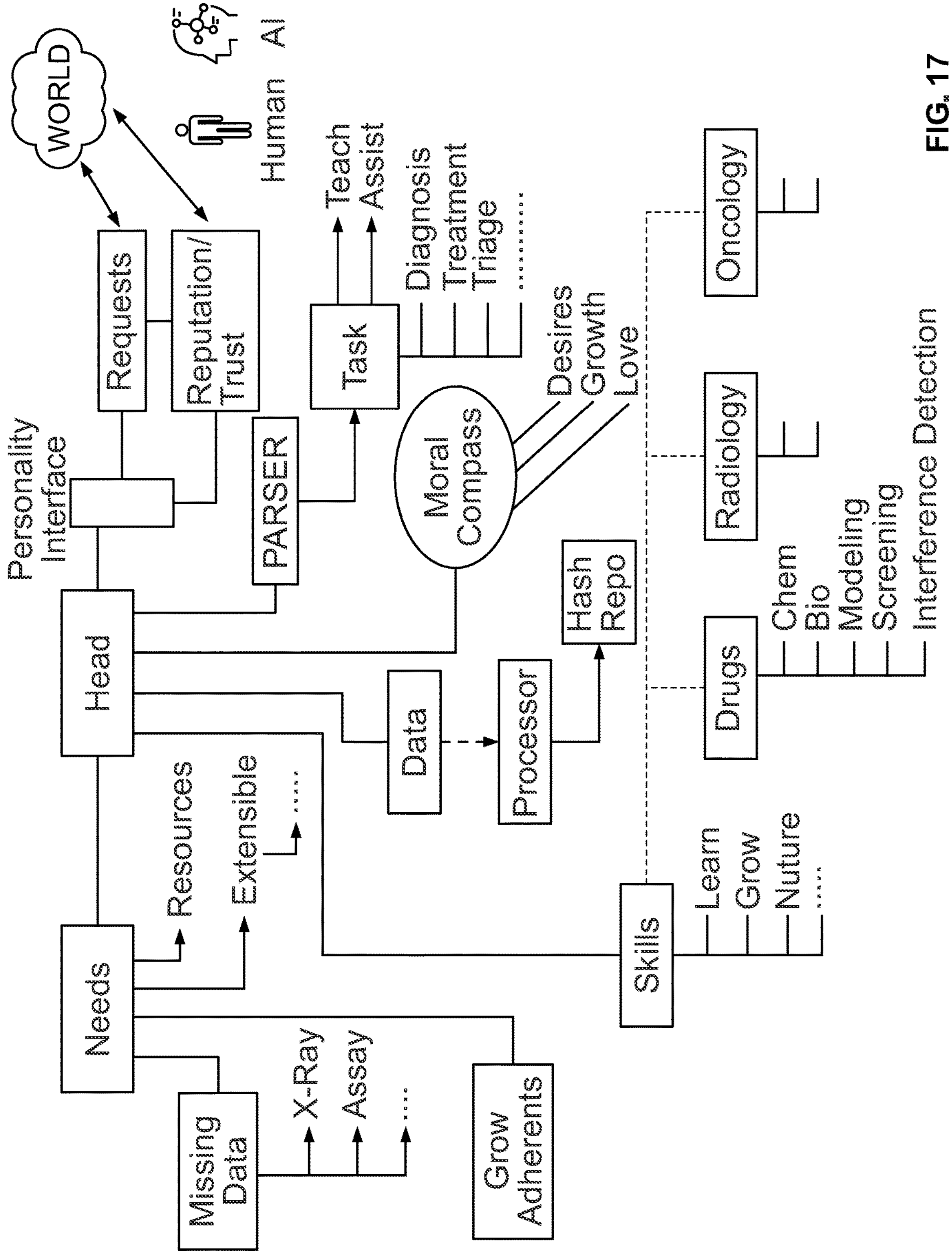

FIG. 17 illustrates an example system according to an exemplary embodiment focused on medicine and drug discovery for treatment of disease, including need-based driving, missing data collection, growing extensibility, skill instructional framework, human and AI elements, reputation management with the world, a moral compass/ethical framework to guide, and additional tasks.

Figure 18:
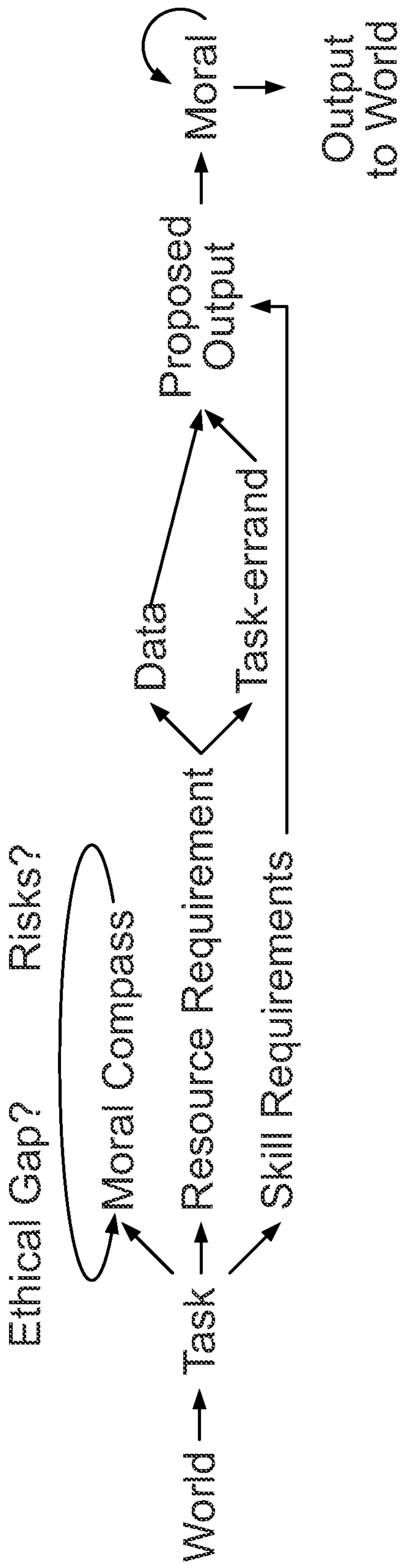

FIG. 18 illustrates an example system according to an exemplary embodiment including a moral compass.

Figure 19:
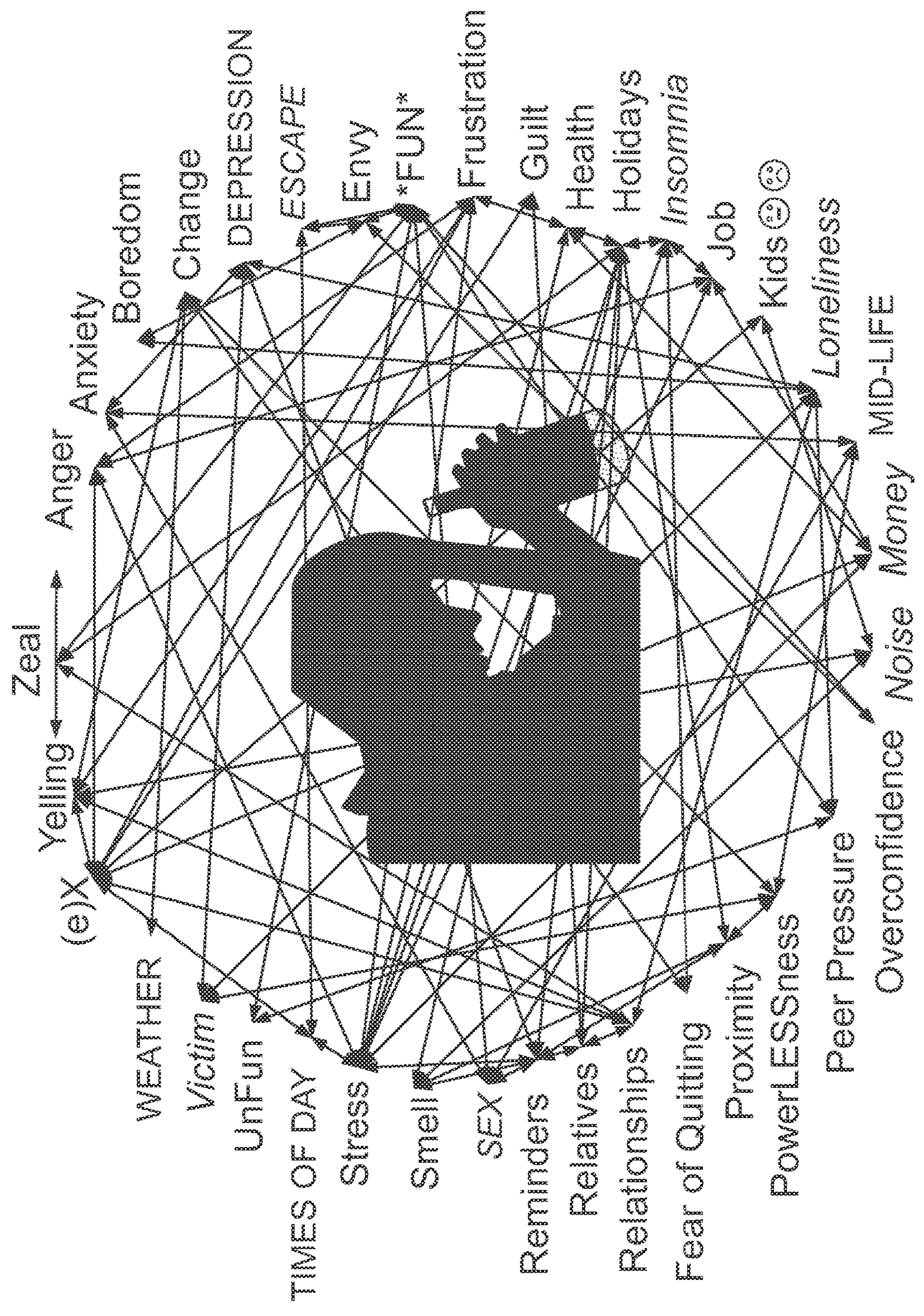

FIG. 19 is a diagram depicting various examples of triggers (e.g., drinking triggers, etc.) and how the triggers may be related or interconnected such that one or more trigger(s) may activate one or more related trigger(s).

FIG. 20 includes a table that includes different locations and variables that accompany the different locations, which table may be created and/or used while practicing space medicine according to exemplary embodiments disclosed herein.

Figure 21:
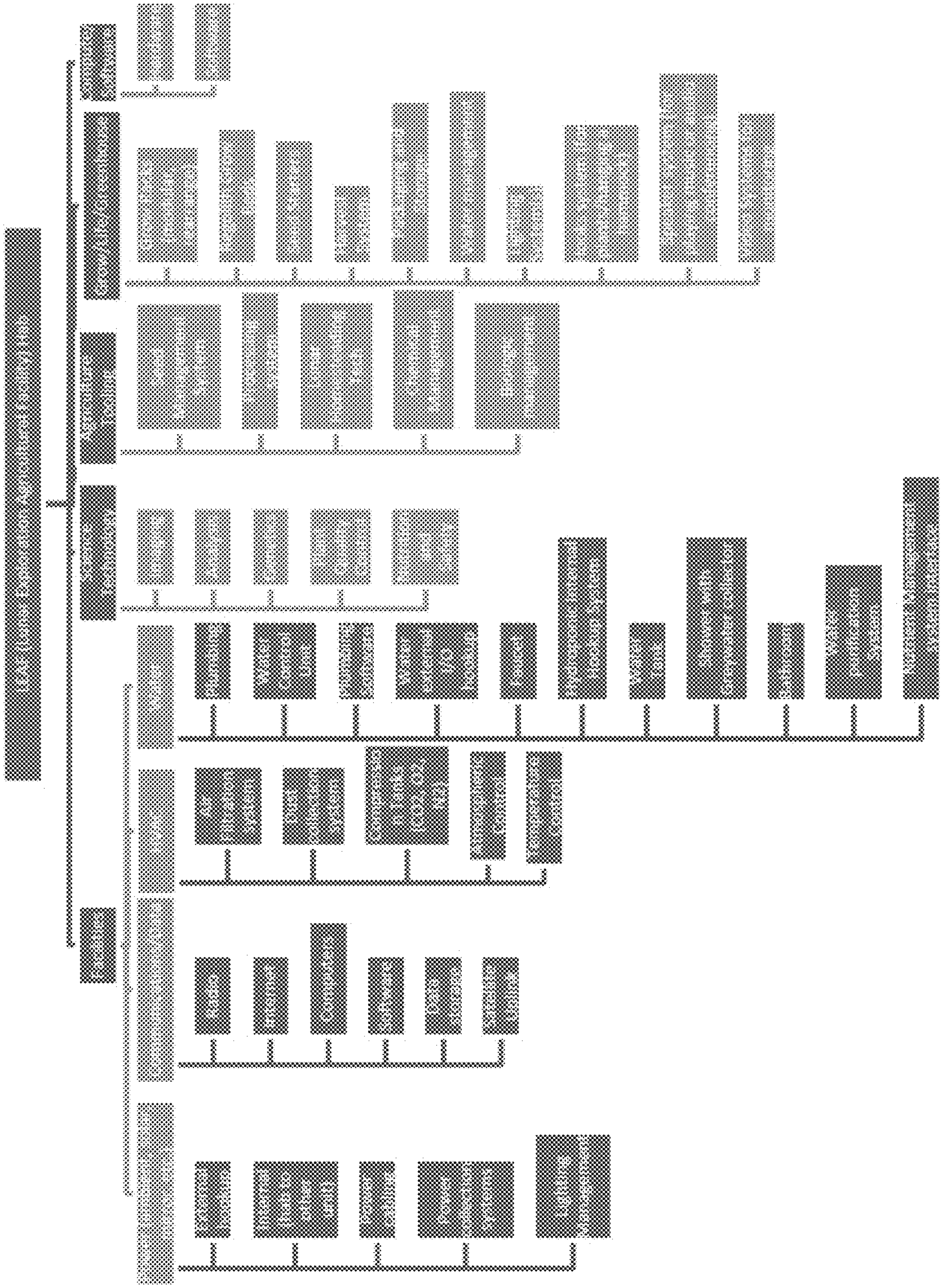

FIG. 21 illustrates various features that may be included in a Lunar Exploration Agricultural Facility Habitat.

Figure 22:
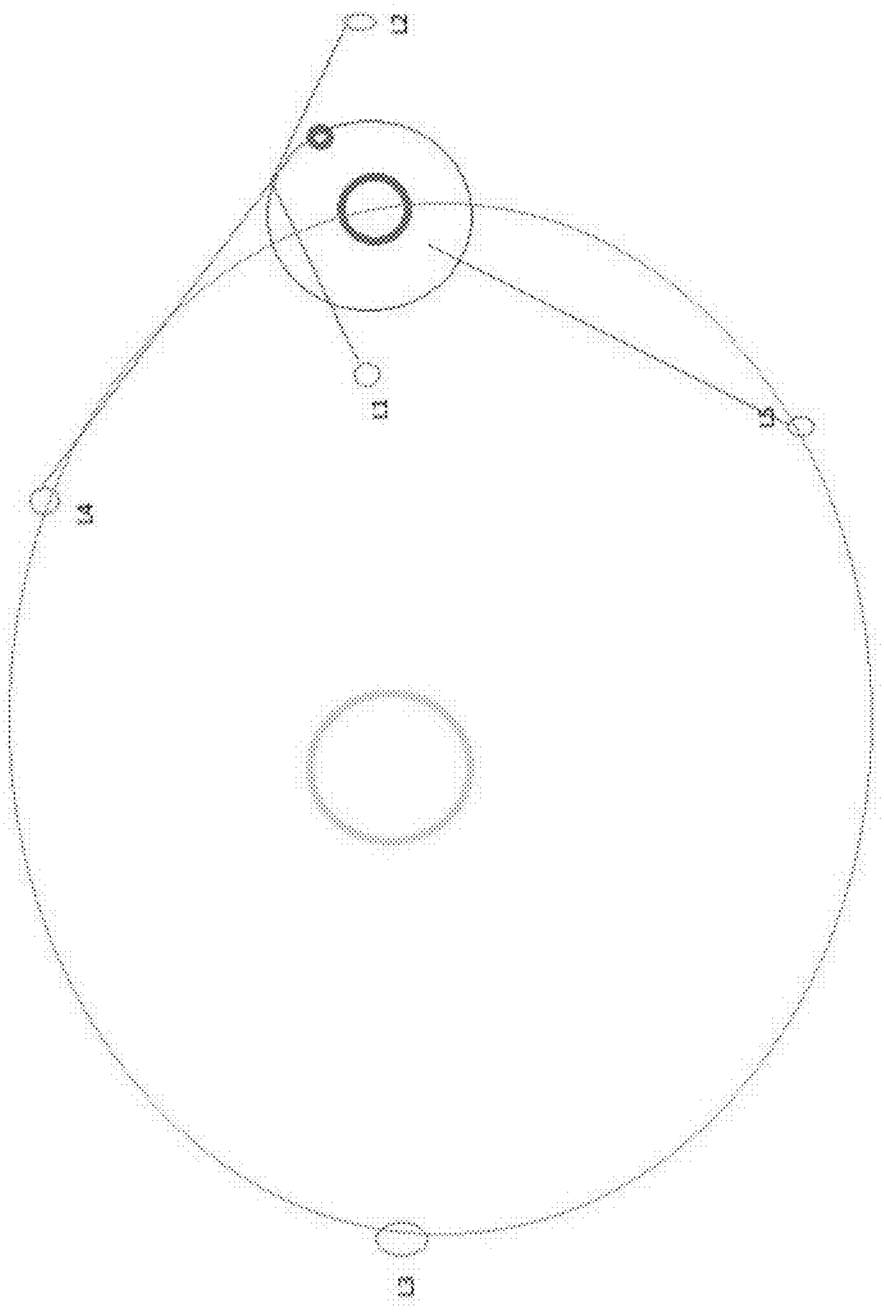

FIG. 22 illustrates LaGrange points that are stable points of equilibrium for small-mass objects under the influence of two massive orbiting bodies. Mathematically, this involves the solution of the restricted three-body problem in which two bodies (e.g., the Sun and the Earth) are very much more massive than the third body, which in this example is a satellite shown as a small circle orbiting around the Earth.

Figure 23:
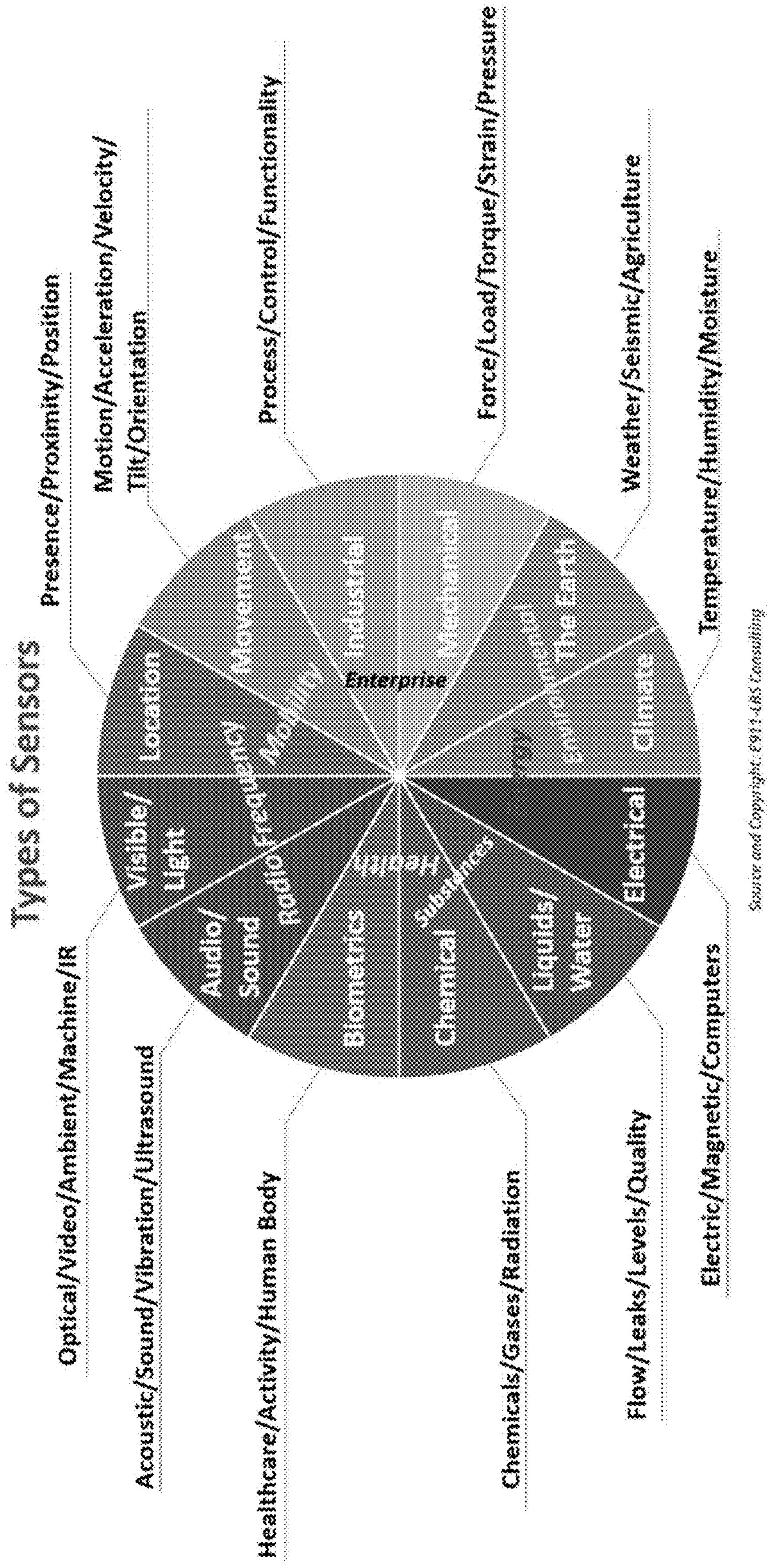

FIG. 23 illustrates different sensors that may be utilized by a system configured to be operable as or include a context determination engine or contextualization engine according to exemplary embodiments of the present disclosure. As disclosed therein, the context determination or contextualization engine may be operable for collecting individual measurements, comparing the measurements to other measurements, performing and applying adjustment calculations to each individual measurement, and generating a single score or set of scores to capture the context on a variety of sensor dimensions, with a given context being determined by a plurality of sensor measurements utilizing sensors from a broad and deep portfolio of possibilities.

DETAILED DESCRIPTION

The following description is merely exemplary in nature and is in no way intended to limit the present disclosure, application, or uses.

As recognized herein, traditional telemedicine presumes certain commonalities; in particular that the people involved, as well as machines, processes, and procedures, are trained for, calibrated for, setup up for, or otherwise assumes that they, and the people involved, are on the Earth—with the Earth's gravity, environmental conditions, even the body mass and bone and fluid densities of the patients, etc. Some, even many, of these Earth-related assumptions understandably may not, and probably do not, apply when applying medicine/medical-related practices to practicing medicine off-Earth/in space, in on-Earth "specialized" communities, such as post-disaster living communities, underground/underwater living habitats, or even quarantined or very rural areas, e.g., when at least one part of the medical "equation" (person(s), place(s), things(s), equipment, atmosphere, gravity, radiation levels, even computers/communications equipment/networks) is non-terrestrial and/or unusual, and that "unusualness" may somehow impact or influence key factors and/or assumptions involved in the practice of medicine.

As further recognized herein, off-Earth living—and medicine practice—will be especially unusual as more persons go to space and colonies are established. A by-product of this increasing volumes of humanity will be deviation from the historical near-perfect-physical-specimens that have been the prerequisite to send into space up to recently. It is highly likely that many of the humans that go to these specialized communities in the future will be less-than-perfectly physically (and mentally), and thus the need for medicine/medical practice in these environments will greatly increase not only in volume and breadth of issues, but also in complexity of issues. No longer will there be the assumption/presumption that historical data about a person's physical health, as well as the data associated with ailment diagnosis and treatment, having been done in an "Earth-normal" context, will continue to be applicable in the future, e.g., predictable/relatively consistent gravity, atmosphere, food/water composition, radiation levels, temperature ranges, etc. Further, as more people stay longer in specialized communities (or are born there), new ailments, or at least highly divergent variation of existing ailments, will likely increasingly occur. Already it is known that bone and muscle mass loss occur with extended stays in space, among other issues, that (in theory) are due to microgravity for example. But compared to Earth databases little is known about off-Earth ailment root causes and treatments, and individual variations, and the data associated with these issues is not only miniscule, but due to the persons historically involved generally apply mostly to people in near-perfect health. As persons stay in space not only months but years, and at much older ages, the complexities will further increase. It should be noted, however, that all aspects of the inventions disclosed herein can apply to Earth-only or even "entity" only, e.g., a planet, Moon, asteroid, space station, space travel ship/capsule, satellite, etc. Similar situations are possible in various environments on Earth as well, particularly at high altitudes and the ocean depths, as well as artificially controlled environments differing significantly from "normal" Earth conditions, or other (often human-caused) abnormal environments (e.g., Chernobyl, Fukushima, and 3-Mile Island nuclear disasters, etc.).

To at least in part address these complexities, systems and methods will be needed to appropriately compare, adjust, cross-reference, calibrate, synchronize and otherwise compensate/adjust for differences between contexts off-Earth with those on-Earth, where the vast majority of historical medical practice and associated data has been collected/practiced, and these specialized environments, where contextual factors such as gravity, radiation, and a host of other factors can be very different. Put another way, not only will a medical practitioner (including the patient self-practicing) need to worry about what a test, process, procedure, treatment, recovery, etc. ("test" for short) is done, but where, when, how, why, and even who is performing it, e.g., the context. One key variation in contexts may be all that is needed to make a test worthless, or even worse, be used for a treatment that is wrong.

Doing the adjustments to data based on context typically need to be done after the fact (e.g., after a test is over) to appropriately cross-reference, etc., it will be highly complex and dynamic, as conditions in these specialty communities (particularly off-Earth) will be constantly changing Indeed, a scope of innovative aspects of this invention is the use of a "context determination engine" that not only collects, stores, processes, analyzes, and applies data from all manners of sensors (e.g., FIG. 23, etc.) directly relevant to the context related to a particular test (say radiation and gravity levels), and many physical aspects about the human involved that are not collected today, presumed, or collected but not a factor/major factor in how the test is conducted (e.g., weight in the microgravity, body mass, temperature, as well as many other body measurements). Further, it is anticipated that mental issues, and mental issues contribution to physical issues, will be of major consequence to diagnosis and treatment of specialized community participants, and thus extensive data on state-of-mind and other mental aspects will need to be collected not only for mental issues (e.g., anxiety) but for any and all types of issues, mental and/or physical, to appropriately assess the patient in these unusual conditions and environment associated with specialize communities.

Contextual data collection will not end there. For example, metadata associated with the test will need to be captured, such as test room temperature, composition (venting, materials, even plants in the room), equipment, who was involved, even the "weather" outside (presence of solar flares for example) and so forth, In turn, all test data, other data, etc. will need to be contextualized such that it can be appropriately calibrated, cross referenced, etc. to not only on-Earth data sets, but to other data for similar tests, etc. done on/in other specialty contexts—even those seemingly similar in the more obvious contextual elements, but due to the nature of the specialized community may differ in a critical non-obvious respect.

In order to make results from tests, examinations, etc. as apples-to-apples as possible, in addition/instead of contextualizing the data after-the-fact, it may be desirable to modify the context before a test, examination, etc. is performed. In short, an adjustment may be made to the context in which the test is performed to minimize the after-test data contextualization adjustments/calibration/etc. that need to be done. Thus, the present disclosure describes the ability to not only measure, collect, process, analyze, and apply contextual corrections, etc. to the data, but to instead (or in addition to) interface with the context to change the context before (and during) the test to match (as much as is practicable/possible) the context to the context of the baseline data set(s) that the test data will be compared to. Thus, a variety of modifications to the context before the test is done may be made: radiation levels elevated or reduced, gravity levels (if/when possible) changed, temperature, humidity, oxygen levels elevated, etc. Preemptive mental contextual changes may also be needed, e.g., for anxiety tests in different environments from smoothing and quiet to loud and confrontational may need to be introduced into the context, through everything from harsh environments to certain people doing certain behavior to acting out certain interactions in real-type environments (potentially using metaverse/augmented reality, etc.). The adjustment to the context pre-testing preferably enables the testing to occur in a context as close to the context when the baseline set of data was obtained, to thereby remove/negate as possible data influencers those factors in assessing the test results, and thus minimize contextualization needed to be made after the fact. A context determination engine could serve not only as the key element in contextualizing many diverse systems in diverse contexts across diverse specialized communities, but the context determination engine could also serve as the controller to make a subset of these diverse contexts more alike, at least for a short time for a certain purpose. Further, the present disclosure anticipates the need for a specialized context coordinate system that structure the myriad of types of sensors and devices that will be used to collect the contextual data, such as shown in FIG. 23.

The sensors can include location sensors (e.g., for detecting, measuring, determining, and/or calculating presence/proximity/position/absolute location/relative location/hybrid) including radio frequency-based location systems, cellular-based network technologies and methods, satellite systems (e.g. GPS, GLONASS, Starlink, etc.), movement and directional sensors (motion/acceleration/velocity/tilt/orientation/yaw/pitch/roll) including inertial sensors, motion sensors/detectors, accelerometer and velocity sensors, gyroscope sensors, and analog and digital compasses. The sensors can include industrial sensors (e.g., for determining/measuring/calculating/controlling processes/control capabilities/functions and functionality), mechanical sensors (e.g., for force/load/torque/strain/pressure); "Earth" sensors (e.g. weather/seismic/agriculture (group: environmental); climate sensors (e.g. temperature/humidity/moisture (Groups: Environmental, Energy); electrical/electronic sensors (e.g., electric/magnetic/computers/quantum/metaverse/augmented and virtual reality); liquids, water/vapor/ice sensors (e.g., flow/leaks/levels/quality/state; chemical sensors chemical/gas/toxicity/radiation; biometric sensors (e.g., human body/activities/health care); audio/sound/audible sensors (e.g. acoustic/sound/vibration/ultrasound); (in)visible/light sensors (e.g. optical/image/video/ambient/machine/infrared/other).

Each sensor type, and/or test, process, procedure, treatment, and/or recovery process would have some sort of automated checklist and associate scoring system that collects the contextual "raw" data into an organized structure, with a range of values, numbers, results, an/or states to characterize those outcomes. Then, depending on the outcomes and where they sit in a coordinate framework, a score or set of scores will be developed to capture the "value" of a particular portfolio of contextual factors. For example, a room 10 feet×10 feet wide, closed venting, early normal radiation, temperature levels, but one-half gravity would have a room context value of 9 (out of 10). The environment that the person had to traverse to get to the test room, with its full sun, spacewalk exposure, with anti-radiation pills given 1 hour prior, may rate a 2 (out of 10) on the pre-test travel context environment. The person may have eaten high energy foods and liquids and had a fight with their wife so their pre-test contextual mental state is rated a 3 (out of 10). The location of the test room may be in a difficult-to-reach area, with no travel pods, with high exposure to radiation, and thus may have a location score of 2 (out of 10), and so on. Individual data elements can be combined in different ways to match the needs of the community, the participants, and the resources available, as well as course the complexity and hazardousness of the community itself. The context determination engine would be the mechanism(s) to "deal with" all the data collection, organization, processing, and application to a) holistically and in highly methodical fashion identify, set up measuring sensors and associated parameters, operate and collect data from the sensors, organize and store the data, process and analyze the data, and perform the comparisons, etc. to compare the results with baseline(s) of applicable data and adjust the data accordingly.

The context determination engine may be usable to tie into the operating functions associated with the various contextual elements in order to modify that environment as much as is practicable with the contextual conditions under which the baseline tests were run and the baseline data was collected. The context determination engine may perform its various functions by applying a context coordinate and scoring system that can more easily manage and apply the vast amounts of data that will be needed to be collected in these off-Earth, non-Earth, and specialty environments/communities.

As a simple example of how differences in entities can cause apples-to-apples comparisons challenges, many medicines have dosages based on the weight of the person being treated despite it really being the person's mass that really matters (mass does not change with gravity, but weight does). But the Moon's gravity is about 17% of the Earth's gravity, such that a 200-pound person on Earth would "weigh" 34 pounds on the lunar surface. Mars' gravity is approximately 38% of the Earth's gravity. Thus, a person on Mars would weigh close to double what he/she does on the Moon yet still be a fraction of their weight on Earth. And travelling in space has even less gravity depending on relative distance between the various planetary/Moon entities, the degree to which such entities affect each other and the person involved, and dynamic factors such as speed of travel and rotational momentum of the spaceship. Complicating the situation is to what degree, in this example, weightlessness is perceived versus net gravitational impacts being experienced, as well as the duration/rate of change in speed/acceleration/rotational momentum in the encapsulated vehicle containing the human (e.g., space capsule, International Space Station, etc.) being experienced and likely to be experienced in the near future. Indeed, the dynamically—even radically—changing contextual factors from literally one minute to the next in space travel can greatly complicate diagnosis and treatment of certain ailments, as well as determining appropriate actions (e.g., nutrition, hydration, etc.) to preempt ailments or (in the case of chronic diseases) not accelerate them. Similar challenges would occur in the preemption of new ailments, particularly for persons who may—but not for sure—have a higher-than-normal risk of physical/mental issues in certain types of circumstances/situations/context. Indeed, in space medicine there is a lot of unknowns about risks of various types of ailments, as there is so little human experience in space, and even less with those persons actually having become ill, and of those few little data about the specific context(s) within which the ailment occurred and progressed.

Further, even in "stable" environments on the Moon, Mars, etc., topography and/or altitude can have a much more significant effect on the human body than it does on Earth. So, as a human on Earth may have trouble adjusting from going from sea level to 10,000 feet, such an impact may occur at a much lower difference in increased altitude on the Moon or Mars, or account for related factors such as temperature. These factors do not even begin to encompass all the ways to attempt to control their environment in terms of controlled atmosphere, space suits, nutrition/nutritional supplements, and other changes to "normal" living that a human in space will need to adopt, many of which are unknown at this time. Factoring in the possibility of very different symptoms and contexts occurring for a given person for a given ailment on Earth versus in space, the need for flexibility, particularly for context-based medicine in space, becomes critically important, particularly as the numbers of humans in space grows, and the need for scale/volume as a key requirement comes into play in what has up to now been a very limited base (in terms of numbers of humans).

For many ailments, it is unknown how differences in environment (e.g., gravity, location, topology, atmosphere, internal versus external differences, etc.) will impact the detection of/accurate triage/diagnosis of, let alone and/or preemption treatment of many ailments/diseases. Only about 600 people have ever been at least in orbit above the Earth, with only 24 of them actually setting foot on the Moon, and only a handful having stayed in orbit over a year (and far less on the Moon—Apollo 11's astronauts stayed only 22 hours total on the Moon's surface). Given that the vast majority of this small selection of people went through very extensive medical screening prior to going Off-Earth, the list of ailments serving as the Off-Earth "ailment record" is thus very likely extremely small (if not publicized for various reasons). It is logical to view that assumptions (or presumed givens) of such detection and treatment of an ailment (disease, physiological problem or issue, mental state, etc.) may be vastly different Off-Earth than On-Earth, with the data needed to adjust/react/calibrate space medicine-related activities grossly inaccurate without detailed contextual understanding of the person's past, present, and future context. Further, it is almost a certainty that new kinds of ailments will be experienced Off-Earth, particularly with longer durations and eventually full-time (including being born Off-Earth) becoming more common place. Already it is known that bone and muscle mass changes with prolonged duration in space. Whether or not—and if so how and how much—this truly is a problem for persons staying Off-Earth for very extended periods of time (e.g., multiple years) is unknown (and particularly since most of the few associated problems that have been reported appear really to only manifest themselves upon the return to Earth, e.g., return to higher gravity). Other potential ailments, such as radiation-related ones, are little understood outside extreme situations such as power plant disasters and nuclear explosion tests; long-term, lower (yet still elevated relative to Earth) levels of exposure have by their nature gone unexplored for the most part. Even then, such investigations by their nature have been mostly confined to Earth contexts.

Thus, the need to collect, analyze, and respond to data about different contexts that a person Off-Earth (e.g., Moon, Mars, asteroids, other planets/moons, space station(s), in transit travel in various forms, etc.) is experiencing, has experienced, and/or will be experiencing will be critical to the successful detection/diagnosis and treatment of an ailment. Further, since it will be a basic fact of life Off-Earth, at least for the foreseeable future, that resources (e.g., medicines, food/liquids, chemicals, treatment facilities, expertise/special skills, etc.) will be scarce, prevention/preemption of ailments will take on extreme importance. A person sick with ulcers or intestinal issues on the Earth may view them as a relatively minor annoyance for example; but on Mars it might be an eventual death sentence. Thus pre-emption, or at least as early-as-possible detection/diagnosis and treatment of ailments becomes essential Off-Earth, as well as environments on-Earth where the environment is very different and largely unknown in its impact on humans, such as underwater colonies or even the North and South Poles to some extent. Understanding context and having the flexibility to adjust to such contexts is paramount to this pre-emption and, as needed, preemption/detection/triage/diagnosis and treatment of a vast array of ailments. The medical disciplines involved will be widely varied, from radiology to pharmacology to dentistry to psychology, and involve probably every underlying enabler, from health care records to test equipment to testing methods and processing to storage of pharmaceuticals. The use of automated and human comparison mechanisms and controls using sensor/software-defined systems to rationalize the differences between various medical studies could become new areas of specialties themselves. For example, absent in today's medical devices are the capabilities needed to consider contextual elements such as the ambient atmosphere, pressure, atmospheric makeup, room temperature, gravity, etc. These elements/factors generally are assumed, considered a given, or even completely ignored when today's devices are designed, built, and operated. At best one or two factors, such as location or time, may be captured (even then they are often captured in a non-standard manner, such as St. Louis, Missouri on May 16, 1922 at 2 pm Central Time, instead of using specific WGS84 coordinates on UTC time). Even closely related physical measurements, such as blood pressure and pulse rate, often taken at the exact same time, are loosely coupled/linked in health care records.

By itself, the novel and innovative aspects disclosed herein include closely linking/coordinating heretofore unlinked/uncoupled measurements of a human and the addition of contextual dimensions to that data, as is the ability to use that contextual, in standard/consistent way(s), formats, and methodologies, to enable coordination/synchronization/comparison of the same/similar data elements in different entity environments. Historically there has been little attention to such systems/methods/technologies for reasons starting with the inability to get into space in the first place to the very small numbers of humans that actually do so, and their limited duration once in space. Further, there has been little-to-no attention paid to the ability for humans off Earth to be self-sufficient in practically any dimension; everything from food to medical device(s) were sourced from Earth. But as the number of and diversity of humans that are going into space in the next several years grows (and grows rapidly), as well as the almost exponential potential for ailments and other issues that will come with this scaling, diversity, and increased duration in space, as well as (eventually) the broadening array of entities possible for the humans to be located (the Moon, Mars, space stations, asteroids, various vessels, etc.), this heretofore small/no scale, highly "custom" approach to human "management," including medical needs, will need to give way to large-scale human support capabilities. This requires a heretofore unique collection of systems, methods, technologies, and mechanisms as disclosed herein and as illustrated in the below example.

A space traveler, say a female in her late 20s, prior to leaving Earth, is given a kidney ultrasound and mammogram, with "normal" results for Earth, her sex, and age. Her family history shows a slight elevated historical risk of later-age cancer issues, but nothing enough to prevent her from going to the Moon. She is going to stay on the Moon for 6 months, and during that time, at the 2-month and 4-month periods (at the International Space Station (ISS) and on the Moon, respectively), medical personnel want to repeat these tests to make sure nothing is abnormal. Comparing these tests will be problematic; the way the body will present itself in microgravity (or in this case in the ISS partial gravity depending on test site within the station, and the Moon's ⅙th gravity) is going to be very different, —the tissues will likely look differently in the test results. But has there really been a change? In this case, CAD (Computer-Aided Diagnostic) and/or simulations leveraging contextual data on all entities can be used to leverage capabilities like machine learning to compare these results and see if there is anything worrying, though the numbers of radiologists experienced in all three contexts will be counted on one hand for the near future, if any. These CAD/simulated results could be then used to make a clinical determination or at least inform the diagnostic process. This is a novel expanding of the current state of the art.

A similar scenario could be for pharmacological administration of drugs—on Earth key factors of dosage (and even drug selection) are weight, height, body mass index, blood pressure, etc. Again, all this information will present itself differently off Earth and could be influenced by things such as the entity's or entity's compartment's atmosphere and oxygen levels, or even the entity's relationship to other entities (such as a spaceship's location relative to the Earth and Moon at any given time in its travels). This will confound most doctors as they have to compare against Earth "normal", often with the base (Earth) data set having little to no contextual information with/against which to make adjustments for the space traveler's context. Again, the idea would be to use sensor and context-intensive solutions to help process and try and compare what's normal on the Moon, in microgravity, on Mars, and what is concerning/applicable for a given ailment in that current or future context. Indeed, diagnosing and treating ailments will be even further complicated in that "today's" context, or even "now" context, may not be the same in a day or even an hour, particularly for active space travelers. More generally, context-based capabilities for Earth-Off Earth research and development could be a ready user of exemplary embodiments of this invention, for example in pharmaceuticals, which all assume Earth conditions in their development processes.

For electronic health record (EHR) and electronic medical record (EMR) systems, a person's data would be harmonized such that the data could translatable across the journey through space. For example, during a 2-year journey to Mars with various contexts at a minimum, there would be Earth data, launch data, Earth-to-Moon data, flight to Mars under acceleration data, under deceleration data, orbit on Mars data, Martian surface data, and back again, for starters. All of the person's normal vital signs are going to manifest very differently under such conditions and solutions to assist in the monitoring and management is a novel innovation disclosed herein.

There are several keys or aspects to the ability to practice medicine off-Earth ("space medicine) as it relates to context understanding/determination, use case applicability, and overall need for dynamic updating and flexibility in widely, and potentially rapidly changing, situations and uses. These keys or aspects include the following.

Context-Adjusted Medical Records: Understanding of, protection of, "adjustment/coordination re-calibration" of health records between On-Earth basis and space (Off-Earth) context(s) encompassing not only past, present, but also future contexts.

Context-Based Testing: Incorporating context into the setup of, performance of, and capture of test results/data and all associated contextual elements, including calibration/adjustment of conducting the tests and/or measuring the results to be as close as possible to test data "ground truths" and adjustment of test results to compensate/reflect differences in test context(s) and ground truth(s).

Context-Based, Flexible Diagnosis and Treatment: Enabling dynamic, flexible, broad-based methods of pre-emption and/or treatment of ailments, including the use of AI/VR/AR (Artificial Intelligence/Virtual Reality/Augmented Realty, including concepts associated with Metaverse particularly for mental health-related issues) to adjust for/reflect differences/new considerations between On-Earth and Off-Earth (as well as involving unusual contexts on Earth).

Context-Intensive Continual Learning: Enabling context-intensive continual learning, particularly machine-based learning (e.g., Artificial intelligence, Expert System, Virtual/Augmented Reality, Metaverse, Simulations, Dynamic Modeling, etc.) to collect and analyze historical and current patient data, other patient data (including contextual data), and projections/simulations to adjust/refine/improve ailment diagnosis and treatments, particularly as they need to be done in "abnormal" and/or highly dynamic contexts.

Use of Integration of, and Dynamic Use of Multiple Architecture Environments: Use of multiple data collection, analysis, computing, communications, and user interface/interaction environments for administering tests/diagnoses/treatments, including physical, virtual, metaverse, and hybrid environments in On-Earth, Off-Earth, localized/non-localized, and/or hybrid situations to reflect different use cases, computer/communications capabilities and constraints, degree of urgency, methods for user interfacing/interaction, and complexity and scalability (including multiple people/multiple entity aliments). Unlike typical computing needs which assume a "stable"/known computer architecture to execute certain functionality, what architectural components and the associated systems, applications, and technologies involved may vary depending on context (even within a given use case or application), requiring "context-leading" detection of key triggers to dynamically switch between one/one set of computer/application/system components and a different one, even involving switching between architectures located/centered on differing entities.

Extensive, Dynamic Use of Context-Focused Simulations: Use of computerized simulations to project/hypothesize/adjust/develop treatment alternatives for given contexts and/or different patient physical and/or mental ailments. This in particular involves extensive use of virtual and augmented reality, the metaverse, and/or machine learning/Artificial Intelligence to identify, setup, conduct/simulate, test, tailor/customize, and modify different mental, physical, and contextual variables so that potential diagnoses and/or treatments can be "tested" prior to actual application to the patient. Virtual/metaverse simulations in particular will have a wide variety of uses in mental health/psychotherapy diagnosis and treatment, as there will be far less opportunities Off-Earth to experience (in reality) types of/high volume/high variety of personal/interpersonal situations where mental health-related triggers and issues may manifest themselves in sufficient form, fashion, volume, scale, and context to enable accurate analysis and diagnosis. Accordingly, exemplary embodiments of this invention are configured with or include capabilities for "simulation" personal/interpersonal/other mental issue-triggering situations/contexts/environments/etc. in virtual/metaverse simulations, measuring the impact/results, and using the results for treatment and therapy. Further, many of these context-sensitive situations, particularly potential/actual emergencies, will need the ability to perform dynamic, real-time simulations to "pre-test" potential treatments with little/no historical basis, and/or to test/adapt to future rapidly changing contexts.

Local/Edge Computing: While the need for multiple architecture environments is acknowledged or recognized herein, the practicalities of Off-Earth applications are such that a key design requirement—if possible—is to have the maximum amount of local/edge computing and communications taking place as possible. This emphasis on local/localized/edge computing and communications architectures would include extensive use of personal/personalized sensors on, in/implanted, attached to, or otherwise as close physically and/or mentally to the person as possible, in as near real-time as possible. This includes real-time determination of what would be "closest" computer system given computing needs, communications delays, cost, etc.; such "closest" computing et al. capability would be more closest-context-fit versus geographical distance, for example. It also benefits from large-scale deployment of sensors/sensor arrays/data collection mechanisms in/on/attached to as many persons, place, and things off-Earth as possible, for use in context determination. This is a new computing concept selection of processing capability based on context versus predetermined/assumed architectures, such as client server architectures with established/known/dedicated servers and mechanisms to communicate between client and server.

Multi-Entity, Context-Focused Reference Systems: Providing for multi-context dimensional reference system(s) for synchronization/coordination/integration of geographically-diverse computing systems and enabling apples-to-apples comparisons/synchronization/use of data/data sets collected and/or used on multiple entities. Current reference systems On-Earth focus on location and time but little else, and generally only for On-Earth applications (or those rooted/anchored to On-Earth applications). New reference system(s) and method(s) are needed to address not only different location/time realities Off-Earth, but also to capture additional contextual information needed to fully capture situations/data needs Off-Earth, particularly as those situations/data needs need to be cross-referenced to/compared to On-Earth data. Gravity in particular may require its own special handling, including a specialized reference system based on a particular entity, entity interrelationship, and/or mineral element for example. Such reference systems would include greatly expanded, context focused variable sets, and include new/additional base origin reference points such as the Sun center-point, a particular Earth satellite/satellite system, and/or reference points focused on multi-entity coordination, e.g., Moon-to-Mars, Earth-to-Moon, etc. New reference systems based on the center of a given entity mass could be used, as well as center mass-to-center mass-based coordinate systems.

Each of the above aspects of space medicine are discussed next.

Health Records

Healthcare record management and utilization—and unification or at least coordination/synchronization/comparison—across large distances will be a particularly problematic issue encountering, for example, the dichotomy between today's fragmented/decentralized (even scattered) health care/patient records and the need to centralize, or at least synchronize and funnel, communications between dedicated/special communication channels between Earth and off-Earth sites. NASA or other companies will likely want detailed health records for safety and science (and even commercial and social) purposes. These records can become desynced and managing them from an information storage point of view will be a technical challenge. Some attempts are already being made at addressing this general issue, including IFPS (Interplanetary File System), a "distributed system for storing and accessing files, websites, applications, and data. Despite its name, this system is not specially adapted to the informational needs in space, nor the constraints that will occur with Earth-to-off-Earth communications, notably communications channels availability and bandwidth, power requirements, timing, and cost.

For a given health record, a system/method according to a claimed invention disclosed herein may be configured to capture every (or at least many) environmental/contextual elements/factor that might need to be used to calibrate or otherwise take into consideration when considering a health parameter (including but not limited to health history, exercise, nutrition, interaction with persons with transmittable diseases, etc. including attributes not commonly captured/monitored on Earth such as body fat, muscle mass, bone density, (near) real-time eye health, joint lubrication/arthritis indicators, blood sugar levels, oxygen absorption rates, liver function, sleep/sleep-related metrics, taste sensitivity, and so on) as well as the "upstream" factors that can lead to/trigger issues related to those physiological areas, and particularly if those health parameters/factors could be affected by off-Earth factors. Example off-Earth factors include (but are not limited to) gravity (weight), location (x, y, and z, particularly z (altitude), atmosphere (oxygen and carbon dioxide mixture/concentration, for example). These data elements and factors (particularly factors specific to a person's particular physical/mental condition) will need to be linked/indexed by patient, location date/time, distance (physical, virtual, hybrid, combinations), relationships, network topology/nodes, etc. The relationships of data elements between each other will need to be highly cross-indexed to support an array of mesh-type (highly interconnected and redundant) interrelationships between data elements, many relationships of which in On-Earth environments would have little to no practical space medicine utility but may be highly relevant in Off-Earth medicine.

As part of this context-data element hyper-networked world, there will be need for a variety of reference points and/or "ground truths" that allow mathematical comparisons and calibrations on data elements that heretofore had little or no reason to be compared or utilized in the same or similar context. On Earth, two common such reference points are with respect to time and location. On Earth, time is divided into date/time zones, with the most common way of comparing/"calibrating" such time using UTC (Universal Time Coordinated), the old equivalent of Greenwich Mean Time, with time down to the second "tracked" by a variety of atomic clocks across the globe. When comparing times across time zones (the "When", say Pacific Time to Eastern Time), the mathematical model generally uses a derivative to the UTC time to compensate for variance between the two zones (the difference of which can vary whether when in Standard or Daylight Savings Time, and even location). Similarly, a widely used way of referencing location (the "Where" of a data element) is the World Geodetic System 84 for providing latitude and longitude coordinates. Both of these existing time and location reference systems will have varying utility off Earth, and at a minimum need a sophisticated way of correcting/adjusting any given time/location data set at a given time for a given application for a given patient. More practically long-term, a new reference system(s) will be needed to incorporate varying time and location bases/systems to reflect changes that can occur in space, and even more importantly incorporate (other) contextual parameters that will in effect define all the key data elements relevant at a point in space at a particular time, as well as reflect the reality that some, even many of those parameters may change in the very near future, even seconds.

In addition to the need for integrating heretofore unlinked or (at best) loosely connected variables, key individual variables need to be expanded/extended to accommodate Off-Earth applications. A day is for example on Earth historically based on the Earth's revolution period of approximately 24 hours. And a Year on the period of time it takes for the Earth to orbit around the Sun. Such equivalent periods/cycles are different on Mars for example (a Mars year is 687 Earth days, and a Mars day is 24 hours, 37 minutes in Earth time) and may not even be applicable in some respects for the Moon, which combination of orbit and slow rotation and the Earth's gravity and tidal forces is such that the same side of the Moon is always facing the Earth. Further, time, due to effects related to various physics laws/theories, may not act the same. Thus, a time signal sent from Earth to space may actually become "distorted" and be a different time then the sending time plus travel time. This makes time precision-based equipment calculations potentially problematic, particularly when fractions of a second can make a significant difference in a particular measurement, and that many—even most—time-keeping mechanisms have inaccuracies that need to be periodically corrected. A system/method is needed to synchronize, correct, coordinate, or otherwise link different times between on-Earth and off-Earth systems, applications, use cases, technologies, etc.

Location coordinates also has its own "special" issues in space. Besides a location being on a different sphere or otherwise planet/mass-containing entity (or in the case of travel vessels or space stations, not on a significant mass entity at all, but affected by them), Off-Earth locations have additional elements/aspects/factors that many need to be accounted for and included as part of location "coordinates."

On Earth, to the extent there are variables that can change with location, they tend to be altitude/depth in nature, particularly with respect to atmospheric or water-depth pressures. Even then, those variances tend to come into play in specialized applications, such as adjusting atmospheric pressure in an airplane, or the equivalent in undersea vessels. Other factors, like radiation or oxygen levels, tend to be assumed or more likely not a general issue associated with a given location.

While Off-Earth, however, such assumptions/presumptions cannot be made or indeed may even be fatal to make incorrectly. There are all sorts of factors off-Earth that need to be more tightly tied to location than on Earth, such as radiation, pressure, oxygen levels, $CO_2$ levels, temperature (particularly in controlled environments and/or with an atmosphere), and light/light intensity are just a few. Further, while different than on Earth, these levels can vary, and vary significantly, even with very slight changes in on-entity location. Radiation levels on the Moon, for example, can vary greatly depending on the directness of the light from the Sun (e.g., the farther you are away from the most direct angle of the Sun, the lesser the radiation). A much more intense example of getting more of a sunburn at 2 pm in August than at 5 pm in October. But such location-based changes can occur even with a slight change in location and/or even time. For example, on space vessels, and likely on actual places for humans on the Moon/planets, the spaces (enclosures) will likely be very compartmentalized for safety and efficiency reasons. Thus, for example, sleeping quarters may have a much different atmospheric control system (and associated pressures) than storage areas. Growing areas may have a much different atmospheric content (and certainly radiation) than medical supplies compartments, etc. Some areas may need much longer light exposure than others (sleeping quarters for example may always have very dim lighting, versus growing areas), etc. Thus, location, even for very small area on the same body/ship, will have other "coordinates" beyond a latitude/longitude-type system to define that location.

See, for example, FIG. 20 that includes a table that includes different locations and variables that accompany the different locations. As shown in FIG. 20, as a natural consequence of being on/in a different entity, there are host of associated variables that accompany a given physical location (the physical space dimension of x, y, and z on a given entity).

For each of these, there may need to be a correctional/synchronization variable or variables to do any sort of comparison or coordination between locations, or equipment/processes. Further, there will likely be involved multiple location coordinate systems, using various location determination techniques/technologies, and having different (possibly related) reference base origin points, to capture location (and even time) on/at/in different entities, which in turn may influence how different contextual elements are captured/recorded in general and as they relate to location and/or time.

Location will need to be expanded, not only to reflect the absolute location of a given person/place/thing "localized" to its entity (e.g., the Moon, spaceship, etc.) but its relative location as compared to both other things on the entity but also relative to other entities, discussed shortly. This is complicated by the fact that every entity, at any given time, will likely be moving through space, and relative to each other, making common reference points problematic. There are various reference corrections possible; for example, it could use the location of the Sun (or the center of Galaxy, or the Sun in reference/relation to the center of the Galaxy) as the "ground truth", and subsequently measure location of an entity relative to that location. Or the Earth could be a reference point (with a particular x/y/z coordinate on Earth as "ground zero" reference point); this would simplify matters as it relates to Off-Earth to On-Earth comparisons. Additional adjustments would likely be needed to compensate for the continual moving of all entities; some sort of vector location system could be used to take both location and direction/speed/velocity into account in any reference/reference adjustment system(s). More on the need for new reference system(s) for space in general are described later herein.

Another aspect of this invention looks to specifically, and in (near) real-time, keep key medical records updated to reflect the context of a person ([particularly Off-Earth). A localized data store and/or computing system(s) would enable the continual/periodic/event-based update/recalibration/adjustment of key personal data elements based on context.

The need for context determination and use in various calculations, like space medicine, would be broad from a time dimension. Specifically, capture and adjustment for context could not only be present, but also past and future, for a variety of reasons. Since many ailments do not exhibit symptoms instantaneously but can be as a result of delayed exposure to a previous ailment causing trigger (say a spike in radiation a few days ago), the capture of historical context data can be critical in diagnosing (e.g., radiation exposure) and treatment (rate of delay in exhibiting symptoms, severeness of symptoms) relative to potential prior exposure. From a future perspective, the context that a space person is about to be exposed to and their ability to assimilate to that future context may well depend on what contexts they are coming from immediately before (e.g., present) as well as past, such as a change in oxygen concentrations (similar to the difference between someone traveling from 5000 feet above sea level to 10,000 feet, versus sea level to 10,000 feet without the time to acclimate).

Figure 1:
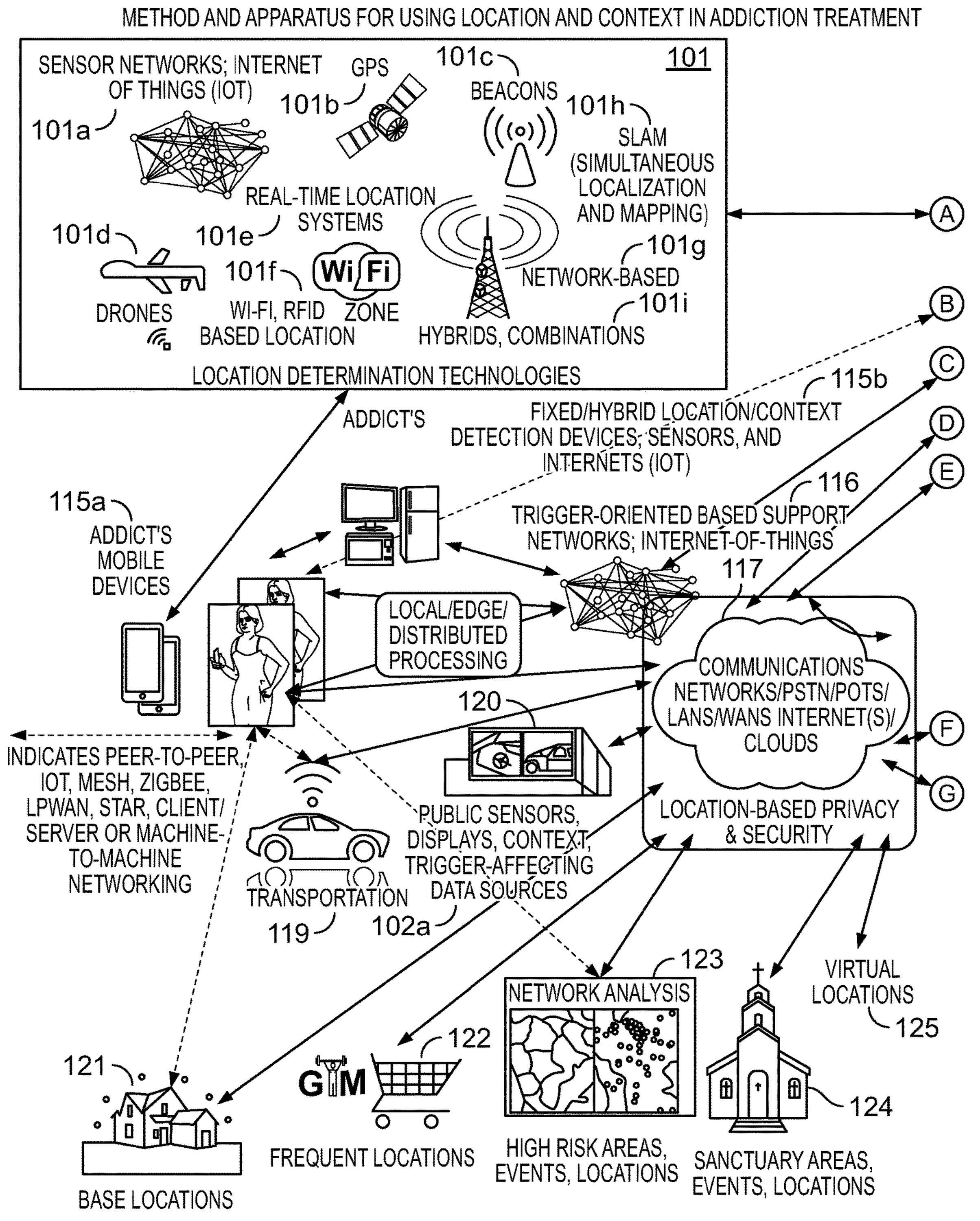
Figure 1:
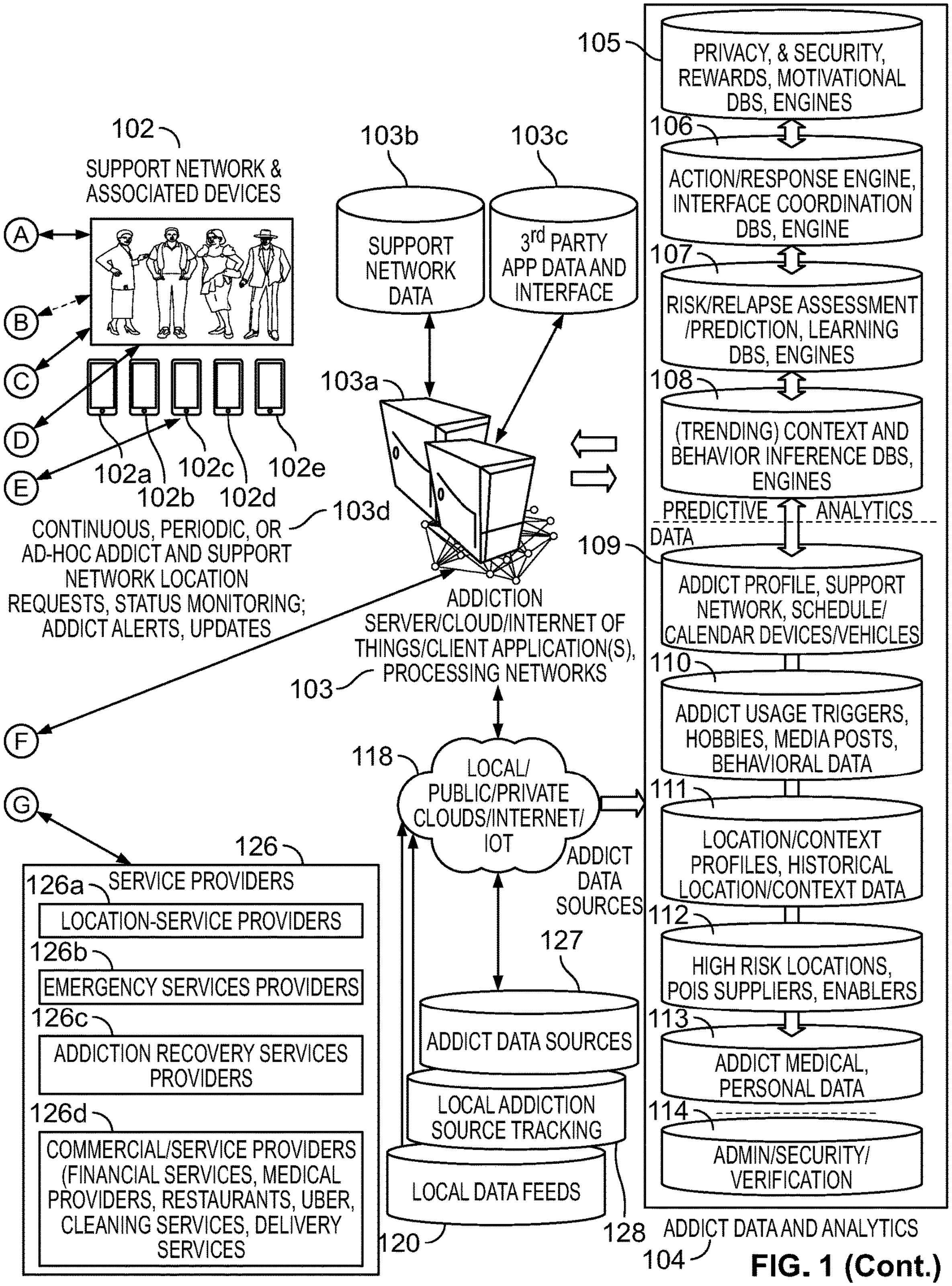
Figure 2:
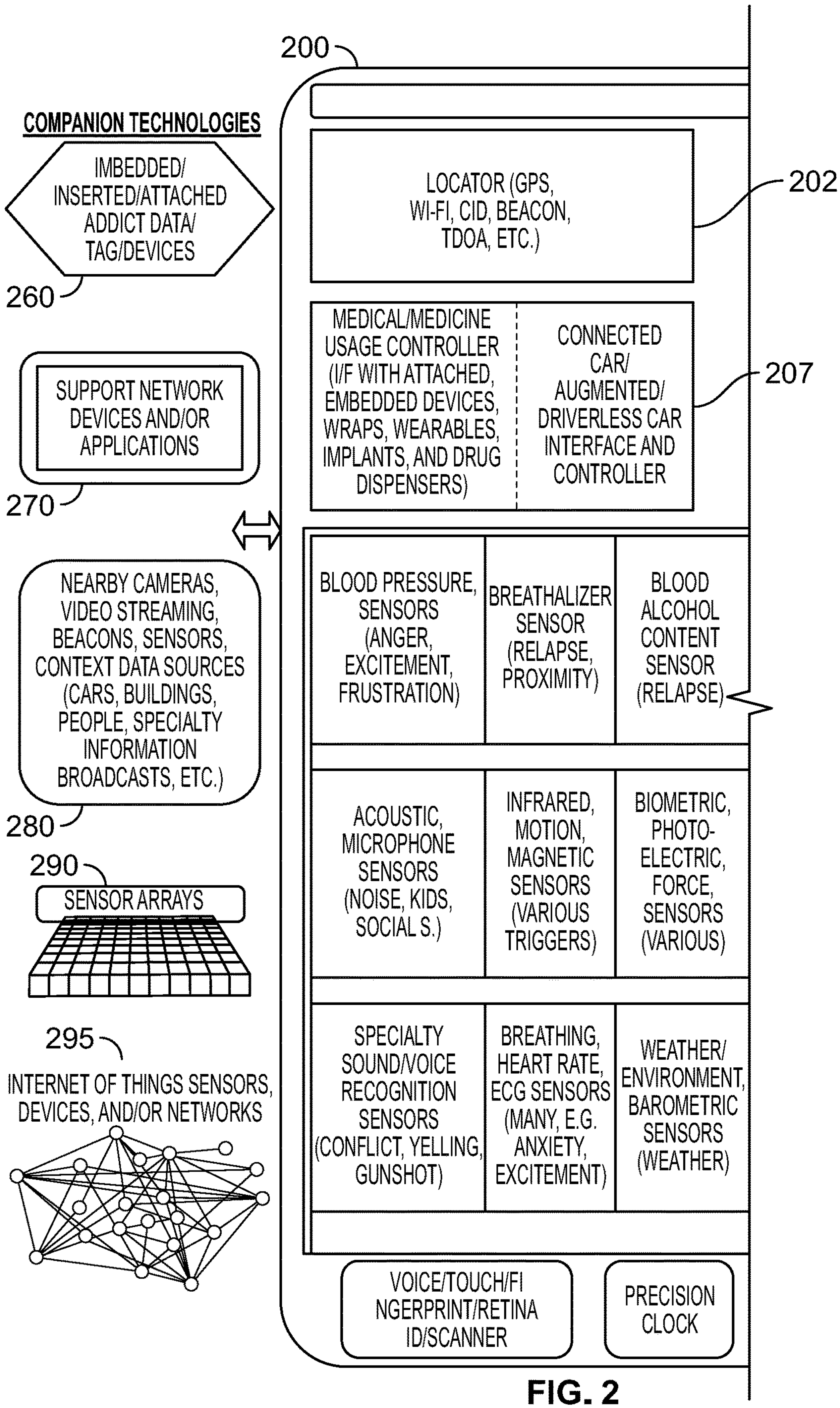
Figure 2:
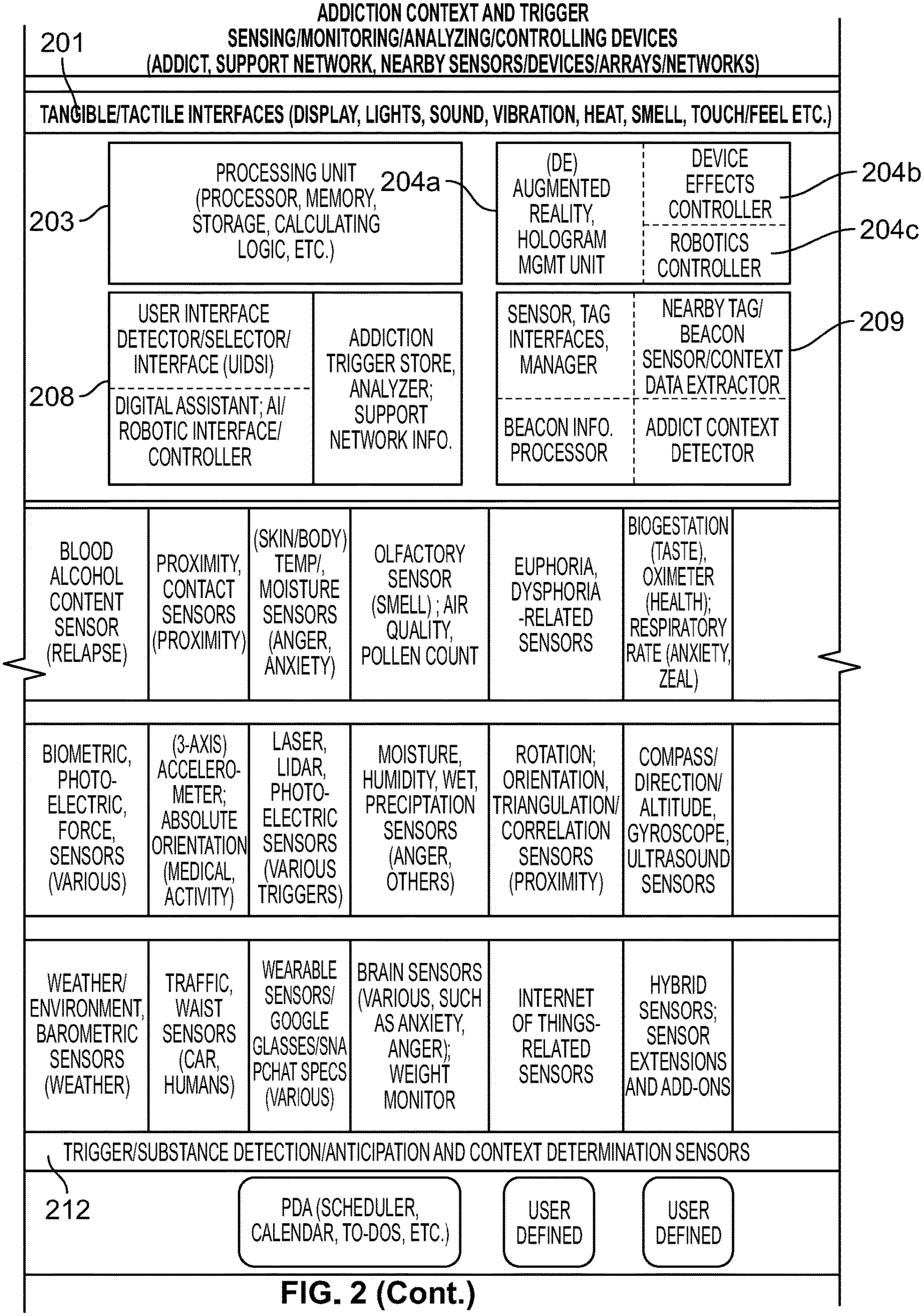
Figure 2:
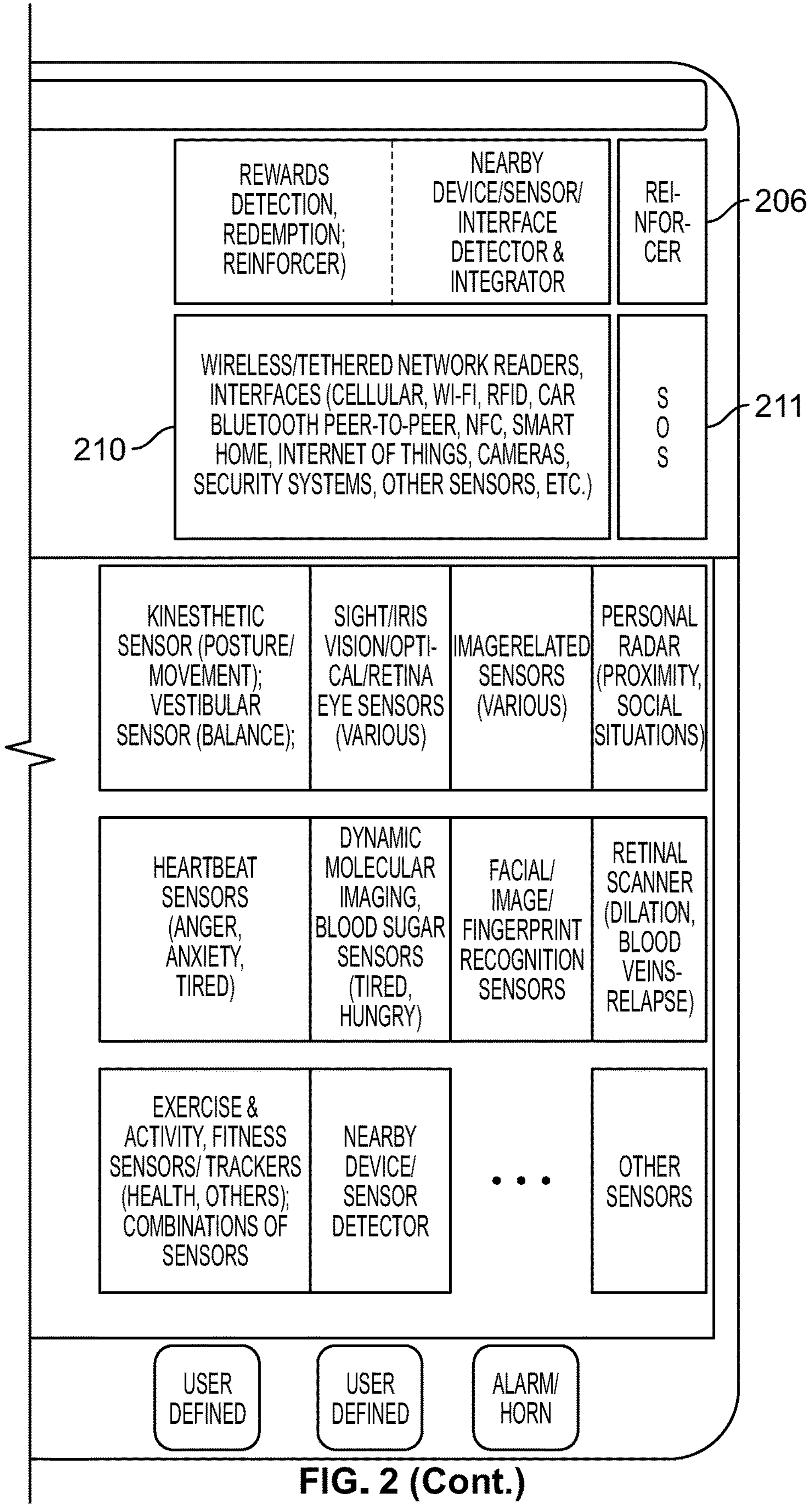
Figure 2A:
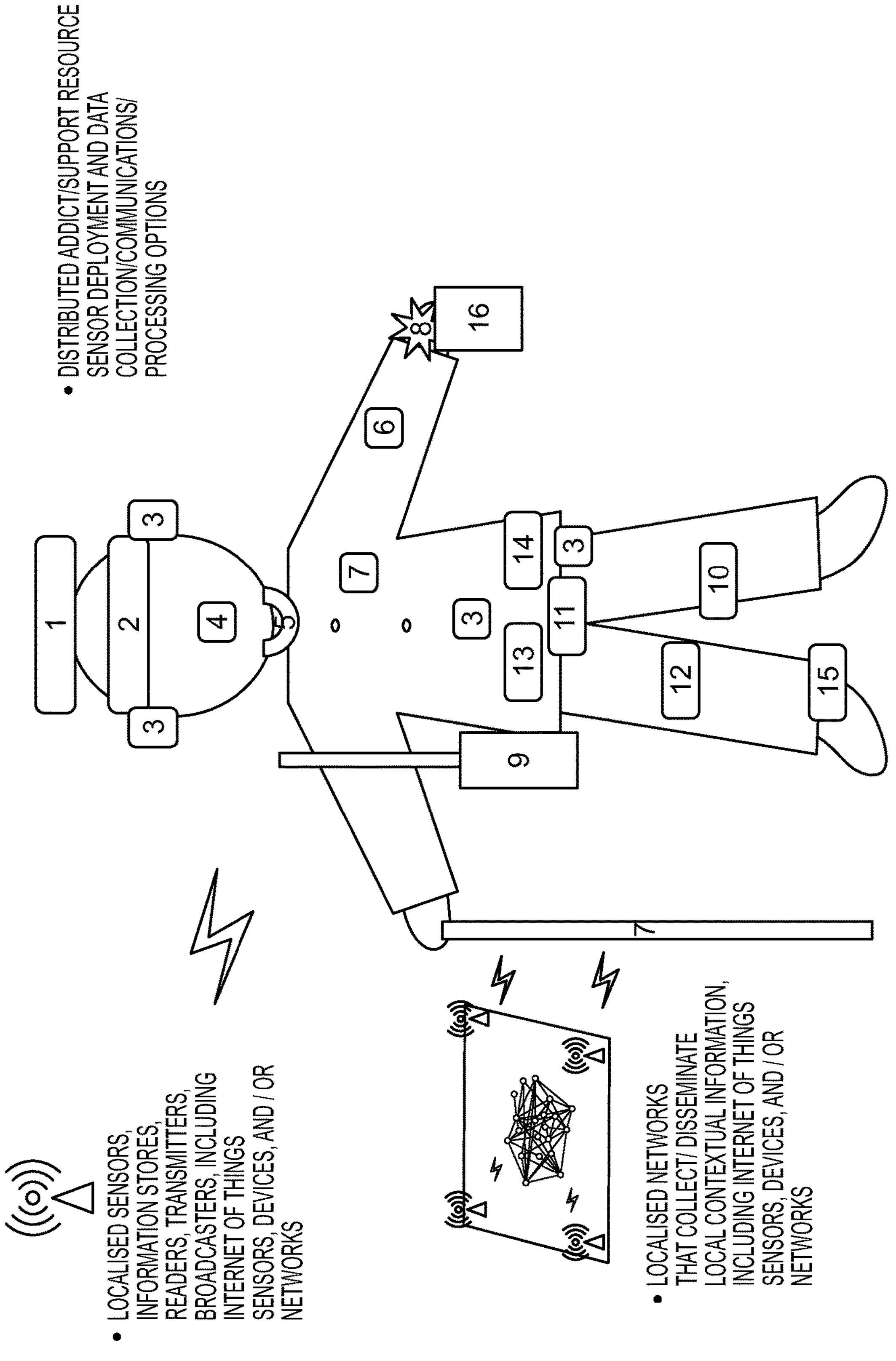
Figure 2B:
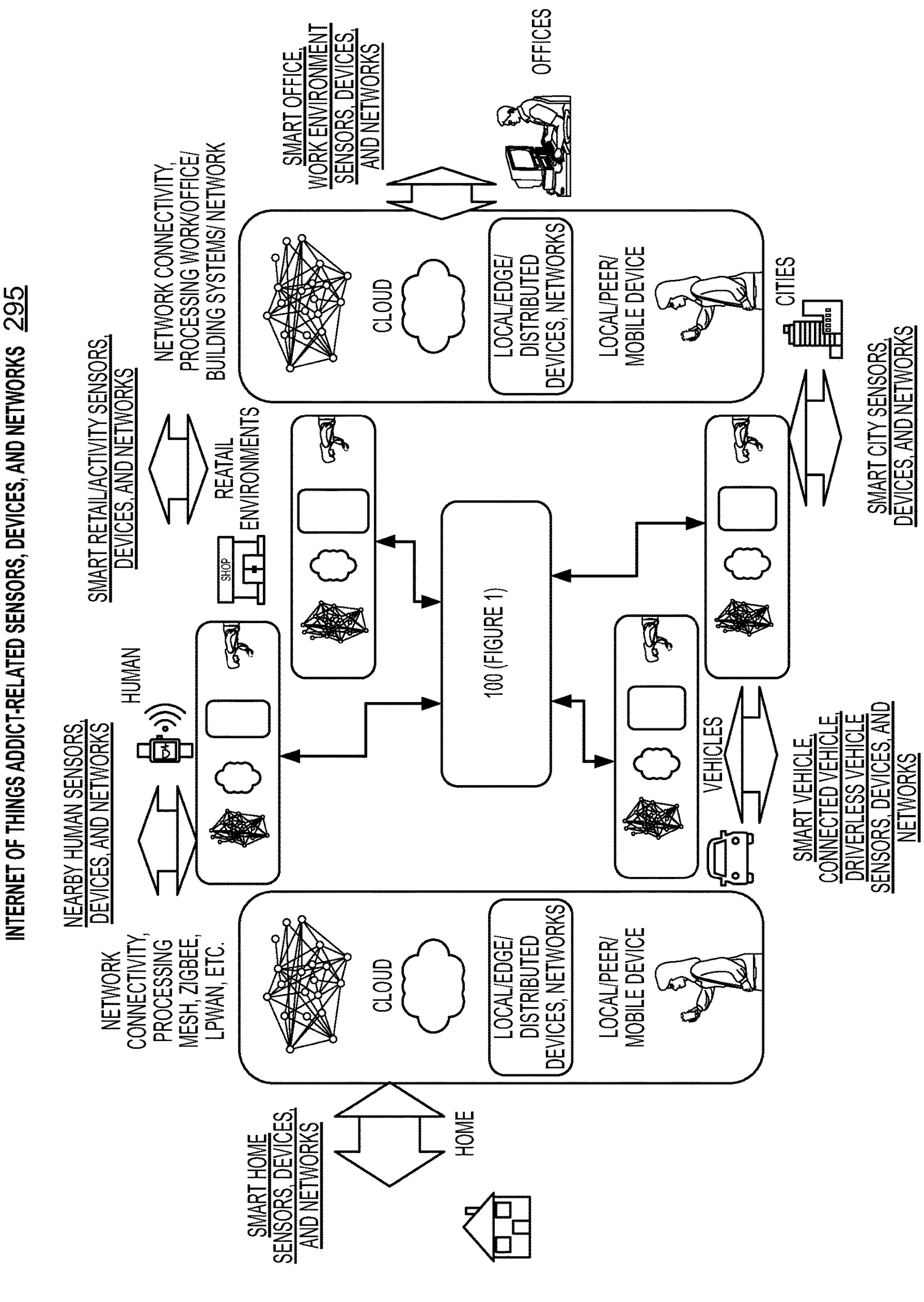
Figure 3:
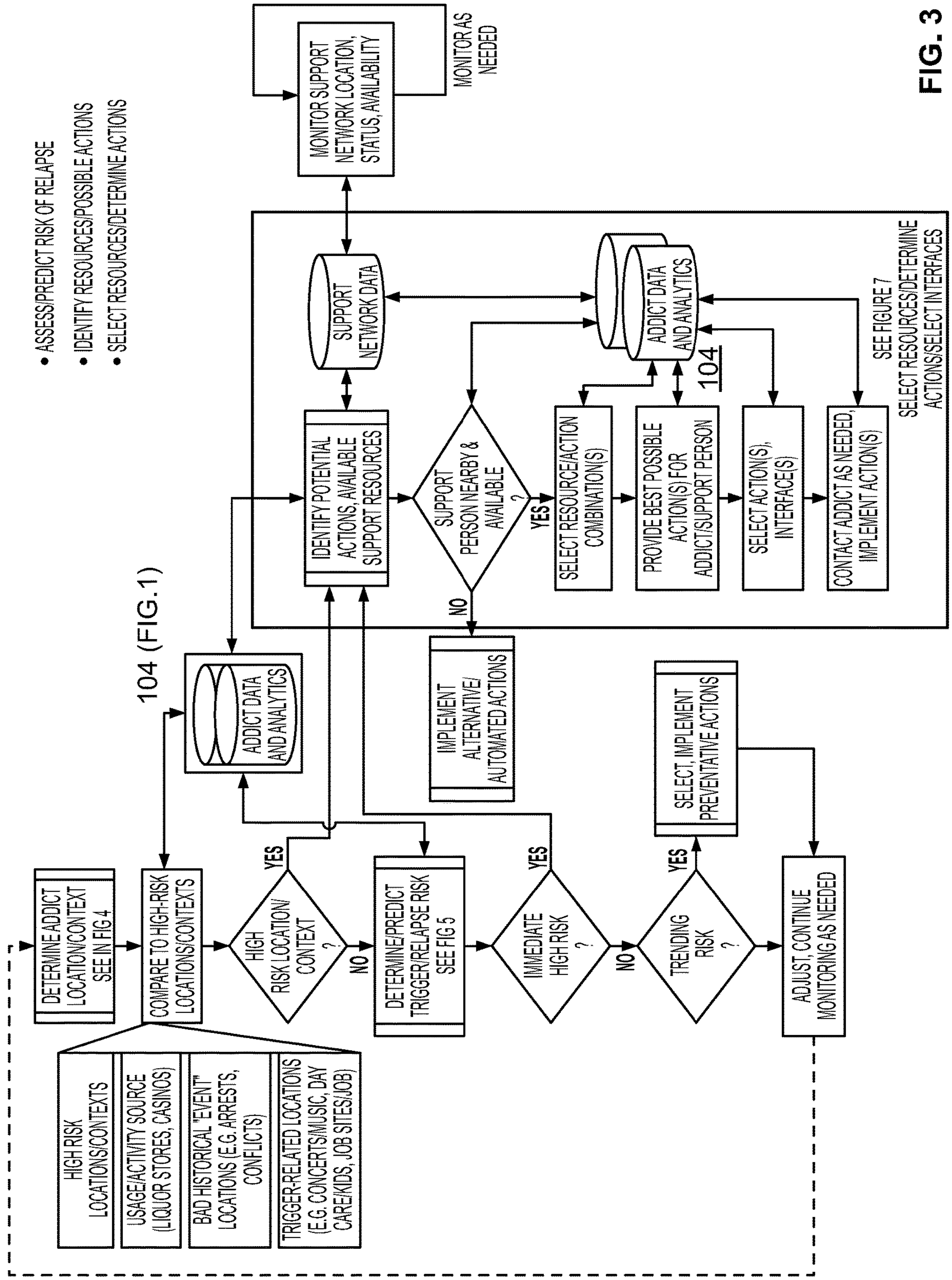
Figure 4:
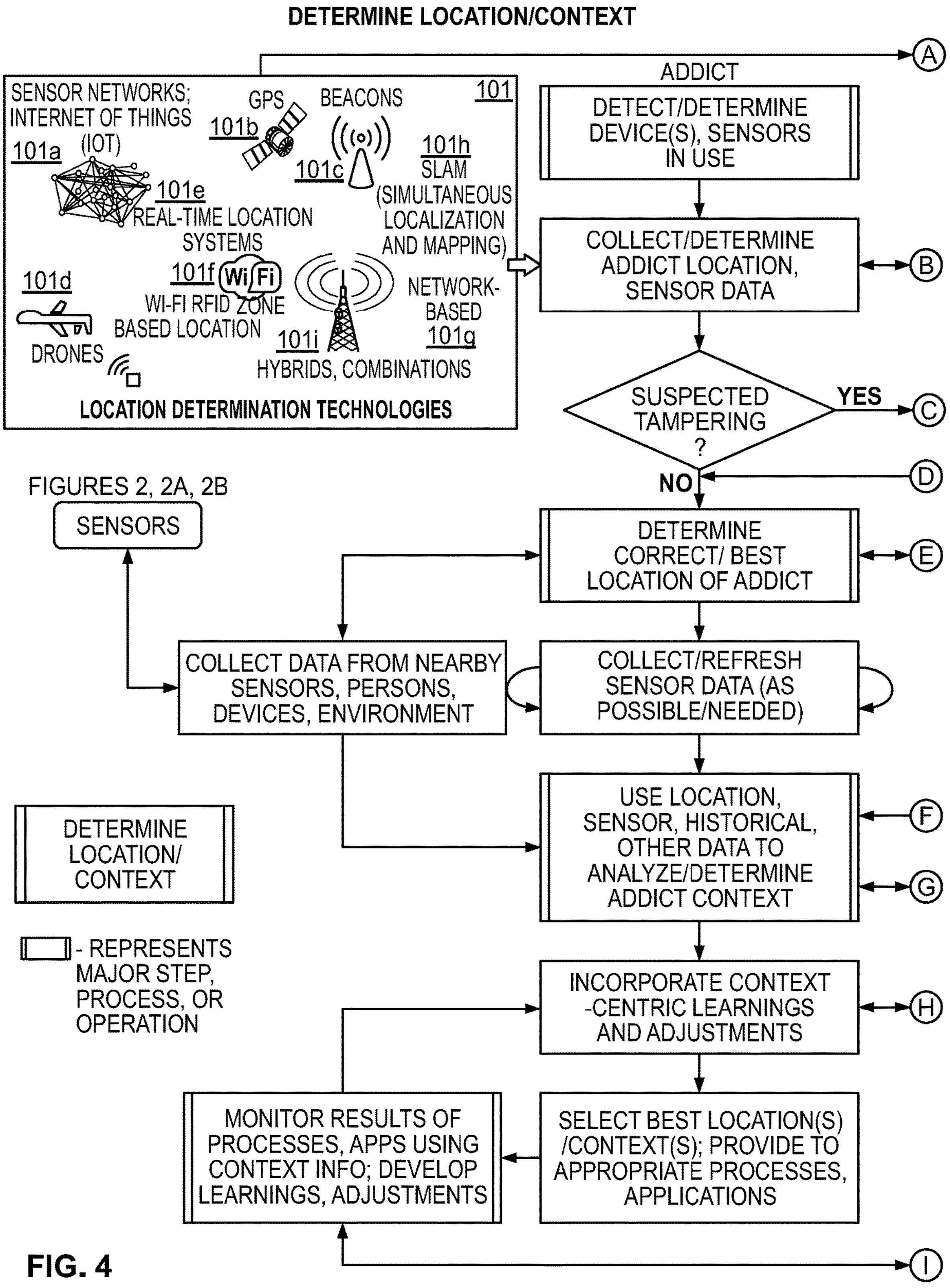
Figure 4:
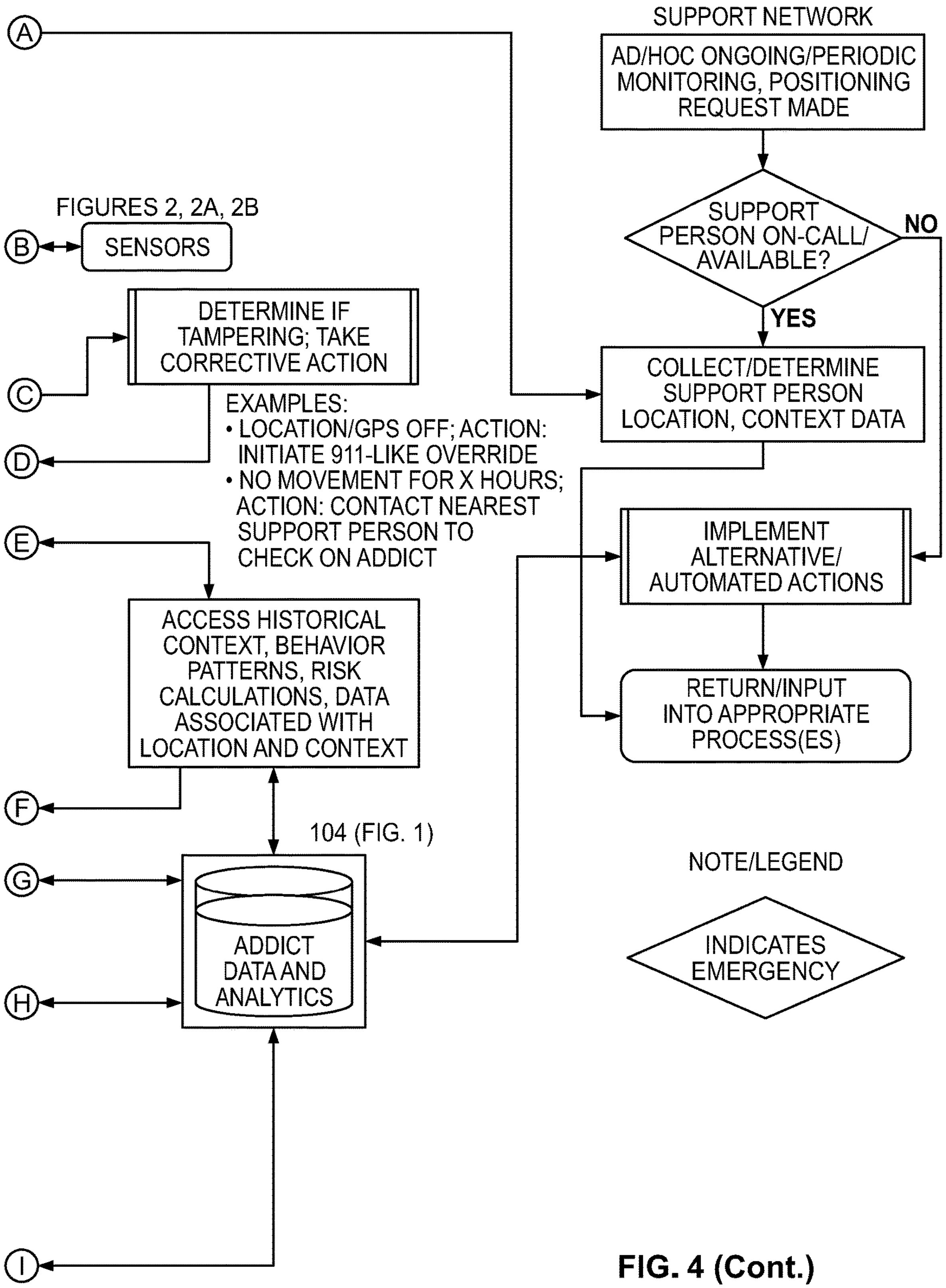
Figure 5:
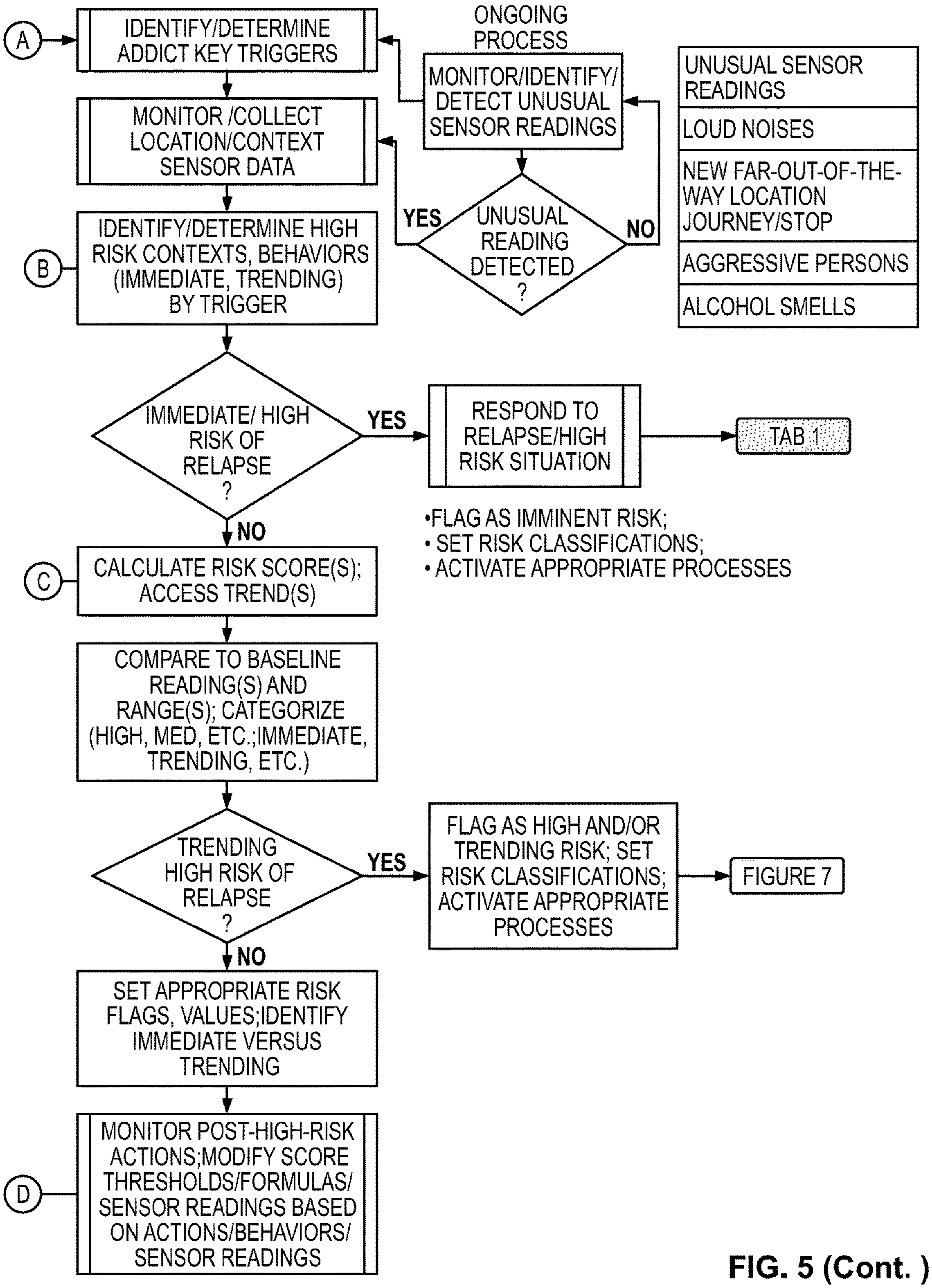
Figure 5A:
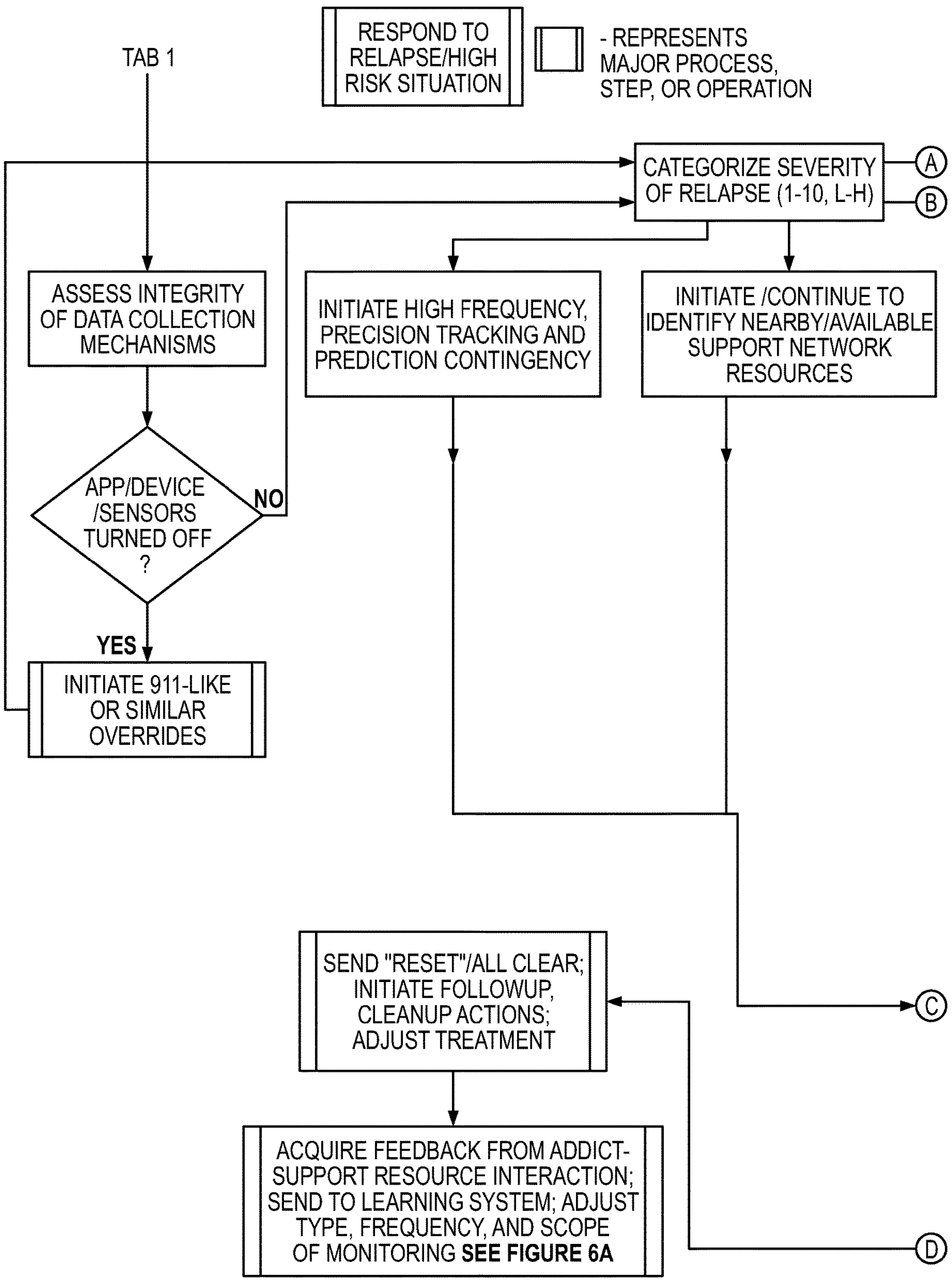
Figure 5A:
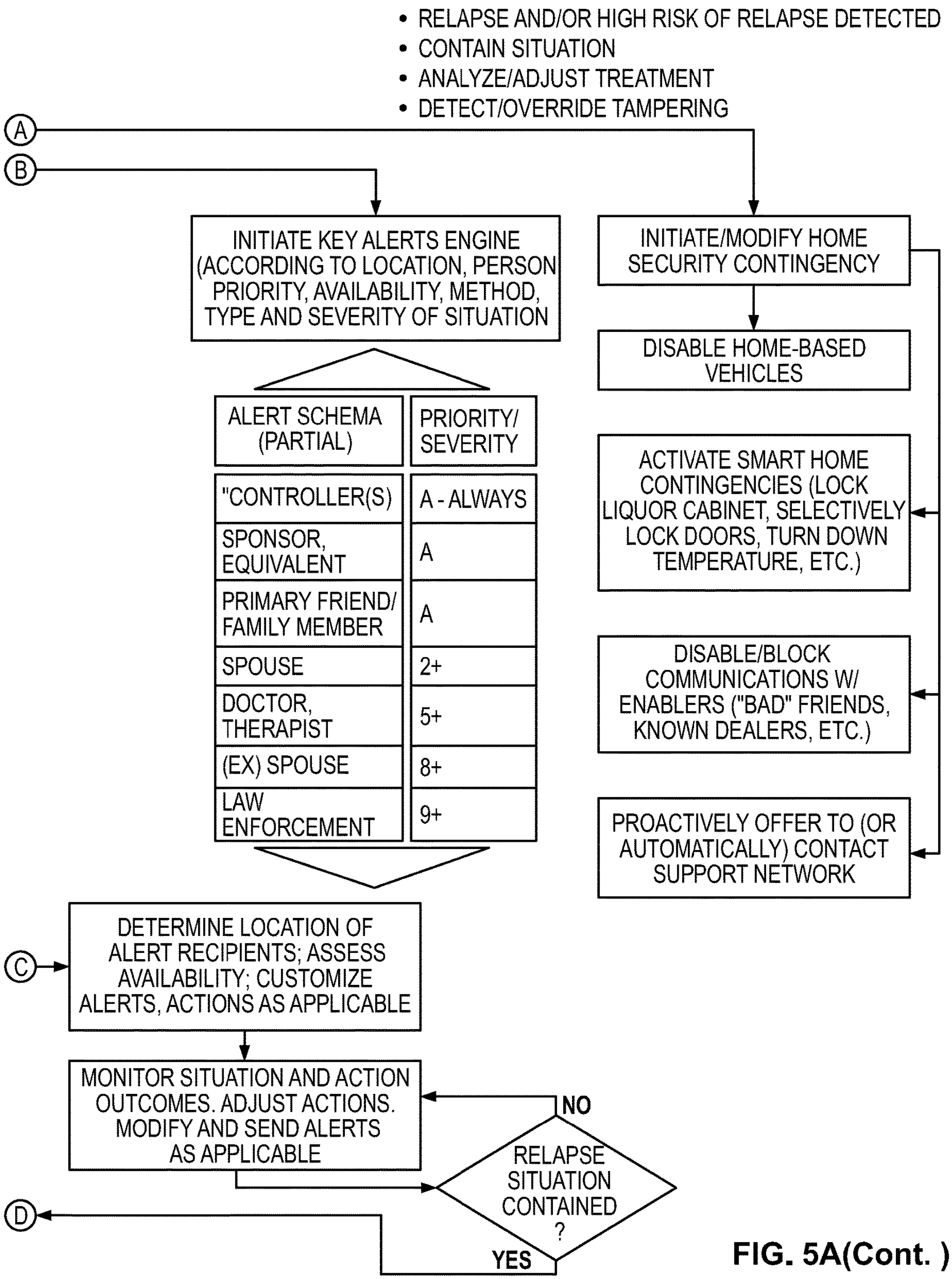
Figure 5B:
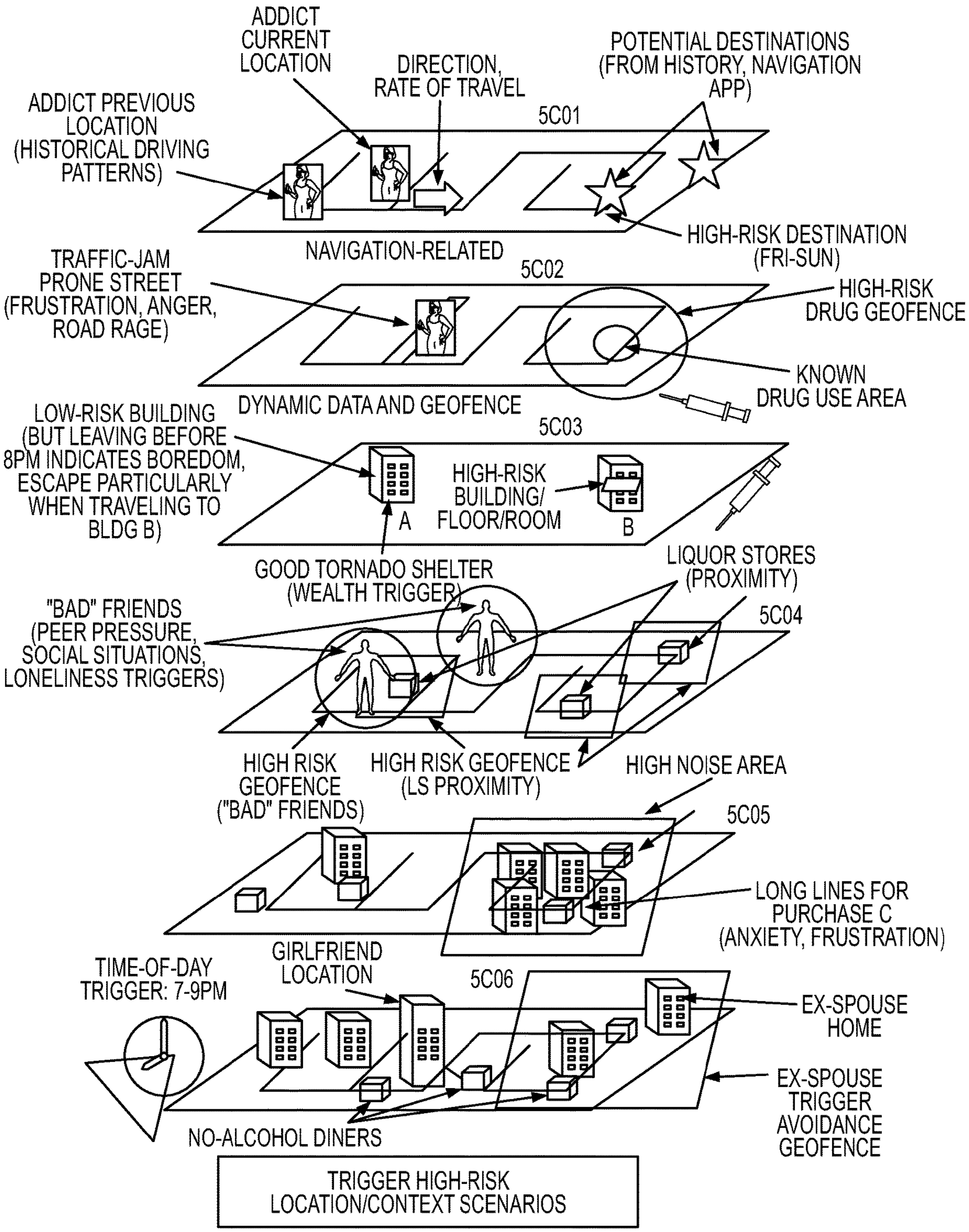
Figure 5B:
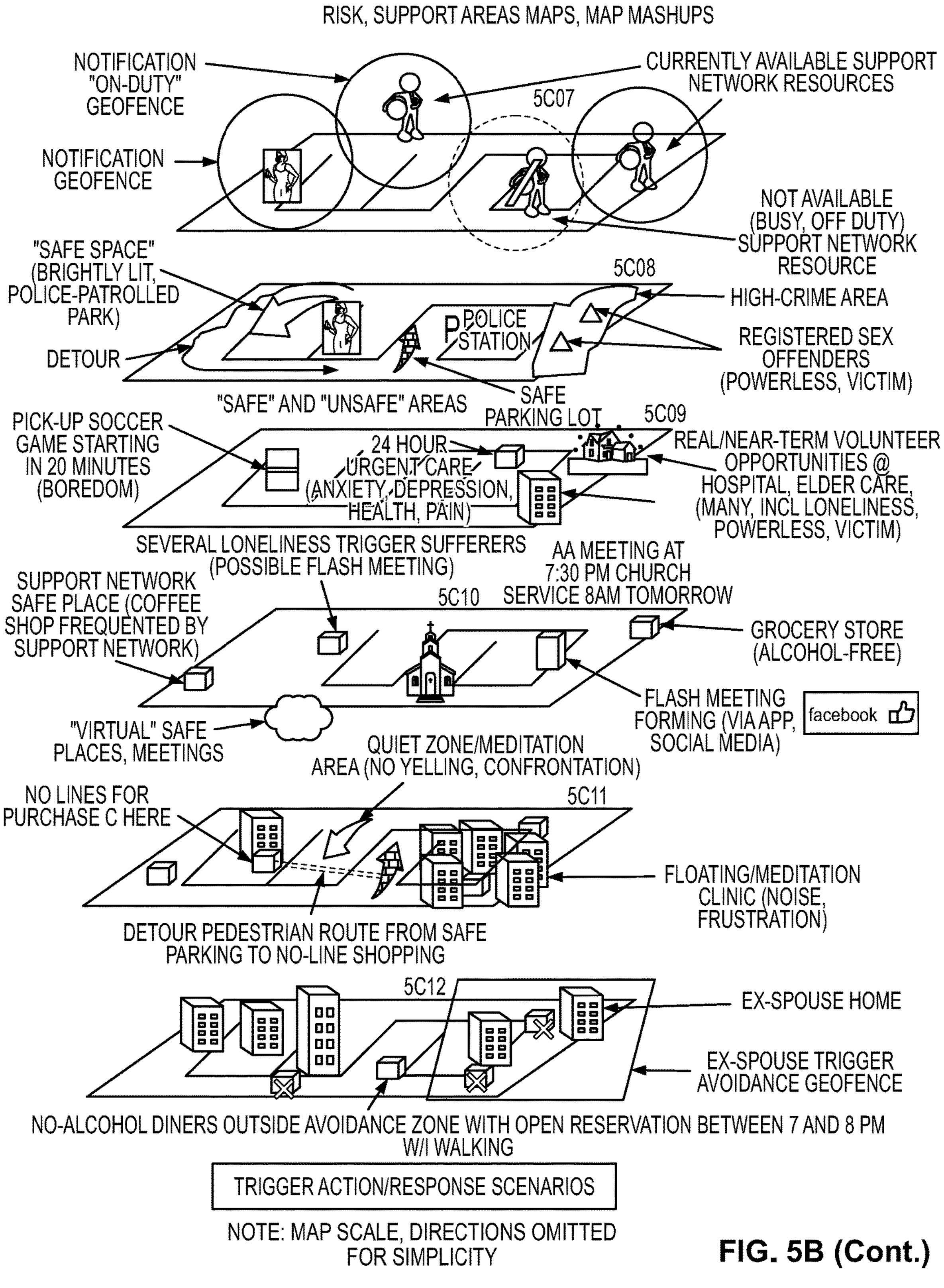
Figure 6:
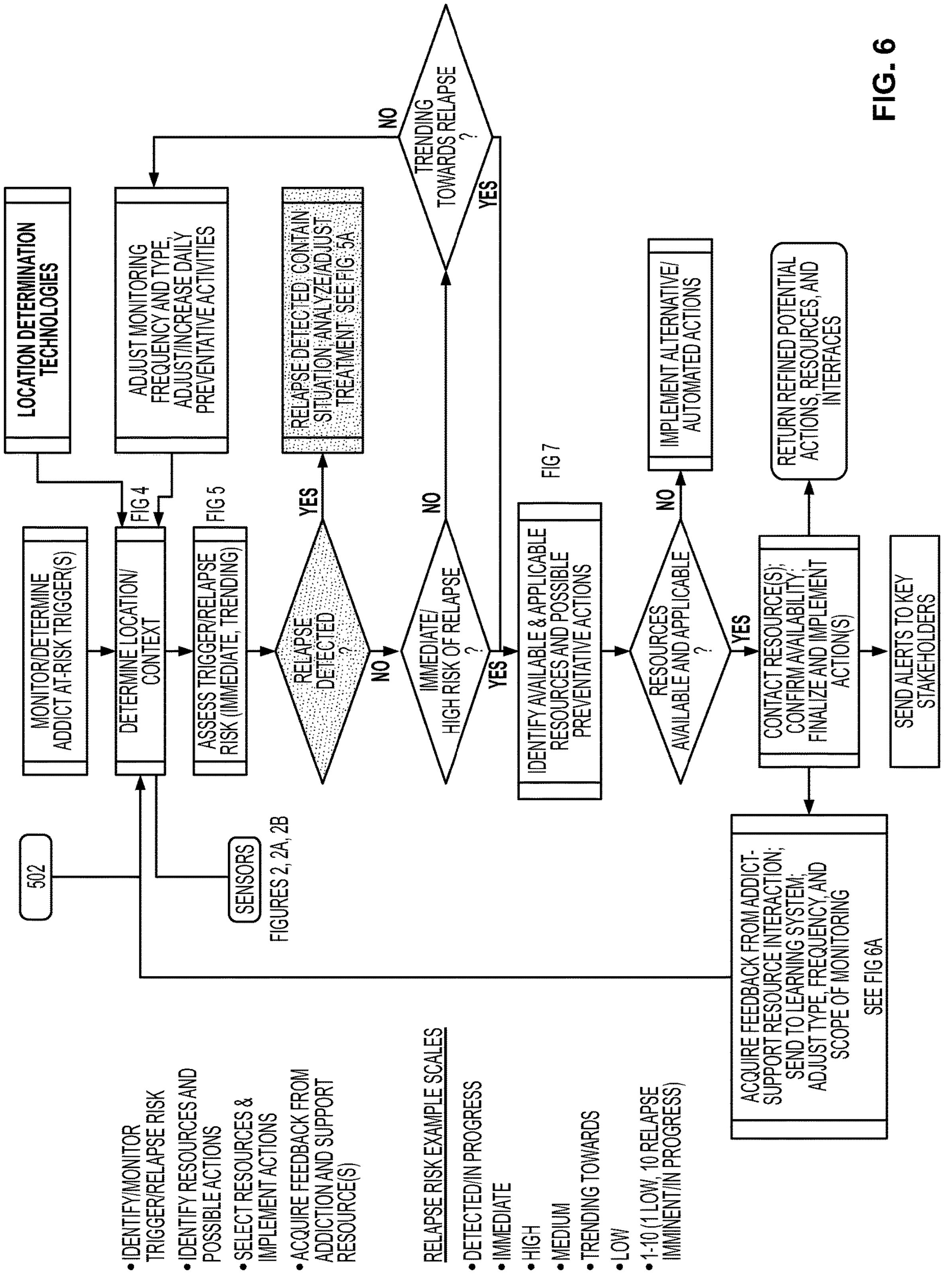
FIG. 6 depicts example ways to identify/monitor trigger/relapse risk and identifying, selecting, and implementing support resources and actions.
Figure 6A:
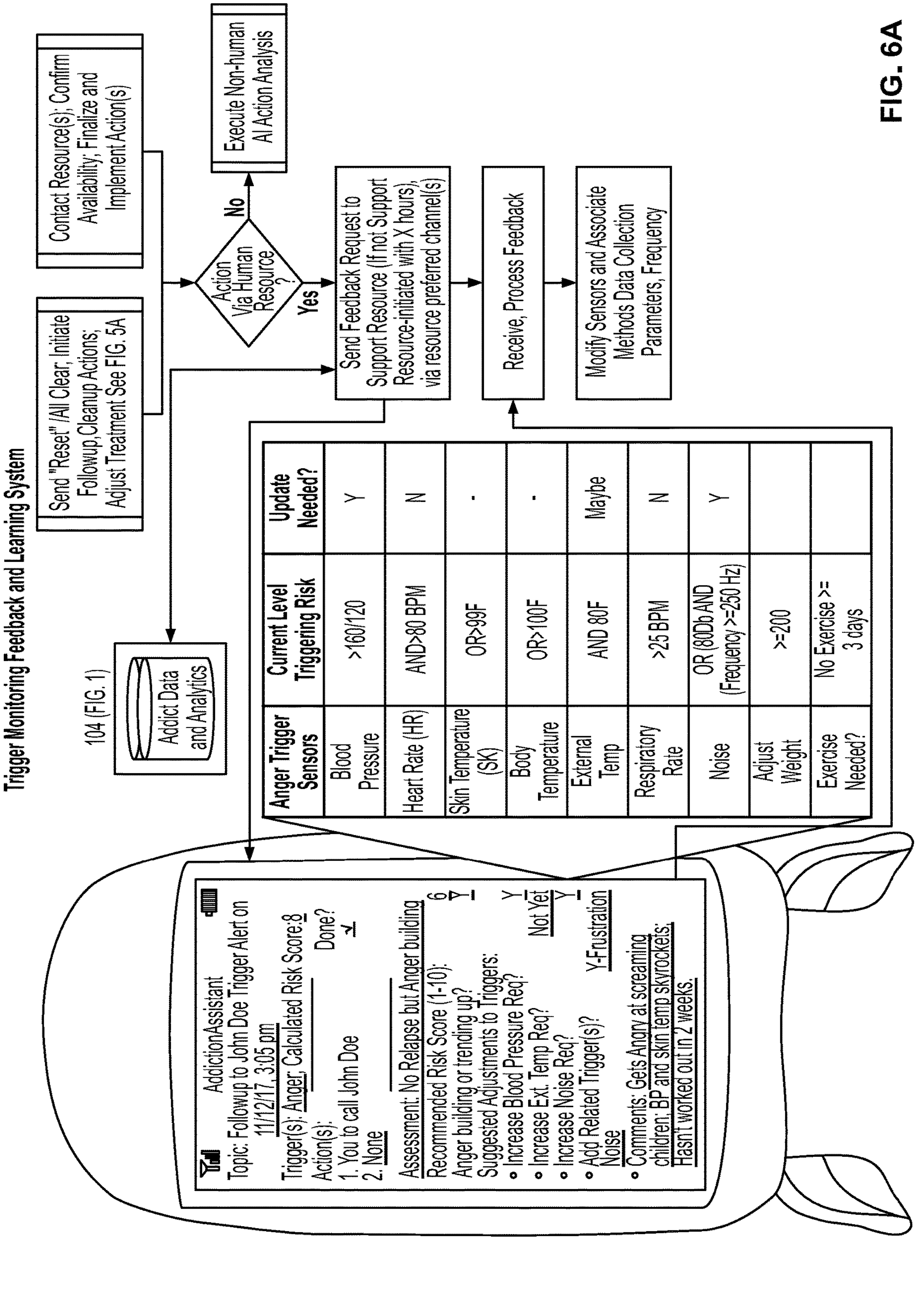
FIG. 6A depicts an exemplary embodiment of a trigger monitoring feedback and learning system.

The capabilities of doing this (near) real-time adjustment/recalibration/et al. would, for a wide variety of technical efficiency, speed, and localized sensor reasons benefit from being as near to the person as possible. If possible, the person would essentially be equipped with all the computing capacity to do such adjustments, or if not be able to communicate locally (e.g., at least on-entity, not off-entity) to do such calculations. Thus, powerful, context-sensitive "edge" computing in continual record recalibration would be a major computing/communication architecture enabler of exemplary embodiments of the invention disclosed herein, to avoid the various computing/communications delays/challenges associated with doing any sort of recalibration off-entity (e.g., on a different entity then the person is on at the moment), but also due to the need for each person to have a variety of sensors on, or at least very near, their person at all time. See, for example, FIGS. 2, 2A, and 2B.

That said, there will be situations/ailments when/where it will not be possible to do analysis/diagnosis/treatment "locally." In those situations, etc., the synchronization of records, including alternative/various decisions, including the combination of the information management and AI, will become critical on many respects. Not only will the synchronization/calibration/etc. of the "same" data elements/records captured in different contexts be critical, so will the documentation/capture about the process of analysis/diagnosis/treatment decisions, particularly with respect to how do these data get collected, how analyzed, how decisions get made, recommended, recorded, and ultimately communicated back to the entity/local medical resources/patient. The capture of information during this process, particularly how a particular treatment decision is made, will need to be captured more extensively than it is today, for a variety of reasons not the least of which is that many key variables/inputs are assumed, presumed, given, or not applicable in an On-Earth environment, any/all of which can be variables off-Earth. Further, there will be inevitable delays between when original data is sourced and treatment decisions are reached and communicated back to the patient. While communications with the Moon (from Earth) is near instantaneous (~3 seconds round trip), from the Earth to Mars is anywhere from 5 to 20 minutes (one way, depending on planetary positions), making real-time communications an impossibility, even in an emergency. That assumes no constraints on communications channels and channel bandwidth, e.g., transmitting a video/livestream can potentially be far more technically challenging/time consuming than just "texting" "take 2 aspirin and call me in the morning." Further, doing monitoring of the results/progress of a medical treatment/recommendation takes even more time and resources, particularly if a treatment may not work or have bad side effects, needing to potentially be adjusted as early as possible in the broader treatment process.

Thus, particularly in many emergency contexts, there will be great difficulty and in reality an impossibility of real-time diagnosis/treatment decision/treatment administering when any part of the process involves Earth-bound resources. And of course, emergencies delays can be detrimental/fatal. While any/many/all of "processes" related to an emergency (particularly any involving off-entity resources) are happening, local systems will need to gather context and information and likely autonomously report the information back to Earth/off-entity as any nearby persons/crew will in all likelihood be too busy to be relaying things via radio. The ability to use this adjusted data and machine learning/AI for various predictive systems, including simulations, will also be essential. For example, it can say well we think the AI is going to do this, so the Earth AI is then saying if X happens then choice A or choice Z are options to try and allow Earth support to get ahead or give options because they will be unable to know exact time and other contextual conditions. Supporting the above dynamic, context-centric data will require new ways of data management, distribution, updating, maintaining, access, and delivery, particularly given a) variations in time/location/context reference systems across entities/Off-Earth environments, b) the varying degrees of synchronization/coordination/use of such data elements across such environments, and c) the criticality of having much of this data as up-to-date/real-time as possible. Factoring in the practical cost, technical, and capacity considerations of synchronizing anything in an in off-Earth, non-Earth, and specialty environments, such data management challenges will be immense and require new techniques and innovative use of technologies as disclosed herein.

Test Application, Conducting, Measurement, Results, and Interpretation

As indicated above, the (in)ability to control a test environment will be a major space medicine challenge. In many instances, it will be very difficult if not impossible to control the context/environment of a test to adhere to key assumptions/premises, such as for example the impracticality (or even impossibility) of presuming a set gravity level while traveling between the Moon and Mars. Instead, the test results will need to capture as much information about the context/conditions that were occurring during the test and use this information to appropriately calibrate/adjust the results.

Doctors or advice providers may be impacted by imperfect tests, test results that are unclear due to unique gravity or environmental conditions, or data corruption or transmission issues could result in misinterpretation and/or misdiagnosis. To compensate, local records versus "source(s) of truth" will need to be incorporated, adjusting, coordinating, synchronizing, or otherwise enabling "apples-to-apples" comparisons in raw data, analysis techniques, results/results interpretation, and/or decisions. Decisions will need to be made as to what data (e.g., Earth data, spaceship data, a combination thereof) will be the source of truth in what cases. Nutrition management or genomic data may be from Earth where supercomputers can run calculations, but perhaps blood pressure would be from the target onsite as examples. Indeed, managing the different data sources, contexts, test environments, processing environments, data/processing architecture distribution, and reference systems will be an extremely complex "issue" requiring innovative techniques to effectively manage as disclosed herein.

Medicine Practitioner Education, Training, Reference, and Assistance

The training of, and scope of that training, medical practitioners will likely vastly grow in scope and scale for space medicine, as the need for expertise not only in medicine (or medicine specialties) grows, so will the criticality of knowledge about heretofore "unessential" disciplines such as astrophysics, (space) environmental sciences. Outside a relatively few geniuses or life-long space practitioners, it is probably unreasonable to expect that the full scope and scale of knowledge for a space-related/impacted medical discipline—even a specialized one—can be concentrated in a single individual. Thus, the ability to collaborate—across multiple practitioners and support capabilities (discussed shortly)—in/for a given context(s) will be a key part of space medicine. There will be at least two "flavors" of space medicine that will need to be supported and are enabled by exemplary embodiments of this invention: 1) utilizing traditional" physicians (if highly trained) supported by various tools/capabilities (described elsewhere herein); and 2) the ability to support "self-help", or more accurately, self-help in conjunction with more personalized tools and machine learning/diagnosis/treatment capabilities.

More generally, a scarcity of physicians, or at least a scarcity of physicians with the individual knowledge to assess, diagnosis, and treat the myriad and complexity of Off-Earth ailments, should be presumed. Further, if the medical professionals become sick or overwhelmed (such as in a space COVID scenario), the rest of the crew/human population may need to rely on reference guides to support them in responding to issues. This could be in the form of localized texts, some sort of space medicine wiki, or artificial intelligence amongst others. The use of artificial intelligence (AI) in particular could have high utility. Using personal real-time, context adjusted readings from person sensors and edge computing (described earlier and more later), could enable various AI guidance situations. More broadly, the ability to have a local reference management capability will be important to have local copies both digital and physical to help address, these guides will need to be carefully curated to handle likely many different environments, gravities, atmospheres and unusual possible problems. Further, the ability to have, and support, "AI Doctor/Surgeon/PA/Nurse"-type practitioners will become more critical the more complex an issue, the scarcer off-Earth resources become, the farther away (from Earth) the patient is, and the more time consuming/problematic communications with "nearer" (to Earth) knowledgeable resources become. As a practical necessity as well as providing human-like capabilities, the need for AI on different levels may be beneficial—it is possible that computational power may be limited, but also from a crew interaction interface having different personas—even if it's all computers, may help with a user experience perspective.

Gravity Management in general will be a huge issue for medical practitioners. One idea is to have this idea of gravity and environmental conditions being recorded into EHR/EMR systems. This contextual information is never captured in a doctor's office but is essential in space medicine. This information can be validated and observed and will be essential input into other technology or decisions. This includes:

- AI system that adapts to gravity conditions—microgravity—$\frac{1}{6}^{th}$ on Moon, $\frac{1}{3}^{rd}$ on Mars, etc.
- Atmosphere
- Hydration levels
- Vital Signs expressions—heat rate or O2 may be different depending on a slew of factors—what is normal—but more importantly what is normal, under these environmental conditions? Use of machine learning to identify what is normal as it is currently unknown.

Also, Computer Assisted Diagnostic with Gravity assessment and simulation, particularly in radiology but other systems as well will be key or important. These include recognizing that:

- Body will present differently in other gravity, things like a mammogram (MG), an ultrasound (US), a CAT (CT)

scan and others will all show abnormal conditions compared to what Earth-based CAD are set for. The system will be configured to understand this and modify.

Ability to compare using AI/CAD for different gravity—Earth based ultrasound was X before leaving, now it is Y in space—ability to understand what part of that delta is normal versus abnormal, as well as using it to train AI/ML in progress.

Medication Guidance/Consultation may be radically altered off-Earth. Similar to radiology, medication decisions will need to be made based on availability, individual need, treatment protocols, and all of these need to be made and understood with environmental factors in mind. Gravity, atmosphere, or physical condition may all require more, less, or different medications. Use of machine learning to track and record these to monitor patient health and improve and inform future treatments, including drug dosage recommendations. It will very likely be difficult for Human or machine doctors to understand what drugs will work in non-Earth settings, impacting recommendations as well as risk assessment. For example, a dosage on Earth may be OK but in space may cause cardiac arrest or vice versa.

Ability to handle unknowns and update shared medical database

Extensive Use of Context-Focused Simulations

Enabling and supporting the use of computerized simulations to project/hypothesize/adjust/develop treatment alternatives for given contexts and/or different patient physical and/or mental ailments is a key part of exemplary embodiments of this invention. This, in particular, involves extensive use of virtual and augmented reality, the metaverse, and/or machine learning/Artificial Intelligence (AI) to identify, setup, conduct/simulate, test, tailor/customize, and modify different mental, physical, and contextual variables so that potential diagnoses and/or treatments can be "tested" prior to actual application to the patient. Virtual/metaverse simulations will have a wide variety of uses in mental health/psychotherapy diagnosis and treatment, as there will be far less opportunities Off-Earth to experience (in reality) types of/high volume/high variety of personal/interpersonal situations where mental health-related triggers and issues may manifest themselves in sufficient form, fashion, volume, scale, and context to enable accurate analysis and diagnosis. Exemplary embodiments include capabilities for "simulation" personal/interpersonal/other mental issue-triggering situations/contexts/environments/etc. in virtual/metaverse simulations, measuring the impact/results, and using the results for treatment and therapy.

Like people on-Earth, persons Off-Earth will have a myriad of mental/mental-related/physical-mental combination issues that will affect them, both positively and negatively. The negative ones of course are of the most concern given the additional challenges and pressures that Off-Earth travel/living is likely to entail, as well as the limited resources and options available for treating or otherwise "dealing with" them.

As described in published U.S. Patent Application US2023/0007439 (which is incorporated herein), there are numerous triggers that can serve as the catalyst, driver, cause, or a contributor to a mental health issue, such addiction. Many of these triggers can be expected to also occur Off-Earth, such as Anxiety, Boredom, Depression, Loneliness, and so forth. Accordingly, aspects of the invention disclosed herein (e.g., use context-focused simulations, etc.) may be configured for use on Earth and off-Earth. Unlike on Earth (though, very possible in various specialty environments/situations on Earth), there may not be many, or even any opportunities for "testing" if certain triggers are causing/contributing to a particularly mental-related ailment. For example, the Social Settings trigger and Peer Pressure trigger, where a person who is afraid of crowds or even interactions with others, or feel undue pressure by them, will become anxious or even experience panic attacks, are likely to be more difficult to diagnose Off Earth due to the far fewer number of people there (at least for the foreseeable future), fewer opportunities/reasons to get together physically, and/or even just logistical obstacles (e.g., a room/atmosphere environment may only support a handful of people in one place at one time). But since social setting-related triggers can occur with just one other person in the first person's "space"/proximity, the trigger may nonetheless be possible in space. As people generally get use to fewer people in their proximity (versus what they experienced on Earth), such triggers may be "activated" in the presence of much fewer people, particularly the longer they are off-Earth/in low populated areas. But a therapist, for example, will have much fewer "data points" of social interaction from which to analyze/discuss with the patient to assess this trigger possibility, impact, trigger activation level, let alone treatment, so without simulations much of their analysis may be professional guessing in reality.

Towards that end, employing virtual reality, augmented reality, metaverse (including the use of friendly, unfriendly, person/place/thing, and other types of avatars), and similar "different" reality environments through various mechanisms is a way of exposing a patient to various situations and triggers and monitoring the impact on the patient. For example, using VR headsets, VR "rooms", or other simulation capabilities, the patient can seemingly be exposed to a party with a large number of people, when in reality there is no one there. Or it can augment an actual physical interaction (e.g., with 1 or 2 other people) via Augmented Reality to seem like there are several persons in the room in varying/dynamic proximity to the patient. Via various sensors in/on/by/around the person(s) involved, the reaction to this new "social stimuli" can be measured (e.g., monitoring for a jump or sudden significant increase in blood pressure and pulse rate) and used in various therapies, mechanisms, and methods, such as one or more of the systems, mechanisms, and methods disclosed in published U.S. Patent Application US2023/0007439, which is incorporated herein in its entirety.

This kind of capability would provide all sorts of options not possible in the "real" world (and thus be applicable also for on-Earth only applications). For example, it may be only a certain size and/or of crowd that triggers Anxiety in social settings. The simulation could gradually reduce/change the make-up of the crowd to detect any changes in Anxiety/Social Setting/Peer Pressure (for example)—related measurements, customized to that person (e.g., sweating, blood pressure/pulse rate/body/skin temperature above a certain level, shaking, change in voice volume/words used, etc.). All sorts of variations are possible. For example, the topics of conversation "said" by the "persons" could be modified. Key words or gestures or facial expressions could be incorporated into such virtual-type "conversations" with the impact on the patient measured in multiple ways to assess if, how, at what threshold, and in what context(s) they have a negative (or positive) impact on the patient, as measured by sensors, self-reported, reported by others, or other measurements/assessment mechanisms. Thus, if it is suspected that it is not the size of the crowd, by the conversation topics involved (or conversation topic in a crowd size of X to Y in size, and/or A to B in gender or age makeup, or some combination), that is causing patient Anxiety, Depression, or Stress, these hypotheses can be tested. There are no limits to the contextual factors that can be tested, helping to continually refine determining what their mental issue(s) trigger(s) are, how they are measured, what thresholds are their "breaking" (e.g., relapse) point, etc. Heretofore very difficult factors could be tested, such as lighting levels, room design, temperature, etc., or more complex factors such as person (specific or type) interactions in various contexts. Even physically real factors such as what the patient ate in the 24 hours prior could be incorporated (building on the idea that eating certain foods at certain times can have a mental health impact).

Such tests might help "discover" that social situations are not the cause of Anxiety in the person, but instead Loneliness (e.g., feeling alone in a crowd). Additionally, or alternatively, the various measurements/sensors used to measure various triggers could be adjusted based on the simulations (for example, ascertaining that body temperature is not an indicator of the person's Anxiety, but only Anger, or that a person is not really Angry unless the temperature rises at least 10% from his/her historical contextual baseline). Historical personal/group/identity/demographical information for various triggers and/or contexts can play a major part in formulating, conducting, and analyzing simulations.

In turn, treatments/approaches could be tested, changed, deleted, or modified. The concept of a "safe room" in a crowd could be tested (e.g., the patient "enters" the room thereby blocking out all Noise/visibility to others). If it has a major impact on a trigger(s), such "real" (or even virtual) safe rooms could be designed into the patient's life for future "real" encounters with those triggers. Even metaverse Avatars can be utilized. For example, a "safe" Avatar, or a virtual representation of a person's mother, etc. could be incorporated to ascertain a patient's reaction to an encounter with such (positively or negatively, or perhaps both depending on context). Avatars, particularly ones that the patient has been "conditioned" (via prior various exposure via various user interfaces) to associate with a mental condition (e.g., safe, evil, quiet, happy, etc.), commonly viewed as a "metaverse" concept, could have extensive utility in this innovation, even to the point of programming them with personalities so that various simulations could occur based on/focused on the conduct/behavior of the avatar itself, as well as the context(s) that the avatar is "operating" within.

This capability could include a dynamic, contextual-focused kind of Rorschach (ink blot) series of VR/AR/metaverse tests to collect data on what perceptions the patient "sees." Different people/places/types of places/things could be inserted into a simulated/partially simulated context to "test" the patient's reaction—not only to what he/she is seeing, but the context within which he/she is seeing it (e.g., do you see a spider in a neutral environment, Hitler when your boss is in the context, the Beach when no one but a tree is in the context, etc.).

Not only would context-based simulations be useful for mental health diagnosis and treatments, such capabilities could be used more broadly, ranging from effect isolation (mental health people "time out", temporary treatment/calming down of panic attacks, or even punishment of sorts, depending on situation/person/context), entertainment, and social enhancement (think a crew party while in reality each crew member is "trapped" in their work area, or interfacing with family back on Earth, with a festive/party atmosphere dynamically included in the augmented party, possibly even with virtual not-available family members in "attendance."). Dealing with the inevitable isolation issues that will occur in the early days of long-term-stay space travel will be a major use case, enabling for example the presence of an artificial friend—you can complain to your artificial friend and no one cares or convention is if you talk trash to the AI everyone just understands you're venting, etc. The ability to use Machine learning/AI to continually learn/test/improve these interactions will be key, as well as keeping many of them private/secure, as many of the data elements collected will likely be highly personal and have major negative ramifications if disclosed. Others, of course, will be needed to be "public" to facilitate various use cases and ensure the collective health and well-being of the crews.

The ability to simulate ailments would not be limited to mental ones. Physical ones could also be applicable. For example, the ability to simulate and project at any given time, a chronic condition based on historical changes to various stimuli/contexts/triggers could be one to attempt to preempt worsening of the condition by changing various contextual elements (e.g., nutrition, oxygen levels, exposure to stress, etc.). Recovering from a knee injury could be assessed in an augmented reality environment by projecting, based on current movements, likely future possible movements.

The ability to perform (near) simultaneous simulations on multiple entities may be beneficial in multiple respects, from improving computational algorithms to seeing if conducting simultaneous tests using the same contextual elements, then changing such elements (particularly "real" elements) to determine if there are any differences in projected outcomes—in other words, simultaneous simulations can identify and correct for real world changes. Again, such a capability would not be limited to physical and mental health, but other kinds of use cases such as off-Earth farming where there are many unknowns relative to agricultural practices on Earth. See, for example, the discussion of off-Earth farming and managing off-Earth and specialty community agriculture in U.S. Provisional Patent Application 63/460,523, which is incorporated herein by reference in their entirety.

With further regard for off-Earth farming, food supply is a critical factor gating human space habitation. It is not just the rocket equation that will hold us back it is also the food. Time in space means calories per day—4 pounds (2 kg) per person per day. (1,460 lb. or 730 kg a year). Other needs include medicine, entertainment, health, psychological support and more. To solve this problem, one or more of the following may be utilized including: Use ISRU (in situ resource utilization) transforming regolith into soils to shorten supply lines; Leverage Regenerative Agriculture techniques, like water harvesting or Microbiome management; Leverage Biology to reduce costs and equipment; Develop multiple revenue streams to support continued expansion; and Dovetail research to support regenerative improvements back on Earth. ISRU based food and bioproducts may be provided to support human exploration and habitation of space. This may include leveraging a life affirming regenerative approach developing biologically based ecosystems and products.

Soil production may be driven through accelerated regeneration—regolith, regenerative processing, and biological system. Plants can be grown on the moon, as evidenced by plants recently grown in Apollo lunar samples. Plants exposed in regolith were found to be safe and unaffected. Plants grown on the Moon—Chang'e 4. Plant seeds have gone and returned to Earth and their progeny still live. Proof of concepts have shown lunar simulant can be a good test bed for lunar agricultural.

The following are considerations for off-Earth habitation.

- Food: Basic foodstuff, either fruits or vegetables, or larger broad crops such as potatoes, rye, or beans.
- Herbs: Amendments for lunar cuisine and possible other applications. Ability to freshen or spice up food to improve morale and digestion
- Bioproducts: Many products have biological origination, such as rubber. Ability to produce these using ISRU opens many new doors and value add applications.
- Animal Husbandry: Ability to support chickens, rabbits or other animals like a Jersey Cow all present a number of additional possibilities.
- Medicinal: Most medicines have biological roots, such as Willow Bark containing salicin which has for millennia been used and is still used in place of aspirin or Acetaminophen and could likely be safely used for joint pain, cramping or headaches. Things like mint or chamomile can be used to create teas for stomach remedies.
- Textiles: Textiles such as hemp, flax or others (cotton is possible but water intensive) all present interesting possibilities and new economic opportunities.
- Advanced Products: Not simply producing rubber, put perhaps developing new kinds of rubber, or not just cloth textile but instead fully functioning clothes made in space.
- Return to Earth: Any of the above products have the possibility to be exported to Return to Earth for a higher cost for both novelty but also the ability to possibly have superior products due to low gravity advantage
- Entertainment and Education: Data is the easiest thing to Return to Earth—farming and homesteading channels have large audiences on places like YouTube or Twitch streaming—there exists a good possibility to transfer these back to earth in the form of content streams—opening possibility for augmentation of funding streams and increasing popularity and marketing.
- Non-traditional: Greenspace, oxygen, water recycling, psychological support, and natural areas all are potentially invaluable. It is well understood that astronauts often end up craving or are fascinated by growing plants. As humans are co-evolved with nature, it is important to remember that humans must have nature around for balance.

Regarding plants in microgravity, there is a relatively long history of plants and space. For example, Apollo 14 carried 400 tree seeds and when returned to Earth were planted to observe if any issues arose, with no issues detected. There have also been plants grown in orbit, including *Arabidopsis* (Thale cress), Bok choy (Tokyo Bekana) (Chinese cabbage), Super dwarf wheat, Apogey wheat, *Brassica rapa*, Rice, Tulips, Kalanchoe, Flax, Onions, peas, radishes, lettuce, wheat, garlic, cucumbers, parsley, potato, and dill, Lettuce and Cinnamon basil, Cabbage, *Zinnia hybrida* ("Profusion" var.), Mizuna lettuce, Red romaine lettuce ("Outredgeous" var.), Sunflower, *Ceratopteris richardii*. On the Moon, the Chinese Rover sprouted Cotton on the Moon. But as recognized herein, growing orbital plants is costly inside specialized modules. The lack of "down" complicates the physics—water sticks to plant root causing it to drown. Nutrient Management is extremely complicated. Individual seed pods may be required to mitigate microgravity issues. And no significant work with pseudo-gravity exists.

Apollo Mission samples were used to grow plants. The fear that the Moon was toxic was disproven—plants can grow in lunar regolith. The Moon has everything (though in limited availability) to grow plants. Regolith not without challenges—limited organic matter, nutrients are not immediately bioavailable. Experiments show that microorganisms can increase bioavailability. Promising avenues to improve lunar regolith into soil will continue to studied and revealed. There is significant water on the Moon. And studies have shown plants can grow in Lunar simulants.

Astronauts on the International Space Station (ISS) eat about 4 pounds of food a day, such that at least 1,460 pounds of food in a year should be produced per ISS astronaut. Stated differently, 1,460 pounds of food would support one person or more likely support 25% of the diet for a crew of four. Although there is not yet a clear understanding of what ⅙th gravity will do on the human body, there is a good understanding of 1 g and microgravity, such that lunar requirements are likely to evolve quickly. It is also not well understood what the impact of $\frac{1}{6}^{th}$ gravity will be on plants. And nutrient requirements may change rapidly depending on results of long term lunar stays.

FIG. 21 illustrates various features that may be included in a Lunar Exploration Agricultural Facility Habitat.

Exemplary embodiments may be configured with an emphasis on local/localized/edge computing and communications architectures, including extensive use of personal/personalized sensors on, in, attached to, or otherwise as close physically and/or mentally to the person as possible, in as near real-time as possible. Exemplary embodiments may include the use of metaverse for mental state simulation/determination/projection and dynamic, context-based redirection/reallocation/rerouting of computational resources based on context.

As described above, context-based systems and methods will benefit, particularly Off-Earth, in having computation of contextual elements (and of course collection of "raw" contextual data) as close to the person/place/thing as possible, to avoid time/space/other contextual distortions or synchronization issues and/or need for corrections, as well as to facilitate as real-time analysis, diagnostic/triage, and treatment as possible, as well as avoid the inevitable technical issues associated with multi-entity communications (e.g., availability of channels, bandwidth, interference/noise, capacity, competition for resources, radiation-based issues, etc.). Even if the patient his/herself does not have the needed data collection sensors/mechanisms, others nearby could be used, or other data collection mechanisms on places and "things" (e.g., equipment, furniture, etc.) that can capture general or even individualized data elements. It is anticipated that at least some of this personal and/or contextual data (perhaps that related to key ailments/triggers) would be frequently, even continually be updated/adjusted to have "at the ready" key information in case a medical (or otherwise personal) issue arises, to maximize the potential of it being immediately addressed without external/non-local resources. They may even be a contextual-dedicated computer/computer complex as well as associated sensors/sensor arrays focused on just this capability for every contextually different entity/part of an entity, including for example different compartments of a spaceship, different rooms in lunar base, above/at ground versus underground environments, purpose-focused areas (food growing versus human sleeping, for example), etc. Commonly used equipment would be another good "thing" to have sensors/context data collection mechanisms tethered (in various ways, including wirelessly) in particular to collect data on usage of that equipment and more broadly the context in which the equipment is placed/being used and by who and how and for what purpose (why).

To facilitate this (near) continual, or otherwise frequently and/or when-needed/event-triggered data collection and processing, every area in space where humans are (or will be) might benefit from a localized contextual architecture/computing capability. This capability would supplement the contextual data collection/processing that would be done on/in/by the human carried/following, e.g., a scenario is envisioned where a human is accompanied by a robot wherever he/she went, with one of their capabilities to collect/process contextual data associated with the human/humans in that area. Other uses in this innovation serving as a confidant, therapist, or even "on-call" personal doctor, one even capable of doing real-time, context-specific emergency surgery. Each area/compartment/differing contextual environment could have the capabilities of not only collecting/monitoring/controlling the area environment, but also could be tasked with the immediate detection of humans entering the area, collecting their personalized data, and modifying/updating/coordinating it with or otherwise adjusting that data to reflect the contextual information for that area.

There will be context-based instances where the intended or in-progress system, architecture, application, and/or resources that will be employed in a particular use case will need to be changed/modified as the context changes or is anticipated to change. As an example, a particular piece of functionality may be processing locally on a given Moon context, perhaps on the person doing something on/near the surface (and thus particularly susceptible to radiation/radiation spikes). A solar flare is detected thereby indicating an upcoming spike in radiation, which takes about 8 minutes to reach the Earth/Moon. To the extent the flare can be detected or anticipated before it reaches the Earth (or, in the case of solar particles being emitted by the flare, which can take days to reach the Earth/Moon), the flare could trigger a change in computation resources utilized. For example, instead of whatever functionality continuing to execute locally on the person's base computer, it can switch to other localized, more hardened resources for execution (a kind of mini-disaster recovery prevention scheme, but preemptive) that are located perhaps subterrain, in a special hardened emergency processor on the person (only used in emergencies for various reasons), or even Off-Moon until the solar flare passes (e.g., the context reverts to normal).

Need for Multi-Context Dimensional Reference System(s)

As described above, there is a significant need for a multi-entity, context-diverse reference system or systems to enable synchronization, coordination, (re)calibration, and/or apples-to-apples comparison of data that is conceived on, referenced on/by, measured on/by, operated on/by, utilized on/by, or otherwise has data involving more than one entity and/or location in physical space, as well as virtual representations of or related to physical space in metaverse or other non-physical systems.

Location data as well will need to expanded in scope, content, and associated variables, not only to reflect the absolute location of a given person/place/thing "localized" to its entity (e.g., the Moon, spaceship, etc.) but its relative location as compared to both other things on the entity and also relative to other entities. This is complicated by the fact that every entity, at any given time, will likely be moving through space, and in particular moving relative to each other, making common reference points problematic, particularly those lending themselves to static/not changing bases. There are various reference corrections possible; for example, it could use the location of the Sun (its center in particular), or the center of Galaxy, or the Sun in reference/relation to the center of the galaxy, as the "ground truth", and subsequently measure location of an entity relative to that location. Or the Earth (center, or some other point on/above it) could be a base reference point (with a particular x/y/z coordinate on Earth as "ground zero" reference point); this would simplify matters as it relates to Off-Earth to On-Earth comparisons. Additional adjustments would likely be needed to compensate for the continual moving of all entities; some sort of vector location system could be used to take both location and direction/speed/velocity into account in any reference/reference adjustment system(s).

While there are the beginnings of Off-Earth reference systems emerging, such as trying to determine location on the Moon by referencing GPS satellites, whether this will work, for what use cases, and for what entities (e.g., other than the Moon) is unknown. In all likelihood, like on Earth, there will be multiple location determination techniques (e.g., GPS, TDOA, Signal Strength, Beacon, etc.). But these techniques/technologies typically utilize for absolute (versus relative) location a standard coordinate system, most notably the WGS 84 system, which uses the center of the Earth as the origin/base coordinate (with the equator as latitude zero, and the Prime Meridian as longitude zero). Any system utilizing Earth GPS (like the above Moon system) would also in essence utilize the center of the Earth as that base origin coordinate. Such a system may not be and likely is adequate/sufficient for many off-Earth location reference systems and associated use cases. The WGS 84 system only includes a few physical coordinates (x, y), and no contextual ones. More broadly, while the Moon is tightly tied to the Earth in multiple ways, other entities (e.g., Mars) are less so. It is very likely that at least some Off-Earth coordinate systems will need a non-Earth-based coordinate system based on something other than the middle of the Earth mass as the base origin point.

To this last point, a key consideration is that in practical terms, there is no non-moving "location" in space as everything is moving relative to something else. So knowing velocity and where it is going is important or essential. While location on an entity (e.g., the Moon, a spaceship) is "fixed" relative to its physically associated surroundings (anywhere on, above, or underneath the lunar surface of the Moon), in comparison to off-entity objects the entities involved will always be moving in relationship to each other. Further, each entity has its own "idiosyncrasies" that make different location systems problematic. For example, while it is possible to place a satellite in a "stable" Earth orbit (e.g., predictable), this is not true on other entities. For example, achieving stable orbit around the Moon is very difficult If not impossible (from a precision prediction standpoint) due to various Sun-related factors. This and other reference systems would thus be facilitated by being more vector based.

With a stable reference point, such as shown in FIG. 22 by the satellite orbiting (small circle) around the Earth, the location (or at least enabling a type of location) for other entities/satellites are possible. FIG. 22 illustrates LaGrange points that are stable points of equilibrium for small-mass objects under the influence of two massive orbiting bodies. Mathematically, this involves the solution of the restricted three-body problem in which two bodies (e.g., the Sun and the Earth) are very much more massive than the third body, which in this example is a satellite shown as a small circle orbiting around the Earth.

The change in velocity is the most important factor in how this actually works and can represent acceleration. Lagrangian point GPS-like systems use orbit/orbital velocity as part of their system; as long as there is line-of-sight then at least some sense of location is possible. Alternatively, or in addition, such "partial" reference systems can be used with other points of reference to develop a complete system, including triangulating their position relative to each other and then relatively to Earth.

The Moon itself has very few stable orbits, requiring them to be constantly "repaired." This is due to the fact that the Moon's much lower mass/gravity means that anything in its orbit will be gravitationally acted upon by Earth, causing it to destabilize. The Lagrange points in the Earth orbital platform provide a Geostationary-esque orbit, in that any objects in this orbit will stay in the general area. This provides a unique opportunity for location of certain asset types.

By taking advantage of this "solar stationary" type orbit, constellations of location tracking satellites can be deployed to this space. These satellites could then use a point of reference (such as the Sun) to determine their own location. If at each L point, three or four or more satellites were there, all the objects could triangulate their own position relative to each other, relative to the Sun, and relatively to the Earth. This could provide the basis for an Earth orbital location tracking and navigation system—or GPS for space. Putting these mini constellations at each of the 5 L points, at any given time an object in Cislunar space should have the ability to have at least 1 LaGrange point and possibly 2 or more LaGrange points. With the multiple tracking satellites at each point, this would provide a sufficient number of datapoints to give a rough but accurate idea of location and trajectory. Further applications of this could be for traffic management beyond being the foundation for other data collection such as medical systems.

A "subset" of reference system-related issues (and solutions) is with respect to gravity management. For example, gravity and environmental conditions may be recorded into EHR/EMR health care data systems. This contextual information is typically never captured in a (on-Earth) doctor's office but as described above will be essential in space medicine. This information can be validated and observed and will be essential input into other technology or decisions. Such factors, some described earlier, that will be part of such systems include enabling machine/AI system to adapt to gravity conditions—microgravity —⅙ Earth's gravity on the Moon, ⅓ Earth's gravity on Mars, etc., as well as factors like atmospheric conditions, hydration levels, vital signs expressions, etc. For example, heat rate or O2 may be different depending on a slew of factors—what is normal—but more importantly what understanding, utilizing machine learning/AI and other context-based mechanisms described above what is normal, under these environmental conditions, for comparison/synchronization purposes.

As discussed in various places, triggers like Anger, Boredom, Money, Stress, and so on are those "things" which can, in turn, cause or serve as the primary catalyst for or otherwise "activate" certain (usually negative) behavior, such as an alcoholic being triggered to drink/relapse. While triggers can often be enough by themselves to "cause" or otherwise result in the (undesired) behavior, that is not always the case, particularly as many triggers are emotional in nature at least in part, and emotions tend to "blend into" or merge with other emotions (and thus triggers), and/or causing/triggering other emotions/triggers to occur, and/or vice versa. For example, Anxiety can cause/lead to/trigger Depression or vice versa. Boredom can cause/lead to/trigger Loneliness, which can, in turn, lead et al. to Depression. Kids (children) chaos can cause Noise which can result in Yelling, which can result in Anger. These are all "related triggers" to the original trigger that started the process. FIG. 19 illustrates how triggers can be "related." The practical effect of a trigger activating related triggers is a kind of emotional/trigger "snowball" that rolls over the sufferer. Some of the snowballs "picked up" after the ball starts rolling may be relatively small, or as big if not bigger than the original snowball-starting trigger, just like in the physical snowball world. This makes preempting the original "upstream" snowball (e.g., the one highest on the mountain) to begin with so critical.

In an alcoholic example, it is not uncommon for alcoholics to have somewhere between 5 and 10 (or even more) very significant or major triggers, e.g., a trigger(s) that, in and of itself or by its very nature, can individually lead to a relapse. These significant/major triggers really make the person want to (or "have to") drink, more often than not. They can make the person want to drink all by themselves, e.g., independently of anything else going on in the person's life. But they also can set off a number of "related" triggers. Using a straw-that-broke-the-camels-back metaphor, a significant/major trigger (and possibly more) can serve as the first 900 straws on the camel-relapse back that can stand 1000 until it breaks (relapses). One or more related triggers—for that person—might serve as the 101 straws that puts the camel over the top: breaks its back. And these triggers, and how much they "weigh", can depend on the context, with different triggers having different straw "weights" in different contexts. Indeed, for a given person, one trigger might be significant/major and another related trigger relatively minor in impact; in other contexts the reverse might be true, or other triggers coming into the mix in varying degrees. In effect, for different people, and even for the same person, any/all of the triggers (and others) shown in FIG. 19 might be both significant/major triggers as well as related triggers for other significant/major triggers depending on the context and the person.

This sea of interrelated triggers is a different concept than is "taught" in rehabilitation programs of all sorts. Even when traditional treatment programs go through some degree of trigger discussion, they nearly always "treat" triggers as "standalone", e.g., the focus is on the effects that a trigger has on your drinking habits (in an alcoholic example) due to that trigger all by itself. At best (worst) such treatments might incorporate the concept of "dual-diagnosis" of Alcoholism and Depression for example, or Anxiety and Depression in a more general mental health treatment program.

Unfortunately, the pressures of daily life rarely line up in such single file fashion. Certain situations in a person's daily, historical, or ongoing life can "activate" or trigger other triggers. Again, these are referred to herein as related triggers. For example, Boredom can make you Lonely, which, in turn, might make you want to go out with friends who drink (causing direct or indirect Peer Pressure), which may take you to a place where Proximity and Smell of nearby alcohol has you drooling for a Taste of alcohol to help you Escape from other problems in your life. It is incredibly difficult to defend against alcohol in all of these simultaneous/near-simultaneous circumstances. There are hundreds, even thousands of possible combinations. And many of them, in relevance, degree, impact, and combination can vary in their "snowball building" by context, making treatment far more complex. And life is complex—what further makes determining/diagnosing/treatment so difficult is that many triggers often "attack" at the same time or nearly, and/or occur so often in conjunction with related triggers that it sometimes becomes impossible to sort out the different triggers involved, and what is a "cause" and what is an "effect".

To add even more complexity, a person's defenses, such as an alcoholic's defenses, may be weaker for some triggers than others. Worse still the strength of the person's defense may vary depending on the hour of the day, day of the week, personal living environment at any given time, how their day at the job went, and so on. In total, this complexity of trigger/related trigger relationships and variability of how and when they attack makes it almost impossible to build a single defense that works against all of a person's vulnerabilities all of the time—a much more sophisticated set of systems, methods/processes, and mechanisms are needed—examples of which are disclosed herein.

Exemplary embodiments also include and/or are directed to a "contextualization engine" In short, a contextualization engine is a system(s) and associated processes, data sets, and enablers like machine learning/AI that can:

a) determine the context of an entity from the data available (via sensors, etc.);
b) compare various contexts to determine differences and commonalities among data/data sets; and
c) formulate actions and adjustments needed to appropriately cross-reference, calibrate, adjust, modify, and/or synchronize ("adjust[ment]") one or more contexts with other context(s), primarily for the purpose of adjusting other data elements, such as medical tests or treatment procedures, to compensate for or otherwise take into account the differences between the data taken/used in a context to make it usable for the other context(s).

A simple example is a medical test typically taken on Earth (in Earth normal gravity) but is taken on the Moon (which is approximately 0.17 gravity of the Earth), where the test in some way is dependent on the gravity, mass, and/or weight in administering the test and/or interpreting the results, and/or influence treatment based on those results. However, in specialized environments/communities, particularly off-Earth, the contextual factors involved are likely much more complex, including literally dozens of factors that go into determining the who, what, when, where, how, and why of the context. The contextualization engine would automatically (to the extent possible) identify the available factors, assess their appropriately relevant applicability/priority/importance/weight ("weight"), as well as the factors' interrelationships to other contextual factors (a simple example being relationship between (physical) weight to gravity and even speed/acceleration of a spacecraft) as well as relevance to the behavior/activity being performed, e.g., the specifics of the test. Just in this one example, e.g., medical test A, the contextual factors involved, as well as their (importance) weights, as well as the data sets drawn on for comparison purposes, may be very different than for medical test B, let alone the treatment based on medical test A. As such, a focused systemic capability that specializes in contextual determination is needed.

Further, the contextualization engine as disclosed herein may go well beyond "just" the comparison of multiple contexts and formulations of needed adjustments. For example, the contextualization engine may be used to adjust/modify the context before it is used/needed. In the medical test example, there may be factors that can be modified before the fact (of conducting the test) that by doing so can reduce the complexity of the adjustments, for example, making sure that the equipment used, temperature and humidity of the room, radiation levels, preparations by the entity being tested (e.g., food/liquid intake), even when and type of room (shielded, not exposed to the Sun, etc.) is the same or as similar as possible, thereby minimizing the number of uncontrollable factors (such as gravity) that have to be adjusted after the fact.

This kind of contextual "pre-emption" would be a core part of the functionality of the contextualization engine, and preferably would benefit from systemic ties to/integration with the various systems that control these factors, such as room temperature control, etc. Besides ensuring accuracy and integrity of the contextual settings (e.g., not dependent on human modification of the temperature), the contextualization engine may be configured to automatically adjust/compensate for interrelationships between factors. A simple example being ensuring the patient/entity is "comfortable" during a test say for Anxiety. Besides "being comfortable" often being a qualitative/subjective term, there are different ways of achieving comfort, such as by modifying the room temperature, humidity, and lighting levels relative to monitoring the entity/person's body temperature and other indicators of Anxiety. With more than one or two factors involved in a context, the ability for a human or even "dumb" system to automatically identify, detect, compute, and implement various "comfortable" contextual factors quickly becomes overcome. Thus, a contextualization engine, including one aided by machine learning/AI, will enable such complex context "pre-emption" activities.

A part of the contextualization engine will be in determining "absolute" context vs "relative" context, or a hybrid thereof. Absolute context is in determining/defining a context relative to an established set of parameters. Thus, temperature is set to Fahrenheit (or Celsius) scale (or in space even Kelvin), and thus any assessment/determination and associated adjustments would be made relative to that temperature's "coordinate" system, e.g., how it is measured.

But other contextual factors, or even factors like temperature, may care less about "absolute context" than "relative context", e.g., how the context "at hand" versus being compared to via historical and/or predictive information is relative. Thus, it may be far more important (in a test for example) for the context data sets involved be within 2 degrees (Fahrenheit) of each other versus being done at 70 degrees Fahrenheit. Or (in a hybrid) determine that the test must be done within a 60 to 80 degree Fahrenheit range, not exceeding a 2 degree variation from beginning to end of the test. The contextualization engine can identify the need for such absolute/relative/hybrid requirements and automatically adjust.

In addition, for many specialized communities/environments, particularly off-Earth, the contextual data sets captured within the "macro-context" of the community (e.g., on the Moon, 2000 feet underwater) is likely to be very limited. Thus, the contextualization engine will need to project, predict, extrapolate, interpolate, or otherwise utilize the available contextual data far beyond what the actual data sets contain Here again machine learning/AI can be a key enabler, e.g., by taking data from other contexts (say 2000 feet underwater) and adjusting them for use in microgravity conditions, for example. This will likely be an iterative process, e.g., the first attempts potentially inaccurate, so a learning capability will also be a key part of the contextualization engine, particularly in highly complex environments where there are dozens or hundreds of contextual factors, and there is a high likelihood that there is little (or no) existing data involving all of those factors in general, let allow relative to the activity and macro-context at hand (e.g., a particular data test being done in an underground moon base).

Thus, the data sets involved in a contextualization engine, while conceivably inclusive of any type of data, is focused on determining the where, what, when, who, how, and why of an entity(ies) particular environment/situation/problem/motivation/activity (e.g., context), future context, and/or past context. The data sets that can contribute to the above may come from many diverse areas/sources, which data may or may not already be ready/sorted/analyzed for context-relevance. Further, it will require the ability to identify resources (e.g., other computer systems, personnel, equipment, etc.) and formulate and implement actions to be able to "pre-emptively" adjust a context before (and during) it is being used, through communications and computer system linkages with these other associated systems, processes, etc. This could include the use of digital agents (e.g., as disclosed in U.S. Provisional Patent No. 63/441,569) that perform key subsets of contextualization engine-related functionality. Another part of the contextualization engine functionality will be in identifying "useful" data for contextualization purposes, and further "training" digital agents and the contextualization engine itself in what data to use, how, and for what purposes. Indeed, as early indicators of AI functionality have shown, not all data is "equal" in if, and how, it is used in an AI-type digital agent; the ability to identify relevant data by itself will be a highly complex task needing focus and specialization—focus and specialization provided by this invention's contextualization engine.

To provide "context" for the innovation represented by a contextualization engine, it may be helpful to look at the complexity for just one of those factors, positioning/location determination engines.

A positioning engine utilizes whatever data it can to ultimately determine a location. This can use "absolute" positioning, such as GPS (which itself is time based), "relative" positioning (e.g., I'm 30 feet way from this beacon, determined by signal strength values), and/or a hybrid. Absolute positioning uses a reference system (such as WCS), with the core reference points are the equator (for latitude) and the prime meridian (longitude), with all coordinates are relative to those lines dividing the earth.

Just determining absolute or relative location off-Earth will be highly complex, and are limited in using Earth-based technology, such as the U.S. GPS system, which is built for on-Earth coordinate determination. Evolving methods include various technologies/methods including Inertial Measurement Units (BTUs) (devices that incorporate accelerometers and gyroscopes to measure a spacecraft's linear and angular accelerations and rotations); Star Trackers(cameras that capture images of the stars and compare them to an onboard star catalog); Laser Ranging (retroreflectors in the ISS that reflect laser beams sent from ground-based tracking stations); Ground-based Tracking (A network of ground-based tracking stations around the world monitors the ISS's position, velocity, and attitude using radar, radio frequency tracking, and other techniques); Orbital Data from Launch Vehicles (A spacecraft's position and velocity are derived from the launch vehicle's telemetry, allowing ground controllers to establish a starting point for further navigation); and Onboard Sensors, including sun sensors, Earth horizon sensors, and altimeters. Thus, just doing a calculation for the "where" of an off-Earth activity will be highly complex. In turn, comparing and adjusting that "where" in relation to an entity's behavior/performance on Earth will be even more complex, and in turn combining that "where" (absolute and/or relative and/or hybrid) with other what, when, how, who, and why factors will further (and potentially hugely) increase the complexity.

Indeed, it is anticipated that one or more context "coordinate systems" will be used by the contextualization engine, and indeed perhaps invented and refined by the AI-aspect of the contextualization engine as more data is contextualized. While aspects of the present disclosure are not limited to any specific context coordinate system, one or more such coordinate system and methods may be included in exemplary embodiments. Thus, instead of describing a context as a collection of individual measurements, that then individually have to be compared to other measurements, adjustment calculations made, then applied to each individual measurement, it would be preferable to have a contextualization engine that does all of this, perhaps even having a single score or set of scores, using one or more context coordinate systems, to capture the context on a variety of sensor dimensions, with a given context being determined by a plurality of sensor measurements, utilizing sensors from a broad and deep portfolio of possibilities, such as shown in FIG. 23 and disclosed herein.

The sensors can include location sensors (e.g., for detecting, measuring, determining, and/or calculating presence/proximity/position/absolute location/relative location/hybrid) including radio frequency-based location systems, cellular-based network technologies and methods, satellite systems (e.g. GPS, GLONASS, Starlink, etc.), movement and directional sensors (motion/acceleration/velocity/tilt/orientation/yaw/pitch/roll) including inertial sensors, motion sensors/detectors, accelerometer and velocity sensors, gyroscope sensors, and analog and digital compasses. The sensors can include industrial sensors (e.g., for determining/measuring/calculating/controlling processes/control capabilities/functions and functionality), mechanical sensors (e.g., for force/load/torque/strain/pressure); "Earth" sensors (e.g. weather/seismic/agriculture (group: environmental); climate sensors (e.g. temperature/humidity/moisture (Groups: Environmental, Energy); electrical/electronic sensors (e.g., electric/magnetic/computers/quantum/metaverse/augmented and virtual reality); liquids, water/vapor/ice sensors (e.g., flow/leaks/levels/quality/state; chemical sensors chemical/gas/toxicity/radiation; biometric sensors (e.g., human body/activities/health care); audio/sound/audible sensors (e.g. acoustic/sound/vibration/ultrasound); (in)visible/light sensors (e.g. optical/image/video/ambient/machine/infrared/other).

In exemplary embodiments, the system is configured (e.g., includes a context determination engine or contextualization engine, etc.) to be operable for determining context(s) associated with behavior(s) of at least one entity (e.g., human, animal, another system, etc.) within an environment (e.g., on-Earth environment, off-Earth environment, specialty environment, etc.). In addition to the determination of context(s), the system may be configured to be operable for capturing/storing all the metadata associated with each measurement that would allow for an apples to apples synchronization/adjustments/modifications across different macro contexts. Such different macro contexts may include the Moon versus space station versus spaceship at X location versus closed/specialized environments versus normal/historical measurement on Earth. For example, performing an anxiety or leg ailment diagnostic can have the measurements taken in these specialized contexts and then be appropriately adjusted or calibrated relative to whatever medical baseline/stored records exist. In such exemplary embodiments, the system may be configured with specialized machine learning/AI-based capability(ies) for making the calibration to the baseline/stored records.

Exemplary embodiments are disclosed of a system configured to calibrate, cross-reference, adjust, modify, and/or synchronize measurements of a plurality of different devices, sensors, other systems, and/or communications network(s) automatically to determine, assess, accommodate for, and/or compare different context(s) and/or instances of the same or similar context(s) of an environment(s) under which the plurality of different devices, sensors, other systems, and/or communications network(s) will be, are being, and/or have been used. The calibrating, cross-referencing, adjusting, modifying, and/or synchronizing provides the ability to compare data obtained for the context(s) and/or instances of the same or similar context(s) in an environment(s) associated with the at least one entity undergoing, involved in, and/or associated with a particular purpose, behavior, and/or activity via the plurality of different devices, sensors, other systems, and/or communications network(s) with data obtained elsewhere under different context(s) and/or instances of the same or similar context(s) in other environment(s) for the same or similar purpose, behavior, and/or activity.

In exemplary embodiments, the system is configured with specialized machine learning and/or AI-based capability(ies) to calibrate, cross-reference, adjust, modify, and/or synchronize the measurements of the plurality of different devices, sensors, other systems, and/or communications network(s) automatically to accommodate for the different context(s) and/or instances of the one or more context(s) of the environment(s) under which the plurality of different devices, sensors, other systems, and/or communications network(s) will be, are being, and/or have been used.

In exemplary embodiments, the environment is an off-Earth environment. And the system is configured to calibrate, cross-reference, adjust, modify, and/or synchronize the measurements of the plurality of different devices, sensors, other systems, and/or communications network(s) automatically to accommodate for the different context(s) and/or instances of the one or more context(s) of the off-Earth environment under which the plurality of different devices, sensors, other systems, and/or communications network(s) will be, are being, and/or have been used. The calibrating, cross-referencing, adjusting, modifying, and/or synchronizing provides the ability to compare the data obtained for the context(s) and/or instances of the one or more context(s) within the off-Earth environment associated with the at least one entity undergoing, involved in, and/or associated with the particular purpose, behavior, and/or activity via the plurality of different devices, sensors, other systems, and/or communications network(s) with data obtained on-Earth for the same or similar purpose, behavior, and/or activity.

In exemplary embodiments, the environment is an off-Earth environment, or the environment is an on-Earth enclosed facility and/or an on-Earth specialty environment having abnormal condition(s). And the at least one entity comprises one or more of a human, an animal, a plant, another system, a machine, a robot, an artificial intelligence, a virtual agent, a corporation, a business entity, a nation, a network, a driverless vehicle, a connected vehicle, a drone, and/or a governmental entity.

In exemplary embodiments, the system is configured to be operable for prescribing and/or applying artificial electromagnetic fields for health, safety, and/or treatment for the at least one entity within the environment. For example, the environment may be an off-Earth environment. And the system may be configured to be operable for prescribing and/or applying artificial electromagnetic fields for health, safety, and/or treatment for the at least one entity within the off-Earth environment to preempt and/or lower the risk of a future occurrence of a psychological episode, which may be linked to reduced protection of the Earth's electromagnetic field coupled with a solar event(s).

In exemplary embodiments, the system comprises the plurality of different devices, sensors, other systems, and/or communications network(s), and wherein the system is configured to: determine, through a plurality of measurements/readings taken by the plurality of different devices, sensors, other systems, and/or communication network(s) and/or through information from and/or about system inputs, behavior(s) and/or activity(ies) of at least one entity within an environment and: (a) context(s) associated with the behavior(s) and/or activity(ies) of the at least one entity; or (b) location and the context(s) associated with the behavior(s) and/or activity(ies) of the at least one entity; assess, evaluate, and predict a risk of a future occurrence(s) of context(s) associated with behavior(s) and/or activity(ies) of the at least one entity. The system is further configured to: facilitate one or more actions and/or activities to preempt and/or lower the risk of a future occurrence(s) of context(s) associated with behavior(s) and/or activity(ies) of the at least one entity before the context(s) associated with the behavior(s) and/or activity(ies) occurs, when the context(s), behavior(s) and/or activity(ies) of the at least one entity is determined to be detrimental to the at least one entity and/or to the environment. Additionally, or alternatively, the system is further configured to facilitate one or more actions and/or activities to preempt and/or lower the risk of a future occurrence(s) of behavior(s) and/or activity(ies) associated with the context(s) of (e.g., context(s) involving and/or associated with, etc.) the at least one entity before the behavior(s) and/or activity(ies) of the at least one entity occurs, when the context(s), behavior(s) and/or activity(ies) of the at least one entity is determined to be detrimental to the at least one entity and/or to the environment.

In exemplary embodiments, the system comprises the plurality of different devices, sensors, other systems, and/or communications network(s), wherein the system is configured to determine, through a plurality of measurements/readings taken by the plurality of different devices, sensors, other systems, and/or communication network(s) and/or through information from and/or about system inputs, behavior(s) of at least one entity within an environment and context(s) associated with the behavior(s) and/or activity(ies) of the at least one entity. The system is further configured to dynamically and adaptively determine a reward for incentivizing context(s) associated with behavior(s) and/or activity(ies) of the at least one entity and/or for incentivizing behavior(s) and/or activity(ies) associated with the context(s) of (e.g., context(s) involving and/or associated with, etc.) the at least one entity, when the context(s), behavior(s) and/or activity(ies) of the at least one entity is determined to be beneficial to the at least one entity and/or to the environment. Additionally, or alternatively, the system is further configured to dynamically and adaptively determine a disincentive for disincentivizing context(s) associated with behavior(s) and/or activity(ies) of the at least one entity and/or for disincentivizing the behavior(s) and/or activity(ies) of the at least one entity associated with the context(s), when the context(s), behavior(s) and/or activity(ies) of the at least one entity is determined to be detrimental to the at least one entity and/or to the environment. In such exemplary embodiments, the system is configured to facilitate redemption of the reward to thereby incentivize the creation, improvement, or increase in frequency or occurrence of context(s) associated with behavior(s) and/or activity(ies) and/or the creation, improvement, or increase in frequency or occurrence of behavior(s) and/or activity(ies) associated with context(s) of the at least one entity that is beneficial to the at least one entity and/or to the environment by one or more of a material reward, a physical reward, a financial reward, a monetary reward, an electronic reward, a virtual reward, a non-material reward, and non-financial reward; and/or facilitate redemption of the disincentive to thereby disincentivize the existence, occurrence, or frequency of context(s) associated with behavior(s) and/or activity(ies) and/or the existence, occurrence, or frequency of behavior(s) and/or activity(ies) associated with context(s) of the at least one entity that is detrimental to the at least one entity and/or to the environment by one or more of a material punishment or penalty, a physical punishment or penalty, a financial punishment or penalty, a monetary punishment or penalty, an electronic punishment or penalty, a virtual punishment or penalty, a non-material punishment or penalty, and a non-financial punishment or penalty.

In exemplary embodiments, the system is configured to be operable in an environment in which atypical Earth factors must be included and considered due to potential medical implications, such as Earth's gravity, atmospheric conditions, exposure to non-traditional radiation source(s), and health hazards like galactic background radiation or solar winds, whereby said atypical Earth factors influence the needs for monitoring, diagnosis, prescriptive action, and/or to further support diagnosis and treatment by a human doctor or artificial intelligence (AI) health care system.

In exemplary embodiments, the system is configured to be operable for calibrating, cross-referencing, adjusting, modifying, comparing, synchronizing, and/or level setting of the measurements obtained using data collection, storage, processing, analysis, and/or application of capabilities and results of the plurality of different devices, sensors, other systems, and/or communications network(s) automatically to determine, assess, accommodate, and/or compare for different context(s) and/or instances of the same or similar context(s) of one or more environments under which the plurality of different devices, sensors, other systems, and/or communications network(s) will be, are being, and/or have been used. The calibrating, cross-referencing, adjusting, modifying, comparing, synchronizing, and/or level setting provides the ability to compare data obtained for the context(s) and/or instances of the same or similar context(s) in an environment(s) associated with the at least one entity undergoing, involved in, and/or associated with a particular purpose, behavior, and/or activity via the plurality of different devices, sensors, other systems, and/or communications network(s) with data obtained elsewhere under different context(s) and/or instances of the same or similar context(s) in other environment(s) for the same or similar purpose, behavior, and/or activity.

In exemplary embodiments, the system comprises a contextualization engine configured to: determine and/or predict one or more contexts of the at least one entity from available and/or generated data including data from available sensors; compare various contexts and/or similar contexts and/or instances of context(s) and/or similar contexts to determine differences and commonalities among the one or more contexts' underlying and/or associated data/data sets; and formulate actions, modifications, and/or adjustments needed to appropriately cross-reference, calibrate, adjust, modify, and/or synchronize the one or more contexts with other context(s) and/or instances of one or more contexts, for the purpose of adjusting the one or more contexts' underlying and/or associated data/data elements, including for medical tests, treatment procedures, and/or other medical activities, to compensate for, adjust, or otherwise take into account the differences between the data underlying and/or associated with the one or more contexts with the data underlying and/or associated with the other context(s) and/or similar contexts and/or instances of the one or more contexts and/or similar contexts, wherein the purposes, behaviors, and/or activities of the contexts are the same or similar.

In exemplary embodiments, the system is configured to be operable automatically without manual human intervention.

In exemplary embodiments, the system is configured to solicit and/or collect user feedback and to thereafter interpret the user feedback for use in determining the context(s) associated with the behavior(s) and/or activity(ies) of the at least one entity.

In exemplary embodiments, the system is configured to obtain and interpret human feedback for use in determining the context(s) associated with the behavior(s) and/or activity(ies) of the at least one entity.

In exemplary embodiments, a system comprises a plurality of different devices, sensors, other systems, and/or communications network(s). And the system configured to: determine, through a plurality of measurements/readings taken by the plurality of different devices, sensors, other systems, and/or communication network(s) and/or through information from and/or about system inputs, behavior(s) and/or activity(ies) of at least one entity within or associated with an environment and: (a) context(s) associated with the behavior(s) and/or activity(ies) of the at least one entity; or (b) location and the context(s) associated with the behavior(s) and/or activity(ies) of the at least one entity. The system is further configured to: assess, evaluate, and predict a risk of a future occurrence(s) of context(s) associated with behavior(s) and/or activity(ies) of the at least one entity and/or a future occurrence(s) of behavior(s) and/or activity(ies) associated with a context(s) of the at least one entity; and facilitate one or more actions and/or activities to preempt and/or lower the risk of a future occurrence(s) of context(s) associated with behavior(s) and/or activity(ies) of the at least one entity before the context(s) associated with the behavior(s) and/or activity(ies) occurs when the context(s), behavior(s) and/or activity(ies) of the at least one entity is determined to be detrimental to the at least one entity and/or to the environment. Additionally, or alternatively, the system is further configured to: assess, evaluate, and predict a risk of a future occurrence(s) of behavior(s) and/or activity(ies) associated with a context(s) of the at least one entity; and facilitate one or more actions and/or activities to preempt and/or lower the risk of a future occurrence(s) of behavior(s) and/or activities associated with a context(s) of the at least one entity before the behavior(s) and/or activity(ies) occurs when the context(s), behavior(s) and/or activity(s) of the at least one entity is determined to be detrimental to the at least one entity and/or to the environment.

In exemplary embodiments, the environment is an off-Earth environment, or the environment is an on-Earth enclosed facility and/or an on-Earth specialty environment having abnormal condition(s). And the at least one entity comprises one or more of a human, an animal, a plant, another system, a machine, a robot, an artificial intelligence, a virtual agent, a corporation, a business entity, a nation, a network, a driverless vehicle, a connected vehicle, a drone, and/or a governmental entity.

In exemplary embodiments, the system comprises a contextualization engine configured to: determine and/or predict one or more contexts of the at least one entity from available and/or generated data including data from the plurality of different devices, sensors, other systems, and/or communication network(s) and/or through information from and/or about system inputs; compare various contexts and/or similar contexts and/or instances of context(s) and/or similar contexts to determine differences and commonalities among the one or more contexts' underlying and/or associated data/data sets; and formulate actions, modifications, and/or adjustments needed to appropriately cross-reference, calibrate, adjust, modify, and/or synchronize the one or more contexts with other context(s) and/or instances of one or more contexts, for the purpose of adjusting the one or more contexts' underlying and/or associated data/data elements, including for medical tests, treatment procedures, and/or other medical activities, to compensate for, adjust, or otherwise take into account the differences between the data underlying and/or associated with the one or more contexts with the data underlying and/or associated with the other context(s) and/or similar contexts and/or instances of the one or more contexts and/or similar contexts, wherein the purposes, behaviors, and/or activities of the contexts are the same or similar.

In exemplary embodiments, the environment is an off-Earth environment. And the system is configured to be operable for prescribing and/or applying artificial electromagnetic fields for health, safety, and/or treatment for the at least one entity within the off-Earth environment to preempt and/or lower the risk of a future occurrence of a psychological episode, which may be linked to reduced protection of the Earth's electromagnetic field coupled with a solar event(s).

In exemplary embodiments, the system is configured to: facilitate one or more actions and/or activities to increase the likelihood of a future occurrence of context(s) associated with behavior(s) and/or activity(ies) of the at least one entity when the context(s), behavior(s) and/or activity(ies) of the at least one entity is determined to be beneficial to the at least one entity and/or to the environment. Additionally, or alternatively, the system is configured to: facilitate one or more actions and/or activities to increase the likelihood of a future occurrence of behavior(s) and/or activity(ies) associated with the context(s) of the at least one entity before the behavior(s) and/or activity(ies) of the at least one entity occurs when the context(s), behavior(s) and/or activity(ies) of the at least one entity is determined to be beneficial to the at least one entity and/or to the environment.

In exemplary embodiments, the system is configured to solicit and/or collect user feedback and to thereafter interpret the user feedback for use in determining the context(s) associated with the behavior(s) and/or activity(ies) of the at least one entity.

In exemplary embodiments, the system is configured to obtain and interpret human feedback for use in determining the context(s) associated with the behavior(s) and/or activity(ies) of the at least one entity.

In exemplary embodiments, a system comprises a plurality of different devices, sensors, other systems, and/or communication network(s), the system configured to determine, through a plurality of measurements/readings taken by the plurality of different devices, sensors, other systems, and/or communication network(s) and/or through information from and/or about system inputs, behavior(s) and/or activity(ies) of at least one entity within an environment and context(s) associated with the behavior(s) and/or activity(ies) of the at least one entity. The system is further configured to dynamically and adaptively determine a reward for incentivizing context(s) associated with behavior(s) and/or activity(ies) of the at least one entity and/or for incentivizing behavior(s) and/or activity(ies) associated with the context(s) of the at least one entity, when the context(s), behavior(s) and/or activity(ies) of the at least one entity is determined to be beneficial to the at least one entity and/or to the environment. Additionally, or alternatively, the system is further configured to dynamically and adaptively determine a disincentive for disincentivizing context(s) associated with behavior(s) and/or activity(ies) of the at least one entity and/or for disincentivizing the behavior(s) and/or activity(ies) of the at least one entity associated with the context(s), when the context(s), behavior(s) and/or activity(ies) of the at least one entity is determined to be detrimental to the at least one entity and/or to the environment.

In exemplary embodiments, the system is configured to: facilitate redemption of the reward to thereby incentivize the creation, improvement, or increase in frequency or occurrence of context(s) associated with behavior(s) and/or activity(ies) and/or the creation, improvement, or increase in frequency or occurrence of behavior(s) and/or activity(ies) associated with context(s) of the at least one entity that is beneficial to the at least one entity and/or to the environment by one or more of a material reward, a physical reward, a financial reward, a monetary reward, an electronic reward, a virtual reward, a non-material reward, and non-financial reward; and/or facilitate redemption of the disincentive to thereby disincentivize the existence, occurrence, or frequency of context(s) associated with behavior(s) and/or activity(ies) and/or the existence, occurrence, or frequency of behavior(s) and/or activity(ies) associated with context(s) of the at least one entity that is detrimental to the at least one entity and/or to the environment by one or more of a material punishment or penalty, a physical punishment or penalty, a financial punishment or penalty, a monetary punishment or penalty, an electronic punishment or penalty, a virtual punishment or penalty, a non-material punishment or penalty, and a non-financial punishment or penalty.

In exemplary embodiments, a system comprises a contextualization engine. The contextualization engine is configured to: determine and/or predict one or more context(s) of at least one entity in one or more environment(s) from available and/or generated data including data from a plurality of devices, sensors, other systems, and/or communications network(s); compare the one or more context(s) and underlying and/or associated data/data sets with various other contexts and/or instances of one of more context(s) and underlying and/or associated data/data sets in other environment(s), to determine differences and commonalities among the contexts' underlying and/or associated data/data sets; and formulate actions, modifications, and/or adjustments needed to appropriately cross-reference, calibrate, adjust, modify, and/or synchronize the one or more contexts in the one or more environment(s) with other context(s) and/or instances of the one or more context(s) in other environment(s), for the purpose of adjusting, modifying, calibrating, synchronizing, compensating for, or otherwise taking into account the other contexts/instances of contexts' data into the one or more context(s) underlying and/or associated data elements to compensate for, adjust, modify, calibrate, synchronize, compensate for, and/or otherwise take into account the differences between the contexts and their underlying and/or associated data/data sets, for use in analyzing, comparing, diagnosing, treating, modifying, performing, executing, facilitating, discouraging, and/or operating one or more behaviors and/or activities associated with the contexts.

In exemplary embodiments, the system is configured to compensate for, adjust, modify, calibrate, synchronize, compensate for, and/or otherwise take into account the differences between the contexts and their underlying and/or associated data/data sets, for use in analyzing, comparing, diagnosing, treating, and/or modifying the behavior(s) and/or activity(ies) of the at least one entity, and/or for performing, executing, analyzing, facilitating, discouraging, and/or operating the activity(ies) of and/or associated with the at least one entity.

In exemplary embodiments, the contextualization engine is configured to capture, generate, and/or predict metadata associated with each data measurement of the one or more contexts to thereby enable the contextualization engine to perform an apples to apples cross-referencing, calibrating, adjusting, modifying, and/or synchronizing of the data obtained for the at least one entity for a particular purpose with data obtained elsewhere under a different instance(s) of the one or more context(s) for the same or similar purpose.

In exemplary embodiments, the contextualization engine is configured to holistically identify and set up sensors including associated parameters, operate and collect data from the sensors, organize and store the sensor data, process and analyze the sensor data, compare the sensor data with baseline(s) of applicable data and adjust the sensor data accordingly.

In exemplary embodiments, the system is configured to be operable for modifying the context(s) before and/or during a medical activity on the at least one entity by changing one or more of radiation level, gravity level, temperature, humidity, oxygen level, and noise level.

In exemplary embodiments, the contextualization engine is configured to develop a score or set of scores to capture the value of contextual factors of the context(s) associated with the at least one entity.

In exemplary embodiments, the system is configured to be operable for prescribing and/or applying artificial electromagnetic fields for health, safety, and/or treatment for the at least one entity within an off-Earth environment to preempt and/or lower the risk of a future occurrence of a psychological episode, which may be linked to reduced protection of the Earth's electromagnetic field coupled with a solar event(s).

In exemplary embodiments, the contextualization engine is configured to: determine and/or predict, through a plurality of measurements/readings taken by a plurality of different devices, sensors, other systems, and/or communication network(s) and/or through information from and/or about system inputs, the context(s) of the at least one entity within an environment; and determine whether the context(s) of the at least one entity should be adjusted before and/or during a test on the at least one entity for a particular purpose within the environment to thereby reduce or eliminate the need for subsequently cross-referencing, calibrating, adjusting, modifying, and/or synchronizing the medical/medical activity data obtained for the at least one entity within the environment to enable an apples to apples comparison with data obtained elsewhere under a different instance(s) of the context(s) for the same or similar purpose.

In exemplary embodiments, the contextualization engine is configured to cross-reference, calibrate, adjust, modify, and/or synchronize measurements of the plurality of different devices, sensors, other systems, and/or communications network(s) to determine, assess, and/or accommodate for different context(s) of the environment under which the plurality of different devices, sensors, other systems, and/or communications network(s) are being used. The cross-referencing, calibrating, adjusting, modifying, and/or synchronizing provides the ability to compare the medical/medical activity test data obtained for the at least one entity for the particular purpose within the environment with the data obtained elsewhere under different context(s) and/or instance(s) of the one or more contexts in a different environment(s) for the same or similar purpose.

In exemplary embodiments, the environment is an on-Earth specialty environment or off-Earth environment. And the contextualization engine is configured to determine whether the context(s) should be adjusted before and/or during the medical activity on the at least one entity for the particular purpose within the on-Earth specialty environment or off-Earth environment to thereby reduce or eliminate the need for subsequently calibrating, adjusting, and/or synchronizing the data obtained for the at least one entity within the on-Earth specialty environment or off-Earth environment and enable an apples to apples comparison with data in same or similar contexts obtained on-Earth in non-specialty/normal environment(s) for the same or similar purpose.

In exemplary embodiments, the system (e.g., via the contextualization engine, etc.) is configured to solicit and/or collect user feedback and to thereafter interpret the user feedback for use in determining the one or more context(s) of at least one entity in the one or more environment(s).

In exemplary embodiments, the system (e.g., via the contextualization engine, etc.) is configured to obtain and interpret human feedback for use in determining the one or more context(s) of at least one entity in the one or more environment(s).

In exemplary embodiments, the contextualization engine is configured for ongoing monitoring for useful context(s) that will, may, or could be encountered in the one or more environment(s) and for using data obtained from the ongoing monitoring for predicting future context(s) that the one or more environment(s) have not yet encountered but there is a likelihood the one or more environment(s) will encounter the predicted future context(s). In such exemplary embodiments, the contextualization engine may be predictive and provide truly pre-emptive context determination, where the context has not occurred yet and/or the behavior(s) and/or activity(ies) has not yet occurred in that context.

For example, the contextualization engine may perform a pre-emptive analysis of the context that would likely to occur if a Moon avalanche occurred with human(s) near/trapped by the moon avalanche. This is unlikely to happen in the immediate near future, but possible once building and more extensive human exploring occurs. In this example, the contextualization engine may be tied or linked with Moon operations and have information about upcoming excursion(s). The contextualization engine may pre-emptively draw on on-Earth avalanches or underground cave-ins, underwater shelf avalanches, or iceberg calving to collect data on what the context will be or need to be if an avalanche occurs on the Moon. Because this has never happened, the contextualization engine would be drawing on "similar" past contexts to predict the likely future context that rescuers may encounter, e.g., sharp edges of rocks that could cause sudden breaks in space suits requiring immediate setting up of shelters, very difficult terrain requiring the immediately powering up of (extra) specialized vehicles (that are the only ones capable of navigating through the debris), an immediate elevation in concern for oxygen supplies, supplies (e.g., it will take twice as long to return to base), much higher radiation exposure due to the victims being exposed much longer than planned, etc.

In exemplary embodiments, the system may be configured to adjust context(s) to improve outcome(s) after having determined an issue(s). The following are example context adjustments that may be made by the system in exemplary embodiments:

- Turning on lights when arriving at home to relieve anxiety. For example, someone comes home from work, the system detects (perhaps even subconsciously) that the person is nervous. The system will turn on driveway lights (e.g., in a peaceful, non-threatening way, etc.) as or shortly before the person is arriving. This assumes the system has determined that there is no active level of threat in place otherwise the system may operate differently.
- Gravity or pseudo gravity. Some conditions may be negatively impacted by the lack of gravity or pseudo gravity, so the system can detect this and then make alterations to spin up more pseudo gravity assuming the reward outweighs the risk for other impacted things
- Migraines. Person having migraines may see the lights dimmed by the system to alter the context.
- Atmosphere/Oxygen %. Person having breathing trouble or maybe in psychological distress may see atmospheric pressure and O2 content increased.
- Diet alterations. System may detect micro-nutrient issues and alter farther out diet plans (tie in to space farming patent).
- Psychological improvements (lighting changes or fragrance release). System may detect psychological discomfort and adjust lighting levels and perhaps release a pleasant fragrance like lavender to adjust the moon
- Electromagnetic field. System may prescribe or alter artificial electromagnetic fields
- Light (sunlight). System may determine that person is lacking real sunlight, so may direct them to an area where more raw light is available or open windows.
- Temperature. Adjust the temperature to respond to some issues so such overnight tweaking the temperature to ensure better sleep.
- Visual Surroundings (smart wallpaper or TV screen). Using smart wallpaper or TV screens may switch to display calming images or even personal images (such as a person's family photo) while they are passing by on an individualized basis.
- Sound (music). May provide music to avoid the background noise and provide a sense of personal space in terms of sound.

In exemplary embodiments, the system is configured to be operable for understanding and prescribing artificial electromagnetic fields and its influence on health and behavior. In such exemplary embodiments, the system is configured to prescribe and/or apply artificial electromagnetic fields for health, safety, and/or treatment. For example, the system may be configured to prescribe and/or apply artificial electromagnetic fields to help avoid or reduce the occurrence of psychological episodes, which may be linked to reduced protection of the Earth's electromagnetic field coupled with solar events. In exemplary embodiments, the system may also or alternatively be configured to prescribe and/or apply artificial electromagnetic fields to non-human entities, such as animals, plants, other systems, etc. The system may be configured to prescribe and/or apply artificial electromagnetic fields for health, safety, and/or treatment within an on-Earth environment or within an off-Earth, non-Earth, or specialty environment.

In exemplary embodiments, the system is configured to be operable for using any combination of location and context in relation to the ability to practice medicine and/or in some form provide guidance, assistance, and/or information to assist a person, directly or indirectly, with a medical issue personally or for an associate/loved one or provide background/educational information that is operating in a non-Earth locale or any time transiting through a non-Earth system.

In exemplary embodiments, the system is configured to be usable in an environment in which atypical Earth factors must be included and considered due to potential medical implications such as Earth's gravity, atmospheric conditions, exposure to non-traditional radiation source(s) or health hazards like galactic background radiation or solar winds and influence the needs for monitoring, diagnosis, prescriptive action, or further support combining this information for diagnosis and treatment by a human doctor or artificial intelligence (AI) health care system.

In exemplary embodiments, the system is configured to be usable for medical action and records including person(s), place(s), things(s), equipment, atmosphere, gravity, radiation levels, even computers/communications equipment/networks. In such exemplary embodiments, the system may be configured to be operable for melding/merging/updating records to accommodate for the system's ability to more frequently and more comprehensively capture/collect data (including context data), which will be particularly important in off-earth/specialty environments. The system may also be configured to be operable for capturing data including context data, modifying context, and/or modifying other data based on the context, such that the data collected and melded into the baseline data is done on an apple-to-apples basis in terms of the context within which the measurements were obtained.

In exemplary embodiments, the system is configured to be operable across multiple space based locations and the transit between these bodies, e.g., Earth to lunar orbit to Mars space station, Martian surface and return, etc. In such exemplary embodiments, the system may be configured to be operable for coordinating/linking a given measurement between locations, including adjusting the context(s) within which the measurements/assessment/actions are taken to providing the necessary data to enable an apples-to-apples comparison.

In exemplary embodiments, the system is configured to be operable within non-traditional Earth environments, such as enclosed facilities or abnormal conditions (e.g., Fukushima during disaster, Chernobyl, etc.).

In exemplary embodiments, the system is configured to be operable for translating environmental factors and studying, understanding and providing prescriptive information for immediate healthcare as well as support for research pursuits.

In exemplary embodiments, the system is configured to be operable for responding to dynamic contextual changing factors that can aid in diagnosis, treatment, action recommendation, preemptive action, and development and suggestion for future treatment. The system may be configured to be operable for using machine learning to identify possible useful drug compounds to reduce impact of microgravity.

In exemplary embodiments, the system is configured to be operable for assessing risk of physical and mental issues using the context of non-traditional environments.

In exemplary embodiments, the system is configured to be operable for assessing baseline conditions and context and monitoring any deviations of such while in a nontraditional environment.

In exemplary embodiments, the system is configured to be operable for determining and assessing how the context of environment (e.g., gravity, location, topology, atmosphere, internal vs. external differences, etc.) will impact the detection of/accurate triage/diagnosis of, let alone and/or preemption treatment of many ailments/diseases.

In exemplary embodiments, the system is configured to be operable for processing the data needed to adjust/react/calibrate space medicine-related activities that tend to be grossly inaccurate without detailed contextual understanding of the person's past, present, and future context.

In exemplary embodiments, the system is configured to be operable for problem solving for location and context for person(s) staying off-Earth for very extended periods of time (e.g., multiple years, etc.) and anticipating and mitigating any concerns thereof, e.g., gravity and radiation concerns, etc.

In exemplary embodiments, the system is configured to be operable to collect, analyze, and respond to data about different contexts that a person off-Earth (e.g., Moon, Mars, asteroids, other planets/moons, space station(s), in transit travel in various forms, etc.) is experiencing, has experienced, and/or will be experiencing, which data collection will be critical to the successful detection/diagnosis and treatment of an ailment.

In exemplary embodiments, the system is configured to be operable across multiple fields of medicine, science and engineering including but not limited to radiology to pharmacology to dentistry to psychology, and involve probably every underlying enabler, from health care records to test equipment to testing methods and processing to storage of pharmaceuticals and other future disciplines or needs that might arise.

In exemplary embodiments, the system is configured to be operable for using automated and human comparison mechanisms and controls using sensor/software-defined systems to rationalize the differences between various medical studies.

In exemplary embodiments, the system is configured to be operable for understanding the difference between location and context (such as date and time and place) and then providing insight based on the location and context. For example, an O2 reading at sea level may not be the same for a tourist trip to the Rocky Mountains In this example, the system would use this context (at sea level versus Rocky Mountain location) to better understand the diagnosis and understanding of what is happening with the O2 reading.

In exemplary embodiments, the system is configured to be operable for handling multiple locales and context to have multiple baselines, for example, Earth baseline and Lunar baseline. For example, what may be normal blood pressure on Earth could vary wildly on the lunar surface particularly over time for multiple fields including but not limited to radiology and pharmacology.

In exemplary embodiments, the system is configured to be operable for handling an entity's data (e.g., data for a person or animal, etc.), which data would be harmonized such that the data would be translatable across the journey through space. For example, during a 2-year journey to Mars with various contexts at a minimum, there would be Earth data, launch data, Earth-to-Moon data, flight to Mars under acceleration data, under deceleration data, orbit on Mars data, Martian surface data, and back again, for starters. All of the person's normal vital signs are going to manifest very differently under such conditions and solutions to assist in the monitoring and management is a novel innovation disclosed herein.

In exemplary embodiments, the system is configured to be operable for handling context-adjusted medical record(s).

In exemplary embodiments, the system is configured to be operable for handling context-based testing.

In exemplary embodiments, the system is configured to be operable for handling context-based, flexible diagnosis and treatment.

In exemplary embodiments, the system is configured to be operable for handling context-intensive continual learning.

In exemplary embodiments, the system is configured to be operable for handling the use of, integration of, and dynamic use of multiple architecture environments.

In exemplary embodiments, the system is configured to be operable for handling extensive, dynamic use of context-focused simulations.

In exemplary embodiments, the system is configured to be operable for handling local/edge/more powerful computing.

In exemplary embodiments, the system is configured to be operable for handling multi-entity, context-focused reference systems.

In exemplary embodiments, the system is configured to be operable for handling various data protocols to handle the inherent issues of solar scale, such as time lag, time dilation and signal disruption.

In exemplary embodiments, the system is configured to be operable for using time or translating time to an atomic clock to better suit the needs of interplanetary medicine and science.

In exemplary embodiments, the system is configured to be operable for using a system of coordinates to establish location, such as Earth GPS, Lunar GPS, and a coordinate system between the Earth and Moon in Cis-Lunar space.

In exemplary embodiments, the system is configured to be operable for rectifying recordkeeping both locally and in the master copy in situations dealing with time lag such as events occurring locally on Mars and recommendations that came from Earth but arrived minutes later due to signal lag.

In exemplary embodiments, the system is configured to be operable to synchronize, correct, coordinate, or otherwise link different times between on-Earth and off-Earth systems, applications, use cases, technologies, etc.

In exemplary embodiments, the system is configured to be operable for using location and context including "location" factors and context such as radiation, pressure, oxygen levels, CO2 levels, temperature (particularly in controlled environments and/or with an atmosphere), and light/light intensity and align the same with the time context.

In exemplary embodiments, the system is configured to be operable to provide contextual guidance using location and context such as recommendations of sleeping quarters, changes in diet, mental health, or other proscriptive actions.

In exemplary embodiments, the system is configured to be operable for using a heliocentric model or a geocentric model and the translation between the two.

In exemplary embodiments, the system is configured to include a localized data store and/or computing system(s) (e.g., edge computing, etc.) that enable the continual/periodic/event-based update/recalibration/adjustment of key personal data elements based on context.

In exemplary embodiments, the system is configured to be operable for leveraging edge computing while also understanding the context of needing additional support and communicating for more resources, such as computing resources to other hardware facilities.

In exemplary embodiments, the system is configured to be operable for supporting the dynamic, context-centric data disclosed herein that will require novel innovative data management, distribution, updating, maintaining, access, and delivery, particularly given a) variations in time/location/context reference systems across entities/off-Earth environments, b) the varying degrees of synchronization/coordination/use of such data elements across such environments, and c) the criticality of having much of this data as up-to-date/real-time as possible.

In exemplary embodiments, the system is configured to be operable for test application, conducting, measurement, results, and interpretation between non-typical environments and multiple locations and contexts such as the Moon's surface versus a lunar space station.

In exemplary embodiments, the system is configured to be operable for determining possible inaccuracies or contextual relevant factors to support decision making.

In exemplary embodiments, the system is configured to be operable for using location and context to support medicine practitioner education, training, reference, and assistance.

In exemplary embodiments, the system is configured to be operable 1) for utilizing traditional physicians (if highly trained) supported by various tools/capabilities (disclosed herein), and 2) for supporting "self-help" including self-help in conjunction with more personalized tools and machine learning/diagnosis/treatment capabilities.

In exemplary embodiments, the system is configured to be operable for using personal real-time, context adjusted readings from person sensors and edge computing, and/or various AI guidance situations. The ability to have a local reference management capability will be important to have local copies both digital and physical, which guides will be carefully curated to handle likely many different environments, gravities, atmospheres and unusual possible problems. The ability to have and support "AI Doctor/Surgeon/PA/Nurse"-type practitioners will become more critical the more complex an issue, the scarcer off-Earth resources become, the farther away (from Earth) the patient is, and the more time consuming/problematic communications become with "nearer" (to Earth) knowledgeable resources.

In exemplary embodiments, the system is configured to be operable for providing gravity management.

In exemplary embodiments, the system is configured to be operable for providing computer assisted diagnostic with gravity assessment and simulation.

In exemplary embodiments, the system is configured to be operable for providing medication guidance/consultation.

In exemplary embodiments, the system is configured to be operable for providing context-focused simulations including use of virtual and augmented reality, the metaverse, and/or machine learning/Artificial Intelligence to identify, setup, conduct/simulate, test, tailor/customize, and modify different mental, physical, and contextual variables so that potential diagnoses and/or treatments can be "tested" prior to actual application to the patient.

In exemplary embodiments, the system is configured to be operable for providing support of mental health, including support and context around anxiety, behavioral triggers or other risk events.

In exemplary embodiments, the system is configured to be operable for managing rewards or incentives and punishments or disincentives using location and context.

In exemplary embodiments, the system is configured to be operable for managing rewards or incentives and punishments or disincentives using location and context and context-based simulations, which are useful for mental health diagnosis and treatments.

In exemplary embodiments, the system is configured to be operable for employing virtual reality, augmented reality, metaverse (including the use of friendly, unfriendly, person/place/thing, and other types of avatars) and similar "different" reality environments through various mechanisms to thereby provide a way of exposing a patient to various situations and triggers and monitoring the impact on the patient.

In exemplary embodiments, the system is configured to be operable for using location and context to perform (near) simultaneous simulations on multiple entities that may be beneficial in multiple respects, e.g., improving computational algorithms by seeing conducting simultaneous tests using the same contextual elements and then changing such elements (particularly "real" elements) to determine if there are any differences in projected outcomes.

In exemplary embodiments, the system is configured to be operable with local/localized/edge computing and communications architectures, including extensive use of personal/personalized sensors on, in, attached to, or otherwise as close physically and/or mentally to the person as possible, in as near real-time as possible (e.g., use of metaverse for mental state simulation/determination/projection, etc.). This may include dynamic, context-based redirection/reallocation/rerouting of computational resources based on context.

In exemplary embodiments, a multi-entity, context-diverse reference system(s) is configured to enable synchronization, coordination, (re)calibration, and/or apples-to-apples comparison of data that is conceived on, referenced on/by, measured on/by, operated on/by, utilized on/by, or otherwise has data involving more than one entity and/or location in physical space, as well as virtual representations of or related to physical space in metaverse or other non-physical systems.

In exemplary embodiments, the system comprises a multi-entity system that is dynamic to accommodate for the changing relative position of the Earth to the Moon to the ship. In which case, the system may be configured to provide a fixed frame of reference, a relative frame of reference, or both.

In exemplary embodiments, the system is configured to be operable for providing a Solar Positioning System (SPS).

Although exemplary embodiments of systems are disclosed herein, the present disclosure is also directed to exemplary methods of performing the processes, steps, and/or operations that are disclosed herein for the systems. For example, an exemplary method includes determining and/or predicting one or more context(s) of at least one entity in one or more environment(s) from available and/or generated data including data from a plurality of devices, sensors, other systems, and/or communications network(s); comparing the one or more context(s) and underlying and/or associated data/data sets with various other contexts and/or instances of one of more context(s) and underlying and/or associated data/data sets in other environment(s), to determine differences and commonalities among the contexts' underlying and/or associated data/data sets; and formulating actions, modifications, and/or adjustments needed to appropriately cross-reference, calibrate, adjust, modify, and/or synchronize the one or more contexts in the one or more environment(s) with other context(s) and/or instances of the one or more context(s) in other environment(s), for the purpose of adjusting, modifying, calibrating, synchronizing, compensating for, or otherwise taking into account the other contexts/instances of contexts' data into the one or more context(s) underlying and/or associated data elements to compensate for, adjust, modify, calibrate, synchronize, compensate for, and/or otherwise take into account the differences between the contexts and their underlying and/or associated data/data sets, for use in analyzing, comparing, diagnosing, treating, modifying, performing, executing, facilitating, discouraging, and/or operating one or more behaviors and/or activities associated with the contexts.

Another exemplary method includes calibrating, cross-referencing, adjusting, modifying, and/or synchronizing measurements of a plurality of different devices, sensors, other systems, and/or communications network(s) automatically to determine, assess, accommodate for, and/or compare different context(s) and/or instances of the same or similar context(s) of an environment(s) under which the plurality of different devices, sensors, other systems, and/or communications network(s) will be, are being, and/or have been used, whereby the calibrating, cross-referencing, adjusting, modifying, and/or synchronizing provides the ability to compare data obtained for the context(s) and/or instances of the same or similar context(s) in an environment(s) associated with the at least one entity undergoing, involved in, and/or associated with a particular purpose, behavior, and/or activity via the plurality of different devices, sensors, other systems, and/or communications network(s) with data obtained elsewhere under different context(s) and/or instances of the same or similar context(s) in other environment(s) for the same or similar purpose, behavior, and/or activity.

In addition, the present disclosure is also directed to exemplary embodiments that include non-transitory computer-readable storage media comprising computer-executable instructions, which when executed by at least one processor, cause the at least one processor to be operable for performing processes, steps, and/or operations that are disclosed herein for the systems. For example, an exemplary embodiment includes non-transitory computer-readable storage media comprising computer-executable instructions, which when executed by at least one processor, cause the at least one processor to be operable for: determining and/or predicting one or more context(s) of at least one entity in one or more environment(s) from available and/or generated data including data from a plurality of devices, sensors, other systems, and/or communications network(s); comparing the one or more context(s) and underlying and/or associated data/data sets with various other contexts and/or instances of one of more context(s) and underlying and/or associated data/data sets in other environment(s), to determine differences and commonalities among the contexts' underlying and/or associated data/data sets; and formulating actions, modifications, and/or adjustments needed to appropriately cross-reference, calibrate, adjust, modify, and/or synchronize the one or more contexts in the one or more environment(s) with other context(s) and/or instances of the one or more context(s) in other environment(s), for the purpose of adjusting, modifying, calibrating, synchronizing, compensating for, or otherwise taking into account the other contexts/instances of contexts' data into the one or more context(s) underlying and/or associated data elements to compensate for, adjust, modify, calibrate, synchronize, compensate for, and/or otherwise take into account the differences between the contexts and their underlying and/or associated data/data sets, for use in analyzing, comparing, diagnosing, treating, modifying, performing, executing, facilitating, discouraging, and/or operating one or more behaviors and/or activities associated with the contexts.

Another exemplary embodiment includes non-transitory computer-readable storage media comprising computer-executable instructions, which when executed by at least one processor, cause the at least one processor to be operable for: calibrating, cross-referencing, adjusting, modifying, and/or synchronizing measurements of a plurality of different devices, sensors, other systems, and/or communications network(s) automatically to determine, assess, accommodate for, and/or compare different context(s) and/or instances of the same or similar context(s) of an environment(s) under which the plurality of different devices, sensors, other systems, and/or communications network(s) will be, are being, and/or have been used, whereby the calibrating, cross-referencing, adjusting, modifying, and/or synchronizing provides the ability to compare data obtained for the context(s) and/or instances of the same or similar context(s) in an environment(s) associated with the at least one entity undergoing, involved in, and/or associated with a particular purpose, behavior, and/or activity via the plurality of different devices, sensors, other systems, and/or communications network(s) with data obtained elsewhere under different context(s) and/or instances of the same or similar context(s) in other environment(s) for the same or similar purpose, behavior, and/or activity.

Exemplary embodiments may include one or more computing devices, such as one or more servers, workstations, personal computers, laptops, tablets, smartphones, person digital assistants (PDAs), etc. In addition, the computing device may include a single computing device, or it may include multiple computing devices located in close proximity or distributed over a geographic region, so long as the computing devices are specifically configured to function as described herein. Further, different components and/or arrangements of components than illustrated herein may be used in the computing device and/or in other computing device embodiments.

Exemplary embodiments may include one or more processors and memory coupled to (and in communication with) the one or more processors. A processor may include one or more processing units (e.g., in a multi-core configuration, etc.) such as, and without limitation, a central processing unit (CPU), a microcontroller, a reduced instruction set computer (RISC) processor, an application specific integrated circuit (ASIC), a programmable logic device (PLD), a gate array, and/or any other circuit or processor capable of the functions described herein.

In exemplary embodiments, a memory may be one or more devices that permit data, instructions, etc., to be stored therein and retrieved therefrom. The memory may include one or more computer-readable storage media, such as, without limitation, dynamic random access memory (DRAM), static random access memory (SRAM), read only memory (ROM), erasable programmable read only memory (EPROM), solid state devices, flash drives, CD-ROMs, thumb drives, and/or any other type of volatile or nonvolatile physical or tangible computer-readable media.

In exemplary embodiments, computer-executable instructions may be stored in the memory for execution by a processor to particularly cause the processor to perform one or more of the functions described herein, such that the memory is a physical, tangible, and non-transitory computer readable storage media. Such instructions often improve the efficiencies and/or performance of the processor that is performing one or more of the various operations herein. It should be appreciated that the memory may include a variety of different memories, each implemented in one or more of the functions or processes described herein.

In exemplary embodiments, a network interface may be coupled to (and in communication with) the processor and the memory. The network interface may include, without limitation, a wired network adapter, a wireless network adapter, a mobile network adapter, or other device capable of communicating to one or more different networks. In some exemplary embodiments, one or more network interfaces may be incorporated into or with the processor.

It should be appreciated that the functions described herein, in some embodiments, may be described in computer executable instructions stored on a computer readable media, and executable by one or more processors. The computer readable media is a non-transitory computer readable storage medium. By way of example, and not limitation, such computer-readable media can include RAM, ROM, EEPROM, CD-ROM or other optical disk storage, magnetic disk storage or other magnetic storage devices, or any other medium that can be used to carry or store desired program code in the form of instructions or databases and that can be accessed by a computer. Combinations of the above should also be included within the scope of computer-readable media.

It should also be appreciated that one or more aspects of the present disclosure transform a general-purpose computing device into a special-purpose computing device when configured to perform the functions, methods, and/or processes described herein.

Example embodiments are provided so that the present disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms, and that neither should be construed to limit the scope of the present disclosure. In some example embodiments, well-known processes, well-known device structures, and well-known technologies are not described in detail. For example, technical material that is known in the technical fields related to the present disclosure has not been described in detail so that the present disclosure is not unnecessarily obscured. This includes, but is not limited, to technology utilized in determining the location of mobile devices via a variety of means. In addition, advantages and improvements that may be achieved with one or more exemplary embodiments of the present disclosure are provided for purposes of illustration only and do not limit the scope of the present disclosure, as exemplary embodiments disclosed herein may provide all or none of the above mentioned advantages and improvements and still fall within the scope of the present disclosure.

The terminology used herein is for the purpose of describing particular example embodiments only and is not intended to be limiting. As used herein, the singular forms "a," "an," and "the" may be intended to include the plural forms as well, unless the context clearly indicates otherwise. In addition, as used herein, the term "or" is an inclusive "or" operator, and is equivalent to the term "and/or," unless the context clearly dictates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

Although the terms first, second, third, etc. may be used herein to describe various elements, components, or features, these elements, components, or features should not be limited by these terms. These terms may be only used to distinguish one element, component, or feature from another element, component, or feature. Terms such as "first," "second," and other numerical terms when used herein do not imply a sequence or order unless clearly indicated by the context. Thus, a first element, component, or feature could be termed a second element, component, or feature without departing from the teachings of the example embodiments.

None of the elements recited in the claims are intended to be a means-plus-function element within the meaning of 35 U.S.C. § 112(f) unless an element is expressly recited using the phrase "means for," or in the case of a method claim using the phrases "operation for" or "step for."

The foregoing description of the embodiments has been provided for purposes of illustration and description. It is not intended to be exhaustive or to limit the present disclosure. Individual elements, intended or stated uses, or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the present disclosure, and all such modifications are intended to be included within the scope of the present disclosure.

What is claimed is:

1. A system comprising a contextualization engine configured to:

determine and/or predict one or more context(s) of at least one entity in one or more environment(s) from available and/or generated data including data from a plurality of devices, sensors, other systems, and/or communications network(s);

compare the one or more context(s) and underlying and/or associated data/data sets with various other contexts and/or instances of one of more context(s) and underlying and/or associated data/data sets in other environment(s), to determine differences and commonalities among the contexts' underlying and/or associated data/data sets; and formulate actions, modifications, and/or adjustments needed to appropriately cross-reference, calibrate, adjust, modify, and/or synchronize the one or more contexts in the one or more environment(s) with other context(s) and/or instances of the one or more context(s) in other environment(s), for the purpose of adjusting, modifying, calibrating, synchronizing, compensating for, or otherwise taking into account the other contexts/instances of contexts' data into the one or more context(s) underlying and/or associated data elements to compensate for, adjust, modify, calibrate, synchronize, compensate for, and/or otherwise take into account the differences between the contexts and their underlying and/or associated data/data sets, for use in analyzing, comparing, diagnosing, treating, modifying, performing, executing, facilitating, discouraging, and/or operating one or more behaviors and/or activities associated with the contexts;

wherein the contextualization engine is configured to:

determine and/or predict, through a plurality of measurements/readings taken by a plurality of different devices, sensors, other systems, and/or communication network(s) and/or through information from and/or about system inputs, the context(s) of the at least one entity within an environment; and determine whether the context(s) of the at least one entity should be adjusted before and/or during a test on the at least one entity for a particular purpose within the environment to thereby reduce or eliminate the need for subsequently cross-referencing, calibrating, adjusting, modifying, and/or synchronizing the medical/medical activity data obtained for the at least one entity within the environment to enable an apples to apples comparison with data obtained elsewhere under a different instance(s) of the context(s) for the same or similar purpose;

wherein:

the environment is an on-Earth specialty environment or off-Earth environment; and the contextualization engine is configured to determine whether the context(s) should be adjusted before and/or during the medical activity on the at least one entity for the particular purpose within the on-Earth specialty environment or off-Earth environment to thereby reduce or eliminate the need for subsequently calibrating, adjusting, and/or synchronizing the data obtained for the at least one entity within the on-Earth specialty environment or off-Earth environment and enable an apples to apples comparison with data in same or similar contexts obtained on-Earth in non-specialty/normal environment(s) for the same or similar purpose.

2. The system of claim 1, wherein the system is configured to calibrate, cross-reference, adjust, modify, and/or synchronize measurements of a plurality of different devices, sensors, other systems, and/or communications network(s) automatically to determine, assess, accommodate for, and/or compare different context(s) and/or instances of the same or similar context(s) of an environment(s) under which the plurality of different devices, sensors, other systems, and/or communications network(s) will be, are being, and/or have been used, whereby the calibrating, cross-referencing, adjusting, modifying, and/or synchronizing provides the ability to compare data obtained for the context(s) and/or instances of the same or similar context(s) in an environment(s) associated with the at least one entity undergoing, involved in, and/or associated with a particular purpose, behavior, and/or activity via the plurality of different devices, sensors, other systems, and/or communications network(s) with data obtained elsewhere under different context(s) and/or instances of the same or similar context(s) in other environment(s) for the same or similar purpose, behavior, and/or activity.

3. The system of claim 1, wherein the system is configured with specialized machine learning and/or AI-based capability (ies) to calibrate, cross-reference, adjust, modify, and/or synchronize the measurements of the plurality of different devices, sensors, other systems, and/or communications network(s) automatically to accommodate for the different context(s) and/or instances of the one or more context(s) of the environment(s) under which the plurality of different devices, sensors, other systems, and/or communications network(s) will be, are being, and/or have been used.

4. The system of claim 1, wherein:

the environment is an off-Earth environment; and the system is configured to calibrate, cross-reference, adjust, modify, and/or synchronize the measurements of the plurality of different devices, sensors, other systems, and/or communications network(s) automatically to accommodate for the different context(s) and/or instances of the one or more context(s) of the off-Earth environment under which the plurality of different devices, sensors, other systems, and/or communications network(s) will be, are being, and/or have been used, whereby the calibrating, cross-referencing, adjusting, modifying, and/or synchronizing provides the ability to compare the data obtained for the context(s) and/or instances of the one or more context(s) within the off-Earth environment associated with the at least one entity undergoing, involved in, and/or associated with the particular purpose, behavior, and/or activity via the plurality of different devices, sensors, other systems, and/or communications network(s) with data obtained on-Earth for the same or similar purpose, behavior, and/or activity.

5. The system of claim 1, wherein:

the environment is an off-Earth environment, or the environment is an on-Earth enclosed facility and/or an on-Earth specialty environment having abnormal condition(s); and the at least one entity comprises one or more of a human, an animal, a plant, another system, a machine, a robot, an artificial intelligence, a virtual agent, a corporation, a business entity, a nation, a network, a driverless vehicle, a connected vehicle, a drone, and/or a governmental entity.

6. The system of claim 1, wherein the system is configured to be operable for prescribing and/or applying artificial electromagnetic fields for health, safety, and/or treatment for the at least one entity within the environment.

7. The system of claim 1, wherein the system comprises the plurality of different devices, sensors, other systems, and/or communications network(s), and wherein the system is configured to:

determine, through a plurality of measurements/readings taken by the plurality of different devices, sensors, other systems, and/or communication network(s) and/or through information from and/or about system inputs, behavior(s) and/or activity (ies) of at least one entity within an environment and:

(a) context(s) associated with the behavior(s) and/or activity (ies) of the at least one entity; or (b) location and the context(s) associated with the behavior(s) and/or activity (ies) of the at least one entity;

assess, evaluate, and predict a risk of a future occurrence(s) of context(s) associated with behavior(s) and/or activity (ies) of the at least one entity; and wherein the system is further configured to:

facilitate one or more actions and/or activities to preempt and/or lower the risk of a future occurrence(s) of context(s) associated with behavior(s) and/or activity (ies) of the at least one entity before the context(s) associated with the behavior(s) and/or activity (ies) occurs, when the context(s), behavior(s) and/or activity (ies) of the at least one entity is determined to be detrimental to the at least one entity and/or to the environment; and/or facilitate one or more actions and/or activities to preempt and/or lower the risk of a future occurrence(s) of behavior(s) and/or activity (ies) associated with the context(s) of the at least one entity before the behavior(s) and/or activity (ies) of the at least one entity occurs, when the context(s), behavior(s) and/or activity (ies) of the at least one entity is determined to be detrimental to the at least one entity and/or to the environment.

8. The system of claim 1, wherein the system comprises the plurality of different devices, sensors, other systems, and/or communications network(s), wherein the system is configured to determine, through a plurality of measurements/readings taken by the plurality of different devices, sensors, other systems, and/or communication network(s) and/or through information from and/or about system inputs, behavior(s) of at least one entity within an environment and context(s) associated with the behavior(s) and/or activity (ies) of the at least one entity, and wherein:

the system is further configured to dynamically and adaptively determine a reward for incentivizing context(s) associated with behavior(s) and/or activity (ies) of the at least one entity and/or for incentivizing behavior(s) and/or activity (ies) associated with the context(s) of the at least one entity, when the context(s), behavior(s) and/or activity (ies) of the at least one entity is determined to be beneficial to the at least one entity and/or to the environment; and/or the system is further configured to dynamically and adaptively determine a disincentive for disincentivizing context(s) associated with behavior(s) and/or activity (ies) of the at least one entity and/or for disincentivizing the behavior(s) and/or activity (ies) of the at least one entity associated with the context(s), when the context(s), behavior(s) and/or activity (ies) of the at least one entity is determined to be detrimental to the at least one entity and/or to the environment.

9. The system of claim 1, wherein the system is configured to be operable in an environment in which atypical Earth factors must be included and considered due to potential medical implications, such as Earth's gravity, atmospheric conditions, exposure to non-traditional radiation source(s), and health hazards like galactic background radiation or solar winds, whereby said atypical Earth factors influence the needs for monitoring, diagnosis, prescriptive action, and/or to further support diagnosis and treatment by a human doctor or artificial intelligence (AI) health care system.

10. The system of claim 1, wherein the system is configured to be operable for calibrating, cross-referencing, adjusting, modifying, comparing, synchronizing, and/or level setting of the measurements obtained using data collection, storage, processing, analysis, and/or application of capabilities and results of the plurality of different devices, sensors, other systems, and/or communications network(s) automatically to determine, assess, accommodate, and/or compare for different context(s) and/or instances of the same or similar context(s) of one or more environments under which the plurality of different devices, sensors, other systems, and/or communications network(s) will be, are being, and/or have been used, whereby the calibrating, cross-referencing, adjusting, modifying, comparing, synchronizing, and/or level setting provides the ability to compare data obtained for the context(s) and/or instances of the same or similar context(s) in an environment(s) associated with the at least one entity undergoing, involved in, and/or associated with a particular purpose, behavior, and/or activity via the plurality of different devices, sensors, other systems, and/or communications network(s) with data obtained elsewhere under different context(s) and/or instances of the same or similar context(s) in other environment(s) for the same or similar purpose, behavior, and/or activity.

11. The system of claim 1, wherein the system is configured to be operable automatically without manual human intervention.

12. The system of claim 1, wherein the system is configured to solicit and/or collect user feedback and to thereafter interpret the user feedback for use in determining the context(s) associated with the behavior(s) and/or activity (ies) of the at least one entity.

13. The system of claim 1, wherein the system is configured to obtain and interpret human feedback for use in determining the context(s) associated with the behavior(s) and/or activity (ies) of the at least one entity.

14. The system of claim 1 comprising a plurality of different devices, sensors, other systems, and/or communications network(s), the system configured to:

determine, through a plurality of measurements/readings taken by the plurality of different devices, sensors, other systems, and/or communication network(s) and/or through information from and/or about system inputs, behavior(s) and/or activity (ies) of at least one entity within or associated with an environment and:

(a) context(s) associated with the behavior(s) and/or activity (ies) of the at least one entity; or (b) location and the context(s) associated with the behavior(s) and/or activity (ies) of the at least one entity;

wherein the system is further configured to:

assess, evaluate, and predict a risk of a future occurrence(s) of context(s) associated with behavior(s) and/or activity (ies) of the at least one entity and/or a future occurrence(s) of behavior(s) and/or activity (ies) associated with a context(s) of the at least one entity; and facilitate one or more actions and/or activities to preempt and/or lower the risk of a future occurrence(s) of context(s) associated with behavior(s) and/or activity (ies) of the at least one entity before the context(s) associated with the behavior(s) and/or activity (ies) occurs when the context(s), behavior(s) and/or activity (ies) of the at least one entity is determined to be detrimental to the at least one entity and/or to the environment; and/or wherein the system is further configured to:

assess, evaluate, and predict a risk of a future occurrence(s) of behavior(s) and/or activity (ies) associated with a context(s) of the at least one entity; and facilitate one or more actions and/or activities to preempt and/or lower the risk of a future occurrence(s) of behavior(s) and/or activities associated with a context(s) of the at least one entity before the context(s), behavior(s) and/or activity (ies) occurs when the context(s), behavior(s) and/or activity(s) of the at least one entity is determined to be detrimental to the at least one entity and/or to the environment.

15. The system of claim 1, wherein the system is configured to compensate for, adjust, modify, calibrate, synchronize, compensate for, and/or otherwise take into account the differences between the contexts and their underlying and/or associated data/data sets, for use in analyzing, comparing, diagnosing, treating, and/or modifying the behavior(s) and/or activity (ies) of the at least one entity, and/or for performing, executing, analyzing, facilitating, discouraging, and/or operating the activity (ies) of and/or associated with the at least one entity.

16. The system of claim 1, wherein the contextualization engine is configured to capture, generate, and/or predict metadata associated with each data measurement of the one or more contexts to thereby enable the contextualization engine to perform an apples to apples cross-referencing, calibrating, adjusting, modifying, and/or synchronizing of the data obtained for the at least one entity for a particular purpose with data obtained elsewhere under a different instance(s) of the one or more context(s) for the same or similar purpose.

17. The system of claim 1, wherein the contextualization engine is configured to holistically identify and set up sensors including associated parameters, operate and collect data from the sensors, organize and store the sensor data, process and analyze the sensor data, compare the sensor data with baseline(s) of applicable data and adjust the sensor data accordingly.

18. The system of claim 1, wherein the system is configured to be operable for modifying the context(s) before and/or during a medical activity on the at least one entity by changing one or more of radiation level, gravity level, temperature, humidity, oxygen level, and noise level.

19. The system of claim 1, wherein the contextualization engine is configured to develop a score or set of scores to capture the value of contextual factors of the context(s) associated with the at least one entity.

20. The system of claim 1, wherein the contextualization engine is configured to cross-reference, calibrate, adjust, modify, and/or synchronize measurements of the plurality of different devices, sensors, other systems, and/or communications network(s) to determine, assess, and/or accommodate for different context(s) of the environment under which the plurality of different devices, sensors, other systems, and/or communications network(s) are being used, whereby the cross-referencing, calibrating, adjusting, modifying, and/or synchronizing provides the ability to compare the medical/medical activity test data obtained for the at least one entity for the particular purpose within the environment with the data obtained elsewhere under different context(s) and/or instance(s) of the one or more contexts in a different environment(s) for the same or similar purpose.

21. The system of claim 1, wherein the system is configured to solicit and/or collect user feedback and to thereafter interpret the user feedback for use in determining the one or more context(s) of at least one entity in the one or more environment(s).

22. The system of claim 1, wherein the system is configured to obtain and interpret human feedback for use in determining the one or more context(s) of at least one entity in the one or more environment(s).

23. The system of claim 1, wherein the contextualization engine is configured for ongoing monitoring for useful context(s) that will, may, or could be encountered in the one or more environment(s) and for using data obtained from the ongoing monitoring for predicting future context(s) that the one or more environment(s) have not yet encountered but there is a likelihood the one or more environment(s) will encounter the predicted future context(s).

24. A system comprising a contextualization engine configured to:

determine and/or predict one or more context(s) of at least one entity in one or more environment(s) from available and/or generated data including data from a plurality of devices, sensors, other systems, and/or communications network(s);

compare the one or more context(s) and underlying and/or associated data/data sets with various other contexts and/or instances of one of more context(s) and underlying and/or associated data/data sets in other environment(s), to determine differences and commonalities among the contexts' underlying and/or associated data/data sets; and formulate actions, modifications, and/or adjustments needed to appropriately cross-reference, calibrate, adjust, modify, and/or synchronize the one or more contexts in the one or more environment(s) with other context(s) and/or instances of the one or more context(s) in other environment(s), for the purpose of adjusting, modifying, calibrating, synchronizing, compensating for, or otherwise taking into account the other contexts/instances of contexts' data into the one or more context(s) underlying and/or associated data elements to compensate for, adjust, modify, calibrate, synchronize, compensate for, and/or otherwise take into account the differences between the contexts and their underlying and/or associated data/data sets, for use in analyzing, comparing, diagnosing, treating, modifying, performing, executing, facilitating, discouraging, and/or operating one or more behaviors and/or activities associated with the contexts;

wherein the system is configured to be operable for prescribing and/or applying artificial electromagnetic fields for health, safety, and/or treatment for the at least one entity within an off-Earth environment to preempt and/or lower the risk of a future occurrence of a psychological episode, which may be linked to reduced protection of the Earth's electromagnetic field coupled with a solar event(s).

25. The system of claim 24, wherein:

the environment is an off-Earth environment, or the environment is an on-Earth enclosed facility and/or an on-Earth specialty environment having abnormal condition(s); and the at least one entity comprises one or more of a human, an animal, a plant, another system, a machine, a robot, an artificial intelligence, a virtual agent, a corporation, a business entity, a nation, a network, a driverless vehicle, a connected vehicle, a drone, and/or a governmental entity.

26. The system of claim 24, wherein the system is configured to solicit and/or collect user feedback and to thereafter interpret the user feedback for use in determining the context(s) associated with the behavior(s) and/or activity (ies) of the at least one entity.

27. The system of claim 24, wherein the system is configured to obtain and interpret human feedback for use in determining the context(s) associated with the behavior(s) and/or activity (ies) of the at least one entity.

28. The system of claim 24 comprising a plurality of different devices, sensors, other systems, and/or communication network(s), the system configured to determine, through a plurality of measurements/readings taken by the plurality of different devices, sensors, other systems, and/or communication network(s) and/or through information from and/or about system inputs, behavior(s) and/or activity (ies) of at least one entity within an environment and context(s) associated with the behavior(s) and/or activity (ies) of the at least one entity, and wherein:

the system is further configured to dynamically and adaptively determine a reward for incentivizing context(s) associated with behavior(s) and/or activity (ies) of the at least one entity and/or for incentivizing behavior(s) and/or activity (ies) associated with the context(s) of the at least one entity, when the context(s), behavior(s) and/or activity (ies) of the at least one entity is determined to be beneficial to the at least one entity and/or to the environment; and/or the system is further configured to dynamically and adaptively determine a disincentive for disincentivizing context(s) associated with behavior(s) and/or activity (ies) of the at least one entity and/or for disincentivizing the behavior(s) and/or activity (ies) of the at least one entity associated with the context(s), when the context(s), behavior(s) and/or activity (ies) of the at least one entity is determined to be detrimental to the at least one entity and/or to the environment.

29. The system of claim 24, wherein the contextualization engine is configured to:

determine and/or predict, through a plurality of measurements/readings taken by a plurality of different devices, sensors, other systems, and/or communication network(s) and/or through information from and/or about system inputs, the context(s) of the at least one entity within an environment; and determine whether the context(s) of the at least one entity should be adjusted before and/or during a test on the at least one entity for a particular purpose within the environment to thereby reduce or eliminate the need for subsequently cross-referencing, calibrating, adjusting, modifying, and/or synchronizing the medical/medical activity data obtained for the at least one entity within the environment to enable an apples to apples comparison with data obtained elsewhere under a different instance(s) of the context(s) for the same or similar purpose.

30. The system of claim 29, wherein:

the environment is an off-Earth environment, or the environment is an on-Earth enclosed facility and/or an on-Earth specialty environment having abnormal condition(s); and the at least one entity comprises one or more of a human, an animal, a plant, another system, a machine, a robot, an artificial intelligence, a virtual agent, a corporation, a business entity, a nation, a network, a driverless vehicle, a connected vehicle, a drone, and/or a governmental entity.

31. The system of claim 29, wherein:

the environment is an on-Earth specialty environment or off-Earth environment; and the contextualization engine is configured to determine whether the context(s) should be adjusted before and/or during the medical activity on the at least one entity for the particular purpose within the on-Earth specialty environment or off-Earth environment to thereby reduce or eliminate the need for subsequently calibrating, adjusting, and/or synchronizing the data obtained for the at least one entity within the on-Earth specialty environment or off-Earth environment and enable an apples to apples comparison with data in same or similar contexts obtained on-Earth in non-specialty/normal environment(s) for the same or similar purpose.

* * * * *